(12) United States Patent
Fu et al.

(10) Patent No.: US 8,541,457 B2
(45) Date of Patent: Sep. 24, 2013

(54) AMINOTHIAZOLE DERIVATIVES AS HUMAN STEAROYL-CoA DESATURASE INHIBITORS

(75) Inventors: Jianmin Fu, Coquitlam (CA); Duanjie Hou, Burnaby (CA); Rajender Kamboj, Burnaby (CA); Vishnumurthy Kodumuru, Burnaby (CA); Natalia Pokrovskaia, New Westminster (CA); Vandna Raina, Burnaby (CA); Shaoyi Sun, Coquitlam (CA); Serguei Sviridov, Burnaby (CA); Zaihui Zhang, Vancouver (CA)

(73) Assignee: Xenon Pharmaceuticals Inc., Burnaby, B.C. (CA)

( * ) Notice: Subject to any disclaimer, the term of this patent is extended or adjusted under 35 U.S.C. 154(b) by 958 days.

(21) Appl. No.: 11/916,243

(22) PCT Filed: Jun. 5, 2006

(86) PCT No.: PCT/US2006/021660
§ 371 (c)(1),
(2), (4) Date: Nov. 20, 2009

(87) PCT Pub. No.: WO2007/130075
PCT Pub. Date: Nov. 15, 2007

(65) Prior Publication Data
US 2010/0152187 A1     Jun. 17, 2010

Related U.S. Application Data

(60) Provisional application No. 60/687,133, filed on Jun. 3, 2005.

(51) Int. Cl.
*A01N 43/78* (2006.01)
*A61K 31/425* (2006.01)

(52) U.S. Cl.
USPC .......................................... 514/371; 514/359

(58) Field of Classification Search
None
See application file for complete search history.

(56) References Cited

U.S. PATENT DOCUMENTS

| | | | |
|---|---|---|---|
| 2,985,657 A | 5/1961 | Janssen | 260/256.4 |
| 3,538,097 A | 11/1970 | Loewe et al. | 260/268 |
| 3,830,924 A | 8/1974 | Berkelhammer et al. | 424/270 |
| 3,975,384 A | 8/1976 | Narr et al. | 260/243 R |
| 4,026,891 A | 5/1977 | Austel et al. | 260/250 AH |
| 4,247,551 A | 1/1981 | Bellasio et al. | 424/248.56 |
| 4,435,401 A | 3/1984 | Campbell et al. | 424/251 |
| 4,439,606 A | 3/1984 | Du et al. | 544/356 |
| 4,459,296 A | 7/1984 | Ancher et al. | 424/244 |
| 5,001,125 A | 3/1991 | Stokbroekx et al. | 514/252 |
| 5,166,147 A | 11/1992 | Earl | 514/252 |
| 5,286,728 A | 2/1994 | Ferrini | 514/255 |
| 5,310,499 A | 5/1994 | Scherowsky et al. | 252/299.61 |
| 5,334,328 A | 8/1994 | Scherowsky et al. | 252/299.61 |
| 5,380,726 A | 1/1995 | Ferrini | 514/255 |
| 5,384,070 A | 1/1995 | Hemmerling et al. | 252/299.61 |
| 5,463,071 A | 10/1995 | Himmelsbach et al. | 548/251 |
| 5,494,908 A | 2/1996 | O'Malley et al. | 514/228.2 |
| 5,512,207 A | 4/1996 | Manero et al. | 252/299.61 |
| 5,527,763 A | 6/1996 | Miyazaki et al. | 504/242 |
| 5,547,605 A | 8/1996 | Fuss et al. | 252/299.6 |
| 5,637,592 A | 6/1997 | Heeres et al. | 514/252 |
| 5,668,148 A | 9/1997 | Payne et al. | 514/314 |
| 5,719,154 A | 2/1998 | Tucker et al. | 514/252 |
| 5,728,700 A | 3/1998 | Heeres et al. | 514/252 |
| 5,847,149 A | 12/1998 | Fuss et al. | 548/136 |
| 5,849,759 A | 12/1998 | Arnaiz et al. | 514/322 |
| 5,874,023 A | 2/1999 | Manero et al. | 252/299.61 |
| 5,882,546 A | 3/1999 | Manero et al. | 252/299.62 |
| 5,904,877 A | 5/1999 | Manero et al. | 252/299.62 |
| 5,911,913 A | 6/1999 | Manero et al. | 252/299.61 |
| 5,942,618 A | 8/1999 | Manero et al. | 546/139 |
| 5,965,761 A | 10/1999 | Buchecker et al. | 556/440 |
| 5,985,878 A | 11/1999 | Stokbroekx et al. | 514/252 |

(Continued)

FOREIGN PATENT DOCUMENTS

| | | |
|---|---|---|
| CA | 2052510 A1 | 4/1992 |
| CA | 2114178 A1 | 7/1994 |

(Continued)

OTHER PUBLICATIONS

Castro et al., "Pyridazine derivatives XII. Synthesis and antipsychotic-antidepressant activity of some butyrophenone derivatives of 6-phenylpyridazine," *Eur. J. Med. Chem.* 29: 831-839, 1994.
Contreras et al., "Aminopyridazines as Acetylcholinesterase Inhibitors," *J. Med. Chem.* 42(4): 730-741, 1999.
Ivanov et al., CAPLUS, Accession No. 137339-85-6, 1991, 1 page; see also, Ivanov et al., "Spectral Properties of Bisbenzimidasoles Interacting with Nucleic Acids," *Bioorganicheskaya Khimiya* 17(8): 1041-1047, 1991.
Kumar et al., "Possible Anthelmintic Agents : Syntheses of Ethyl 5(6)-[5(6)-Substituted-2-benzimidazolyl]benzimidazole-2-carbamates & Ethyl 4,6-Dinitro-5-substituted-amino-benzimidazole-2-carbamates," *Indian J. Chem.* 20B: 254-256, Mar. 1981.

(Continued)

*Primary Examiner* — Jeffrey S. Lundgren
*Assistant Examiner* — Meghan Finn
(74) *Attorney, Agent, or Firm* — Seed IP Law Group PLLC

(57) ABSTRACT

Methods of treating an SCD-mediated disease or condition in a mammal, preferably a human, are disclosed, wherein the methods comprise administering to a mammal in need thereof a compound of formula (I), where V, W, $R^1$, $R^2$, $R^3$ and $R^4$ are defined herein. Pharmaceutical compositions comprising the compounds of formula (I) are also disclosed.

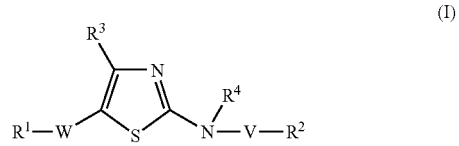

4 Claims, No Drawings

(56) References Cited

U.S. PATENT DOCUMENTS

| | | | |
|---|---|---|---|
| 5,994,356 A | 11/1999 | Pieper et al. | 514/252 |
| 5,998,412 A | 12/1999 | Broka et al. | 514/250 |
| 6,127,382 A | 10/2000 | Beard et al. | 514/311 |
| 6,156,758 A | 12/2000 | Kung et al. | 514/260 |
| 6,245,916 B1 | 6/2001 | Fauchere et al. | 548/263.8 |
| 6,251,911 B1 | 6/2001 | Bold et al. | 514/258 |
| 6,372,746 B1 | 4/2002 | Corbera-Arjona et al. | 514/252.14 |
| 6,441,000 B1 | 8/2002 | Gibson et al. | 514/322 |
| 6,482,479 B1 | 11/2002 | Dübal et al. | 428/1.1 |
| 6,489,328 B2 * | 12/2002 | Snow et al. | 514/252.16 |
| 6,500,956 B1 | 12/2002 | Geissler et al. | 546/257 |
| 6,562,827 B1 | 5/2003 | Lubisch et al. | 514/252.13 |
| 6,562,847 B1 | 5/2003 | Lee | 514/343 |
| 6,620,811 B2 | 9/2003 | Flohr et al. | 514/233.8 |
| 6,627,630 B1 | 9/2003 | Kawano et al. | 514/248 |
| 6,677,452 B1 | 1/2004 | Chen et al. | 544/365 |
| 6,911,447 B2 | 6/2005 | Mazur et al. | 514/253.05 |
| 6,916,812 B2 | 7/2005 | Poindexter et al. | 514/235.8 |
| 7,064,215 B2 | 6/2006 | Renhowe et al. | 548/125 |
| 7,115,607 B2 | 10/2006 | Fotsch et al. | 514/252.13 |
| 7,125,877 B2 | 10/2006 | Kobayashi et al. | 514/254.06 |
| 7,160,878 B2 | 1/2007 | Herron et al. | 514/218 |
| 7,220,736 B2 | 5/2007 | Yamada et al. | 514/211.1 |
| 7,220,744 B2 | 5/2007 | Jolidon et al. | 514/235.8 |
| 7,294,626 B2 | 11/2007 | Hohlweg | 514/252.02 |
| 7,319,099 B2 | 1/2008 | Jolidon et al. | 514/245 |
| 7,335,658 B2 | 2/2008 | Chakka et al. | 514/252.02 |
| 7,345,043 B2 | 3/2008 | Anandan et al. | 514/254.02 |
| 7,390,813 B1 | 6/2008 | Gray-Keller et al. | 514/255 |
| 7,399,765 B2 | 7/2008 | Bunnelle et al. | 514/252.06 |
| 7,423,030 B2 | 9/2008 | Augereau et al. | 514/210.21 |
| 7,491,729 B2 | 2/2009 | Bakker et al. | 514/267 |
| 7,547,698 B2 | 6/2009 | Kamboj et al. | 514/248 |
| 7,572,796 B2 | 8/2009 | Schadt et al. | 514/254.09 |
| 7,592,343 B2 | 9/2009 | Kamboj et al. | 514/252.01 |
| 7,595,316 B2 | 9/2009 | Ohtake et al. | 514/247 |
| 7,632,950 B2 | 12/2009 | Kuwabara et al. | 546/255 |
| 7,662,249 B2 | 2/2010 | Chisholm et al. | 514/249 |
| 7,767,677 B2 | 8/2010 | Kamboj et al. | 514/252.02 |
| 7,777,036 B2 | 8/2010 | Kamboj et al. | 544/367 |
| 2002/0045613 A1 | 4/2002 | Pauls et al. | 514/210.18 |
| 2002/0198237 A1 | 12/2002 | Bogenstaetter et al. | 514/326 |
| 2003/0106169 A1 | 6/2003 | Vidal et al. | 8/405 |
| 2003/0127627 A1 | 7/2003 | Amakawa et al. | 252/299.01 |
| 2003/0157552 A1 | 8/2003 | Hayden et al. | 435/7.1 |
| 2003/0166932 A1 | 9/2003 | Beard et al. | 544/238 |
| 2003/0203893 A1 | 10/2003 | Barth et al. | 514/215 |
| 2003/0225076 A1 | 12/2003 | Biwersi et al. | 514/230.5 |
| 2003/0225097 A1 | 12/2003 | Block et al. | 514/252.01 |
| 2004/0082586 A1 | 4/2004 | Plant et al. | 514/252.05 |
| 2004/0087577 A1 | 5/2004 | Pratt et al. | 514/222.8 |
| 2004/0092524 A1 | 5/2004 | Perez et al. | 514/249 |
| 2004/0097492 A1 | 5/2004 | Pratt et al. | 514/222.8 |
| 2004/0116417 A1 | 6/2004 | Boubia et al. | 514/227.8 |
| 2004/0147573 A1 | 7/2004 | Eriksson et al. | 514/369 |
| 2004/0176380 A1 | 9/2004 | Hoffmann et al. | 514/251 |
| 2004/0192701 A1 | 9/2004 | Iwata et al. | 514/253.09 |
| 2004/0220171 A1 | 11/2004 | Pauls et al. | 514/210.2 |
| 2004/0220191 A1 | 11/2004 | Schwink et al. | 514/252.03 |
| 2005/0014765 A1 | 1/2005 | Mailliet et al. | 514/254.02 |
| 2005/0014942 A1 | 1/2005 | Maruyama et al. | 544/183 |
| 2005/0020593 A1 | 1/2005 | Mailliet et al. | 514/243 |
| 2005/0059668 A1 | 3/2005 | Alberati-Giani et al. | 514/252.13 |
| 2005/0065143 A1 | 3/2005 | Chakka et al. | 514/218 |
| 2005/0075345 A1 | 4/2005 | Heymans et al. | 514/254.02 |
| 2005/0119251 A1 | 6/2005 | Fu et al. | 514/218 |
| 2005/0124660 A1 | 6/2005 | Antel et al. | 514/326 |
| 2005/0130989 A1 | 6/2005 | Le-Brun et al. | 514/254.05 |
| 2005/0234046 A1 | 10/2005 | Zhao et al. | 514/218 |
| 2006/0009459 A1 | 1/2006 | Chakka et al. | 514/252.01 |
| 2007/0082908 A1 | 4/2007 | Nakahira et al. | 514/243 |
| 2007/0299081 A1 | 12/2007 | Kamboj et al. | 514/252.03 |
| 2008/0108629 A1 | 5/2008 | Kamboj et al. | 514/254.03 |
| 2008/0167321 A1 | 7/2008 | Kamboj et al. | 514/253.13 |
| 2008/0188488 A1 | 8/2008 | Kamboj et al. | 514/255.03 |
| 2008/0207587 A1 | 8/2008 | Kamboj et al. | 514/210.18 |
| 2009/0197894 A1 | 8/2009 | Fu et al. | 514/253.13 |
| 2009/0291957 A1 | 11/2009 | Kamboj et al. | 514/248 |
| 2009/0306090 A1 | 12/2009 | Kamboj et al. | 514/252.02 |
| 2010/0305138 A1 | 12/2010 | Abreo et al. | |

FOREIGN PATENT DOCUMENTS

| | | |
|---|---|---|
| DE | 23 41 925 A1 | 3/1975 |
| DE | 24 27 943 A1 | 1/1976 |
| DE | 27 05 641 A1 | 8/1977 |
| DE | 35 36 030 A1 | 4/1987 |
| DE | 43 43 286 A1 | 6/1995 |
| DE | 44 23 044 A1 | 1/1996 |
| DE | 199 34 799 A1 | 2/2001 |
| DE | 102 59 382 A1 | 7/2004 |
| EP | 0 009 655 A1 | 4/1980 |
| EP | 0 055 583 A1 | 7/1982 |
| EP | 0 200 024 A2 | 11/1986 |
| EP | 0 300 526 A2 | 1/1989 |
| EP | 0 320 032 A1 | 6/1989 |
| EP | 0 385 350 B1 | 9/1990 |
| EP | 0 156 433 B1 | 2/1991 |
| EP | 0 438 230 B1 | 7/1991 |
| EP | 0 524 146 A1 | 1/1993 |
| EP | 0 533 344 A1 | 3/1993 |
| EP | 0 548 798 A1 | 6/1993 |
| EP | 0 606 824 A1 | 7/1994 |
| EP | 0 211 457 A2 | 2/1997 |
| EP | 0 927 992 A1 | 7/1999 |
| EP | 1 035 115 B1 | 9/2000 |
| EP | 1 048 652 A1 | 11/2000 |
| EP | 1 156 045 A1 | 11/2001 |
| EP | 1 180 514 A1 | 2/2002 |
| EP | 1 184 442 A1 | 3/2002 |
| EP | 1 243 268 A1 | 9/2002 |
| EP | 1 277 729 A1 | 1/2003 |
| EP | 1 375 495 A1 | 1/2004 |
| EP | 1 386 915 A1 | 2/2004 |
| EP | 1 396 487 A1 | 3/2004 |
| EP | 1 452 525 A1 | 9/2004 |
| EP | 1 452 530 A1 | 9/2004 |
| FR | 2 273 545 A1 | 1/1976 |
| FR | 2 868 780 A1 | 10/2005 |
| GB | 2 136 801 A | 9/1984 |
| JP | 10007572 A | 1/1998 |
| JP | 2004-203871 A | 7/2004 |
| WO | WO 88/07527 A1 | 10/1988 |
| WO | WO 88/08424 A1 | 11/1988 |
| WO | WO 91/09594 A1 | 7/1991 |
| WO | WO 91/09849 A1 | 7/1991 |
| WO | WO 92/18478 A1 | 10/1992 |
| WO | WO 93/00313 A2 | 1/1993 |
| WO | WO 93/01181 A1 | 1/1993 |
| WO | WO 93/14077 A1 | 7/1993 |
| WO | WO 93/18016 A1 | 9/1993 |
| WO | WO 94/07856 A1 | 4/1994 |
| WO | WO 94/12495 A1 | 6/1994 |
| WO | WO 94/26720 A1 | 11/1994 |
| WO | WO 93/25550 A1 | 12/1994 |
| WO | WO 95/25443 A1 | 9/1995 |
| WO | WO 96/01818 A1 | 1/1996 |
| WO | WO 96/01821 A1 | 1/1996 |
| WO | WO 96/01822 A1 | 1/1996 |
| WO | WO 96/11210 A1 | 4/1996 |
| WO | WO 96/33251 A1 | 10/1996 |
| WO | WO 97/03054 A1 | 1/1997 |
| WO | WO 97/21708 A1 | 6/1997 |
| WO | WO 97/26258 A1 | 7/1997 |
| WO | WO 97/28128 A1 | 8/1997 |
| WO | WO 97/37975 A1 | 10/1997 |
| WO | WO 98/01446 A1 | 1/1998 |
| WO | WO 98/04544 A1 | 2/1998 |
| WO | WO 98/14450 A1 | 4/1998 |
| WO | WO 99/00386 A1 | 1/1999 |
| WO | WO 99/14212 A1 | 3/1999 |
| WO | WO 99/20606 A2 | 4/1999 |
| WO | WO 99/21834 A1 | 5/1999 |

| | | | | | | | |
|---|---|---|---|---|---|---|---|
| WO | WO 99/41244 | A1 | 8/1999 | WO | WO 03/076401 | A1 | 9/2003 |
| WO | WO 99/43671 | A1 | 9/1999 | WO | WO 03/076422 | A1 | 9/2003 |
| WO | WO 99/47507 | A2 | 9/1999 | WO | WO 03/076430 | A1 | 9/2003 |
| WO | WO 99/54305 | A1 | 10/1999 | WO | WO 03/078413 | A1 | 9/2003 |
| WO | WO 99/55675 | A1 | 11/1999 | WO | WO 03/080060 | A1 | 10/2003 |
| WO | WO 99/58526 | A1 | 11/1999 | WO | WO 03/087086 | A2 | 10/2003 |
| WO | WO 99/64416 | A2 | 12/1999 | WO | WO 03/091247 | A2 | 11/2003 |
| WO | WO 99/64417 | A2 | 12/1999 | WO | WO 03/092678 | A1 | 11/2003 |
| WO | WO 00/21959 | A1 | 4/2000 | WO | WO 03/092686 | A1 | 11/2003 |
| WO | WO 00/25768 | A1 | 5/2000 | WO | WO 03/095432 | A1 | 11/2003 |
| WO | WO 00/32193 | A1 | 6/2000 | WO | WO 03/106456 | A1 | 12/2003 |
| WO | WO 00/32582 | A1 | 6/2000 | WO | WO 2004/000318 | A2 | 12/2003 |
| WO | WO 00/44755 | A1 | 8/2000 | WO | WO 2004/000820 | A2 | 12/2003 |
| WO | WO 00/47553 | A1 | 8/2000 | WO | WO 2004/009587 | A1 | 1/2004 |
| WO | WO 00/55139 | A2 | 9/2000 | WO | WO 2004/010927 | A2 | 2/2004 |
| WO | WO 00/59509 | A1 | 10/2000 | WO | WO 2004/011418 | A1 | 2/2004 |
| WO | WO 00/66578 | A1 | 11/2000 | WO | WO 2004/011430 | A1 | 2/2004 |
| WO | WO 00/69987 | A1 | 11/2000 | WO | WO 2004/014871 | A1 | 2/2004 |
| WO | WO 00/71536 | A1 | 11/2000 | WO | WO 2004/022061 | A1 | 3/2004 |
| WO | WO 01/07409 | A1 | 2/2001 | WO | WO 2004/022556 | A1 | 3/2004 |
| WO | WO 01/17942 | A1 | 3/2001 | WO | WO 2004/022559 | A1 | 3/2004 |
| WO | WO 01/19798 | A2 | 3/2001 | WO | WO 2004/026863 | A1 | 4/2004 |
| WO | WO 01/19822 | A1 | 3/2001 | WO | WO 2004/026865 | A1 | 4/2004 |
| WO | WO 01/22938 | A1 | 4/2001 | WO | WO 2004/035549 | A1 | 4/2004 |
| WO | WO 01/32628 | A1 | 5/2001 | WO | WO 2004/037809 | A1 | 5/2004 |
| WO | WO 01/44213 | A1 | 6/2001 | WO | WO 2004/039780 | A1 | 5/2004 |
| WO | WO 01/46164 | A1 | 6/2001 | WO | WO 2004/046130 | A1 | 6/2004 |
| WO | WO 01/47921 | A1 | 7/2001 | WO | WO 2004/048321 | A1 | 6/2004 |
| WO | WO 01/60369 | A1 | 8/2001 | WO | WO 2004/058727 | A1 | 7/2004 |
| WO | WO 01/60458 | A2 | 8/2001 | WO | WO 2004/065378 | A1 | 8/2004 |
| WO | WO 01/62233 | A2 | 8/2001 | WO | WO 2004/065380 | A1 | 8/2004 |
| WO | WO 01/62954 | A2 | 8/2001 | WO | WO 2004/069227 | A1 | 8/2004 |
| WO | WO 01/64646 | A2 | 9/2001 | WO | WO 2004/069792 | A2 | 8/2004 |
| WO | WO 01/68619 | A1 | 9/2001 | WO | WO 2004/069812 | A1 | 8/2004 |
| WO | WO 01/70668 | A2 | 9/2001 | WO | WO 2004/074253 | A1 | 9/2004 |
| WO | WO 01/81310 | A1 | 11/2001 | WO | WO 2004/074266 | A1 | 9/2004 |
| WO | WO 01/83460 | A1 | 11/2001 | WO | WO 2004/076413 | A2 | 9/2004 |
| WO | WO 01/96323 | A1 | 12/2001 | WO | WO 2004/078716 | A1 | 9/2004 |
| WO | WO 01/96327 | A1 | 12/2001 | WO | WO 2004/089416 | A2 | 10/2004 |
| WO | WO 01/97810 | A2 | 12/2001 | WO | WO 2004/096810 | A1 | 11/2004 |
| WO | WO 02/08221 | A2 | 1/2002 | WO | WO 2004/101581 | A2 | 11/2004 |
| WO | WO 02/26944 | A2 | 4/2002 | WO | WO 2004/108676 | A1 | 12/2004 |
| WO | WO 02/30405 | A2 | 4/2002 | WO | WO 2004/110350 | A2 | 12/2004 |
| WO | WO 02/30927 | A1 | 4/2002 | WO | WO 2005/003087 | A1 | 1/2005 |
| WO | WO 02/32857 | A1 | 4/2002 | WO | WO 2005/007644 | A1 | 1/2005 |
| WO | WO 02/46151 | A1 | 6/2002 | WO | WO 2005/009976 | A1 | 2/2005 |
| WO | WO 02/46170 | A2 | 6/2002 | WO | WO 2005/009980 | A1 | 2/2005 |
| WO | WO 02/055012 | A2 | 7/2002 | WO | WO 2005/011653 | A2 | 2/2005 |
| WO | WO 02/055013 | A2 | 7/2002 | WO | WO 2005/011654 | A2 | 2/2005 |
| WO | WO 02/055014 | A2 | 7/2002 | WO | WO 2005/011655 | A2 | 2/2005 |
| WO | WO 02/055496 | A1 | 7/2002 | WO | WO 2005/011656 | A2 | 2/2005 |
| WO | WO 02/066446 | A1 | 8/2002 | WO | WO 2005/011657 | A2 | 2/2005 |
| WO | WO 02/072548 | A2 | 9/2002 | WO | WO 2005/011700 | A1 | 2/2005 |
| WO | WO 02/074767 | A1 | 9/2002 | WO | WO 2005/012304 | A2 | 2/2005 |
| WO | WO 02/081453 | A1 | 10/2002 | WO | WO 2005/012307 | A1 | 2/2005 |
| WO | WO 02/083624 | A1 | 10/2002 | WO | WO 2005/014563 | A1 | 2/2005 |
| WO | WO 02/088093 | A1 | 11/2002 | WO | WO 2005/016910 | A1 | 2/2005 |
| WO | WO 02/096867 | A2 | 12/2002 | WO | WO 2005/021548 | A2 | 3/2005 |
| WO | WO 02/096867 | A3 | 12/2002 | WO | WO 2005/021550 | A1 | 3/2005 |
| WO | WO 02/102778 | A1 | 12/2002 | WO | WO 2005/023260 | A1 | 3/2005 |
| WO | WO 03/003008 | A1 | 1/2003 | WO | WO 2005/023261 | A1 | 3/2005 |
| WO | WO 03/011843 | A1 | 2/2003 | WO | WO 2005/028477 | A1 | 3/2005 |
| WO | WO 03/016306 | A1 | 2/2003 | WO | WO 2005/028479 | A2 | 3/2005 |
| WO | WO 03/018563 | A1 | 3/2003 | WO | WO 2005/030140 | A2 | 4/2005 |
| WO | WO 03/022274 | A2 | 3/2003 | WO | WO 2005/030188 | A2 | 4/2005 |
| WO | WO 03/035602 | A1 | 5/2003 | WO | WO 2005/032468 | A2 | 4/2005 |
| WO | WO 03/037862 | A1 | 5/2003 | WO | WO 2005/034952 | A2 | 4/2005 |
| WO | WO 03/037871 | A1 | 5/2003 | WO | WO 2005/037839 | A1 | 4/2005 |
| WO | WO 03/037872 | A1 | 5/2003 | WO | WO 2005/039550 | A2 | 5/2005 |
| WO | WO 03/040125 | A1 | 5/2003 | WO | WO 2005/040109 | A1 | 5/2005 |
| WO | WO 03/043636 | A1 | 5/2003 | WO | WO 2005/040136 | A1 | 5/2005 |
| WO | WO 03/045920 | A1 | 6/2003 | WO | WO 2005/044192 | A2 | 5/2005 |
| WO | WO 03/045921 | A1 | 6/2003 | WO | WO 2005/044797 | A1 | 5/2005 |
| WO | WO 03/050088 | A1 | 6/2003 | WO | WO 2005/049616 | A1 | 6/2005 |
| WO | WO 03/051797 | A2 | 6/2003 | WO | WO 2005/049617 | A1 | 6/2005 |
| WO | WO 03/066604 | A2 | 8/2003 | WO | WO 2005/060665 | A2 | 7/2005 |
| WO | WO 03/075929 | A1 | 9/2003 | WO | WO 2005/063754 | A1 | 7/2005 |
| WO | WO 03/076395 | A1 | 9/2003 | WO | WO 2005/115983 | A1 | 12/2005 |
| WO | WO 03/076400 | A1 | 9/2003 | WO | WO 2006/009734 | A1 | 1/2006 |

| | | |
|---|---|---|
| WO | WO 2006/014168 A1 | 2/2006 |
| WO | WO 2006/033943 A2 | 3/2006 |
| WO | WO 2006/034279 A1 | 3/2006 |
| WO | WO 2006/034312 A1 | 3/2006 |
| WO | WO 2006/034315 A2 | 3/2006 |
| WO | WO 2006/034338 A1 | 3/2006 |
| WO | WO 2006/034341 A2 | 3/2006 |
| WO | WO 2006/034441 A1 | 3/2006 |
| WO | WO 2006/034446 A2 | 3/2006 |
| WO | WO 2006/034440 A2 | 5/2006 |
| WO | WO 2006/072436 A1 | 7/2006 |
| WO | WO 2006/101521 A2 | 9/2006 |
| WO | WO 2006/106423 A2 | 10/2006 |
| WO | WO 2006/130986 A1 | 12/2006 |
| WO | WO 2007/130075 A1 | 11/2007 |

OTHER PUBLICATIONS

Kuznetsov et al., CAPLUS Accession No. 111861-11-1, 1987, 1 page; see also, Kuznetsov et al., "Derivatives of 5(6)-Aminobenzimidazole," *Zhurnal Organicheskoi Khimii* 23(3): 637-642, Mar. 1987.

Latt and Stetten, "Spectral Studies on 33258 Hoechst and Related Bisbenzimidazole Dyes Useful for Fluorescent Detection of Deoxyribonucleic Acid Synthesis," *The Journal of Histochemistry and Cytochemistry* 24(1): 24-33, 1976.

Loewe and Urbanietz, CAPLUS Accession No. 23470-26-0, 1974, 3 pages; see also, Loewe and Urbanietz, "Basic substituted 2,6-bisbenzimidazole derivatives, a novel series of substances with chemotherapeutic activity," *Arzneimittel-Forschung* 24(12): 1927-1933, 1974.

Okamoto et al., "Novel ORL1-selective antagonists with oral bioavailability and brain penetrability," *Bioorganic & Medicinal Chemistry Letters* 18: 3282-3285, 2008.

Pan and Sun, "Soluble Polymer-Supported Synthesis of Arylpiperazines," *Tetrahedron Letters* 39: 9505-9508, 1998.

Sánchez-Alonso et al., "Piperazine derivatives of benzimidazole as potential anthelmintics," *Pharmazie* 44(9): 606-607, 1989.

Stoehr and Vogt-Schaden, CAPLUS Accession No. 23617-78-9, 1981, 1 page; see also, Stöhr and Vogt-Schaden, "A New Dual Staining Technique for Simultaneous Flow Cytometric DNA Analysis of Living and Dead Cells," *Flow Cytometry IV* 274: 9699, 1980.

Abuzar et al., "Synthesis of 2-Carbalkoxyamino-5(6)-(1-substituted piperazin-4-yl/piperazin-4-ylcarbonyl)benzimidazoles and Related Compounds as Potential Anthelmintics," *Pharmazie* 39(H. 11): 747-749, 1984.

Attie et al., "Relationship between stearoyl-CoA desaturase activity and plasma triglycerides in human and mouse hypertriglyceridemia," *Journal of Lipid Research* 43: 1899-1907, 2002.

Boissier et al., "Synthesis and Pharmacological Study of New Piperazine Derivatives. I. Benzylpiperazines," *Journal of Medicinal Chemistry* 6 541-544, Sep. 1963.

Charles River Laboratories, "ZDF Rat," URL=http://www.criver.com/research_models_and_services/research_models/ZDF.html, download date Mar. 17, 2008.

Cohen et al., "Role for Stearoyl-CoA Desaturase-1 in Leptin-Mediated Weight Loss," *Science* 297: 240-243, Jul. 12, 2002.

Cohen et al., "Stearoyl-CoA Desaturase-1 and the Metabolic Syndrome," *Current Drug Targets: Immune, Endocrine and Metabolic Disorders* 3(4): 271-280, 2003.

de Antueno et al., "Relationship Between Mouse Liver 9 Desaturase Activity and Plasma Lipids," *Lipids* 28(4): 285-290, 1993.

Diot et al., "Stearoyl-CoA Desaturase 1 Coding Sequences and Antisense RNA Affect Lipid Secretion in Transfected Chicken LMH Hepatoma Cells," *Archives of Biochemistry and Biophysics* 380(2): 243-250, Aug. 15, 2000.

Dobrzyn and Ntambi, "Stearoyl-CoA desaturase as a new drug target for obesity treatment," *Obesity Reviews* 6: 169-174, 2005.

Dobrzyn and Ntambi, "Stearoyl-CoA desaturase: A Therapeutic target of insulin resistance and diabetes," *Drug Discovery Today: Therapeutic Strategies* 2(2): 125-128, 2005.

Dubey et al., "Synthesis and Anthelmintic Activity of 5(6)-(Benzimidazol-2-ylcarbamoyl) and (4-Substituted piperazine-1-yl)benzimidazoles," *J. of Medicinal Chemistry* 28(11): 1748-1750, 1985.

Durrington et al., Embase No. 1978142387, 1978, 1 page; see also Durrington et al., "The effect of a low-cholesterol, high-polyunsaturate diet on serum lipid levels, apolipoprotein B levels and triglyceride fatty acid composition," *Atherosclerosis* 27: 465-475, 1977.

Enser, "Desaturation of Stearic Acid by Liver and Adipose Tissue from Obese-Hyperglycaemic Mice (*ob/ob*)," *Biochem. J.* 148: 551-555, 1975.

Flowers et al., "Probing the role of stearoyl-CoA desaturase-1 in hepatic insulin resistance," *The Journal of Clinical Investigation* 116(6): 1478-1481, Jun. 2006.

Foroumadi et al., "Synthesis and evaluation of in vitro antimycobacterial activity of some 5-(5-Nitro-2-thienyl)-2-(piperazinyl, piperidinyl and morpholinyl)-1,3,4-thiadiazole derivatives," *Boll. Chim. Farmac.* 142(9): 416-419, Nov. 2003.

Ghibaudi et al., "Fat Intake Affects Adiposity, Comorbidity Factors, and Energy Metabolism of Sprague-Dawley Rats," *Obesity Research* 10(9): 956-963, Sep. 2002.

Gooβen and Ghosh, "Palladium-Catalyzed Synthesis of Aryl Ketones from Boronic Acids and Carboxylic Acids Activated in situ by Pivalic Anhydride", *Eur. J. Org. Chem.*: 3254-3267, 2002.

Gotor et al., "Fungal and Bacterial Regioselective Hydroxylation of Pyrimidine Heterocycles," *Tetrahedron* 53(18): 6421-6432, 1997.

Grundy et al., "Diagnosis and Management of the Metabolic Syndrome: An American Heart Association/National Heart, Lung, and Blood Institute—Scientific Statement—Executive Summary," *Cardiology in Review* 13(6): 322-327, Nov./Dec. 2005.

Gutiérrez-Juárez, "Critical role of stearoyl-CoA desaturas-1 (SCD1) in the onset of diet-induced hepatic insulin resistance," *The Journal of Clinical Investigation* 116(6): 1686-1695, Jun. 2006.

Hori et al., "Studies on Antitumor-active 2,3-Dioxopiperazine Derivatives. III. Synthesis and Structure-Antitumor Activity Relationship of 1-(4-Aminobenzyl)-2,3-dioxopiperazine Derivatives," *Chem. Pharm. Bull* 29(5): 1253-1266, 1981.

Jacobsen et al., "2-(Aminomethyl)chromans that Inhibit Iron-Dependent Lipid Peroxidation and Protect against Central Nervous System Trauma and Ischemia," *Journal of Medicinal Chemistry* 35(23): 4464-4472, 1992.

Jacobsen et al., "Novel 21-Aminosteroids That Inhibit Iron-Dependent Lipid Peroxidation and Protect against Central Nervous System Trauma," *J. Med. Chem.* 33(4): 1145-1151, 1990.

Jeffcoat and James, *New Comprehensive Biochemistry vol. 7: Fatty Acid Metabolism and Its Regulation*, Elsevier Science Publishers B.V., Amsterdam, The Netherlands, Chapter 4, "The regulation of desaturation and elongation of fatty acids in mammals," 85-112, 1984.

Jeffcoat et al., "Stearoyl-CoA Desaturase: A Control Enzyme in Hepatic Lipogenesis," *Eur. J. Biochem* 101: 439-445, 1979.

Kim et al., "ARC POMC mRNA and PVN α-MSH are lower in obese relative to lean Zucker rats," *Brain Research* 862: 11-16, 2000.

Kirkeby et al., Medline PMID No. 596247, 1977, 1 page; see also, Kirkeby et al., "Effects of Prolonged, Strenuous Exercise on Lipids and Thyroxine in Serum," *Acta Med. Scand.* 202: 463-467, 1977.

Kurtz et al., "The Zucker Fatty Rat as a Genetic Model of Obesity and Hypertension," *Hypertension* 13(6, Part 2): 896-901, Jun. 1989.

Lee et al., "β-Cell lipotoxicity in the pathogenesis of non-insulin-dependent diabetes mellitus of obese rats: Impairment in adipocyte-β-cell relationships," *Proc. Natl. Acad. Sci. USA* 91: 10878-10882, Nov. 1994.

Lefevre et al., "Effects of Polyunsaturated Fatty Acids and Clofibrate on Chicken Stearoyl-CoA Desaturase 1 Gene Expression," *Biochemical and Biophysical Research Communications* 280(1): 25-31, 2001.

Lin et al., "CNS melanocortin and leptin effects on stearoyl-CoA desaturase-1 and resistin expression," *Biochemical and Biophysical Research Communications* 311: 324-328, 2003.

Luo et al., CAPLUS Accession No. 1999:55733, Registry No. 130:332501, 1999, 1 page.

Miyazaki et al, "The Biosynthesis of Hepatic Cholesterol Esters and Triglycerides is Impaired in Mice with a Disruption of the Gene for Stearoyl-CoA Desaturase 1," *The Journal of Biological Chemistry* 275(39): 30132-30138, Sep. 29, 2000.

Miyazaki et al., "A lipogenic diet in mice with a disruption of the stearoyl-CoA desaturase 1 gene reveals a stringent requirement of endogenous monounsaturated fatty acids for triglyceride synthesis," *J. Lipid Res.* 42: 1018-1024, 2001.

Miyazaki et al., "Targeted Disruption of Stearoyl-CoA Desaturase 1 Gene in Mice Causes Atrophy of Sebaceous and Meibomian Glands and Depletion of Wax Esters in the Eyelid," *J. Nutrition* 131: 2260-2268, 2001.

Ntambi et al., "Loss of stearoyl-CoA desaturase-1 function protects mice against adiposity," *Proc. Natl. Acad. Sci. USA* 99(17): 11482-11486, Aug. 20, 2002.

Ntambi, "Regulation of stearoyl-CoA desaturase by polyunsaturated fatty acids and cholesterol," *Journal of Lipid Research* 40: 1549-1558, 1999.

Ohashi, Biosis No. 198069026634, 1980, 1 page; see also, Ohashi, "Changes in cholesterol content and fatty acid composition of serum lipid in irradiated rat," *Okayama Igakkai Zasshi* 91(1-2): 241-249, 1979.

Ohkubo et al., "Studies on Cerebral Protective Agents. VIII. Synthesis of 2-Aminothiazoles and 2-Thiazolecarboxamides with Antianoxic Activity," *Chem. Pharm. Bull.* 43(9): 1497-1504, 1995.

Park et al., "Lipid Level and Type Alter Stearoyl CoA Desaturase mRNA Abundance Differently in Mice with Distinct Susceptibilities to Diet-Influenced Diseases," *J. Nutrition* 566-573, 1997.

Patel and Rybczynski, "Treatment of non-insulin-dependent diabetes mellitus," *Expert Opin. Investig. Drugs* 12(4): 623-633, 2003.

Ratouis et al., "Synthesis and Pharmacological Study of New Piperazine Derivatives. II. Phenethylpiperazines," *Journal of Medicinal Chemistry* 8: 104-107, Jan. 1965.

Ravina et al., Abstract Database CAPLUS on STN, Accession No. 1994:54512, 1994, 3 pages; see also Ravina et al., "Synthesis and Potential Anthelmintic Activity of Methyl-5-(4-salicyloyl-piperazin-1-yl)-benzimidazole-2-carbamates," *Arzneim.—Forsch./Drug Res.* 43(1-6): 689-694, 1993.

Rowley et al., "4-Heterocyclylpiperidines as Selective High-Affinity Ligands at the Human Dopamine D4 Receptor," *J. Med. Chem.* 40(15): 2374-2385, 1997.

Shanklin and Somerville, "Stearoyl-acyl-carrier-protein desaturase from higher plants is structurally unrelated to the animal and fungal homologs," *Proc. Natl. Acad. Sci. USA* 88: 2510-2514, Mar. 1991.

Shanklin et al., "Eight Histidine Residues Are Catalytically Essential in a Membrane-Associated Iron Enzyme, Stearoyl-CoA Desaturase, and Are Conserved in Alkane Hydroxylase and Xylene Monooxygenase," *Biochemistry* 33(43): 12787-12794, 1994.

Simopoulos, "Essential fatty acids in health and chronic disease," *Am. J. Clin. Nutr.* 70(suppl): 560S-569S, 1999.

Singh and Ram., "New Local Anaesthetics," *The Indian Journal of Pharmacy* 34(3): 74-76, Mar. 1972.

Sjögren et al., "Fatty acid desaturases in human adipose tissue: relationships between gene expression, desaturation indexes and insulin resistance," *Diabetologia* 51: 328-335, 2008.

Steck and Fletcher, "Pyridazines. VII. Some 3-Dialkylaminopyridazines (1)," *Journal of Heterocyc. Chem.* 11: 1077-1079, Dec. 1974.

Talamo and Bloch, "A New Assay for Fatty Acid Desaturation," *Analytical Biochemistry* 29: 300-304, 1969.

Thunus, Caplus on STN, Accession No. 1977:601475, 1977, 5 pages; see also, "Synthèse et propriétés pharmacologiques de quelques isopropyl et hydroxyéthylpipérazinylpyridines (substitution 2,5)," *Annales pharmaceutiques françaises* 35(5-6): 197-203, 1977.

Toldy et al., CAPLUS on STN, Accession No. 1967:473577, 1967, 3 pages; see also, Toldy et al., Piperazinderivative, II: Chlorobenzoxamin-Analoga, *Acta Chimica Acad. Sci. Hung. Tomus* 52(3): 283-299, 1967.

Toldy et al., CAPLUS on STN, Accession No. 1968:95776, 1968, 3 pages; see also, Toldy et al., "Phenthiazinderivate, VII: Versuche zur darstellung von selektiv wirkenden phenthiazinderivaten," *Acta Chimica Academiae Scientiarum Hungaricae Tomus* 53(3): 279-294, 1967.

Truett et al., "Rat obesity gene fatty (fa) maps to chromosome 5: Evidence for homology with the mouse gene diabetes (db)," *Proc. Natl. Acad. Sci USA* 88: 7806-7809, Sep. 1991.

Vice et al., "Concise Formation of 4-Benzyl Piperidines and Related Derivatives Using a Suzuki Protocol," *J. Org. Chem.* 66: 2487-2492, 2001.

Warensjöet al., "Polymorphisms in the *SCD1* Gene: Associations With Body Fat Distribution and Insulin Sensitivity," *Obesity* 15(7): 1732-1740, Jul. 2007.

White and Martin., CAPLUS Accession No. 1997:218911, 1997, 1 page; see also, White and Martin, "Evidence for a Central Mechanism of Obesity in the Zucker Rat: Role of Neuropeptide Y and Leptin," *P.S.E.B.M.* 214: 222-232, 1997.

Wityak et al., "Discovery and Initial SAR of 2-Amino-5-carboxamidothiazoles as Inhibitors of the Src-family Kinase p56$^{Lck}$," *Bioorg. Med. Chem. Lett.* 13: 4007-4010, 2003.

Wolfe et al., "Simple, Efficient Catalyst System for the Palladium-Catalyzed Amination of Aryl Chlorides, Bromides, and Triflates," *J. Org. Chem.* 65(4): 1158-1174, 2000.

Xin et al., "Discovery of piperidine-aryl urea-based stearoyl-CoA desaturase 1 inhibitors," *Bioorganic & Medicinal Chemistry Letters* 18: 4298-4302, 2008.

Zhang et al., "Down-regulation of the Expression of the Obese Gene by an Antidiabetic Thiazolidinedione in Zucker Diabetic Fatty Rats and db/db Mice," *The Journal of Biological Chemistry* 271(16): 9455-9459, Apr. 19, 1996.

Zheng et al., "*Scd1* is expressed in sebaceous glands and is disrupted in the asebia mouse," *Nature Genetics* 23: 268-270, Nov. 1999.

CAS Registry No. 504430-63-1, "3-Pyridinecarboxamide, 6-[4-[(2,2-dichloro-1-methylcyclopropyl)carbonyl]-1-piperazinyl]-N-[3-(diethylamino)propyl]-(9CI)", Apr. 24, 2003, 2 pages.

CAS Registry No. 362000-30-4, Oct. 14, 2001, "3-Pyridinecarboxamide, 6-[4-[(2,2-dichloro-1-methylcyclopropyl)carbonyl]-1-piperazinyl]-N-[3-(methylthio)propyl]-(9CI)", Oct. 14, 2001, 2 pages.

International Search Report and Written Opinion, mailed Oct. 26, 2006, for PCTAN PCT/US2006/021660, 15 pages.

International Preliminary Report on Patentability, mailed Dec. 17, 2007, for PCTAN PCT/US2006/021660, 9 pages.

Official Action from State Intellectual Property Office of China, dated Dec. 11, 2009, for Patent Application No. 200680019628.X, 4 pages.

Official Action from European Patent Office, dated Aug. 13, 2010, for Patent Application No. 06 784 578.4, 3 pages.

Translation of Official Action from Patent Office of Japan, dated Feb. 14, 2012, for Patent Application No. 2008-525998, 10 pages.

Isabel et al., "Biological activity and preclinical efficacy of azetidinyl pyridazines as potent systemically-distributed stearoyl-CoA desaturase inhibitors," *Bioorganic & Medicinal Chemistry Letters* 21: 479-483, 2011.

Liu, "Stearoyl-CoA desaturase inhibitors: update on patented compounds," *Expert Opin. Ther. Patents* 19(9): 1169-1191, 2009.

Liu et al., "Discovery of Potent, Selective, Orally Bioavailable Stearoyl-CoA Desaturase 1 Inhibitors," *J. Med. Chem.* 50(13): 3086-3100, 2007.

Robert et al., "Synthesis and antileishmanil activity of new imidazolidin-2-one derivatives," *European Journal of Medicinal Chemistry* 38: 711-718, 2003.

Tucker et al., "Piperazinyl Oxazolidinone Antibacterial Agents Containing a Pyridine, Diazene, or Triazene Heteroaromatic Ring," *J. Med. Chem.* 41(19): 3727-3735, 1998.

Official Action from European Patent Office re extended European search report, dated Dec. 5, 2012, for Patent Application No. 12005821.9, 8 pages.

\* cited by examiner

AMINOTHIAZOLE DERIVATIVES AS HUMAN STEAROYL-COA DESATURASE INHIBITORS

CROSS-REFERENCES TO RELATED APPLICATIONS

This application is a U.S. National Phase Application of International Application No. PCT/US06/021660, filed Jun. 5, 2006; which claims priority to U.S. Provisional Patent Application No. 60/687,133, filed Jun. 3, 2005. All of these applications are incorporated herein by reference in their entireties.

FIELD OF THE INVENTION

The present invention relates generally to the field of inhibitors of stearoyl-CoA desaturase, such as aminothiazole derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome, dermatological disorders and the like.

BACKGROUND OF THE INVENTION

Acyl desaturase enzymes catalyze the formation of double bonds in fatty acids derived from either dietary sources or de novo synthesis in the liver. In mammals, at least three fatty acid desaturases exist, each with differing specificity: delta-9, delta-6, and delta-5, which introduce a double bond at the 9-10, 6-7, and 5-6 positions respectively.

Stearoyl-CoA desaturases (SCDs) act with cofactors (other agents), such as NADPH, cytochrome b5, cytochrome b5 reductase, Fe, and molecular $O_2$, to introduce a double bond into the C9-C10 position (delta 9) of saturated fatty acids, when conjugated to Coenzyme A (CoA). The preferred substrates are palmitoyl-CoA (16:0) and stearoyl-CoA (18:0), which are converted to palmitoleoyl-CoA (16:1) and oleyl-CoA (18:1), respectively. The resulting mono-unsaturated fatty acids are substrates for further metabolism by fatty acid elongases or incorporation into phospholipids, triglycerides, and cholesterol esters. A number of mammalian SCD genes have been cloned. For example, two genes have been identified in humans (hSCD1 and hSCD5) and four SCD genes have been isolated from mouse (SCD1, SCD2, SCD3, and SCD4). While the basic biochemical role of SCD has been known in rats and mice since the 1970's (Jeffcoat, R. et al., *Eur. J. Biochem.* (1979), Vol. 101, No. 2, pp. 439-445; de Antueno, R. et al. *Lipids* (1993), Vol. 28, No. 4, pp. 285-290), it has only recently been directly implicated in human disease processes.

The two human SCD genes have been previously described: hSCD1 by Brownlie et al., PCT Published Patent Application, WO 01/62954, the disclosure of which is hereby incorporated by reference in its entirety and hSCD2, PCT Published Patent Application, WO 02/26944, incorporated herein by reference in its entirety.

To date, the only small molecule compounds known that specifically inhibit or modulate SCD activity are found in the following PCT Published Patent Applications: WO/2006034338A1, WO/2006034446A2, WO/2006034441A1, WO/2006034440A2, WO/2006034341A2, WO/2006034315A2, WO/2006034312A1, WO/2006034279A1, WO/2006014168A1, WO/2005011657A2, WO/2005011656A2, WO/2005011655A2, WO/2005011654A2 and WO/2005011653A2. Before the disclosure of the compounds in the foregoing PCT Published Patent Applications, only certain long-chain hydrocarbons, analogs of the substrate stearic acid, had been used to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA while cis-9, trans-11 conjugated linoleic acid does not. Cyclopropenoid fatty acids, such as those found in stercula and cotton seeds, are also known to inhibit SCD activity. For example, sterculic acid (8-(2-octylcyclopropenyl)octanoic acid) and malvalic acid (7-(2-octylcyclopropenyl)heptanoic acid) are C18 and C16 derivatives of sterculoyl and malvaloyl fatty acids, respectively, having cyclopropene rings at their C9-C10 position. These agents must be coupled to CoA to act as inhibitors and are believed to inhibit SCD enzymatic activity by direct interaction with the enzyme, thus inhibiting delta-9 desaturation. Other agents that may inhibit SCD activity include thia-fatty acids, such as 9-thiastearic acid (also called 8-nonylthiooctanoic acid) and other fatty acids with a sulfoxy moiety.

There is still a major unmet need for small molecule inhibitors of SCD enzyme activity because evidence is now compelling that SCD activity is directly implicated in common human disease processes; see, e.g., Attie, A. D. et al., "Relationship between stearoyl-CoA desaturase activity and plasma triglycerides in human and mouse hypertriglyceridemia", *J. Lipid Res.* (2002), Vol. 43, No. 11, pp. 1899-907; Cohen, P. et al., "Role for stearoyl-CoA desaturase-1 in leptin mediated weight loss", *Science* (2002), Vol. 297, No. 5579, pp. 240-3; and Ntambi, J. M. et al., "Loss of stearoyl-CoA desaturase-1 function protects mice against adiposity", *Proc. Natl. Acad. Sci. U.S.A.* (2002), Vol. 99, No. 7, pp. 11482-6.

The present invention solves this problem by presenting new classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

SUMMARY OF THE INVENTION

The present invention provides aminothiazole derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect this invention provides a method of inhibiting human stearoyl-CoA desaturase (hSCD) activity wherein the method comprises contacting a source of hSCD with a compound of formula (I):

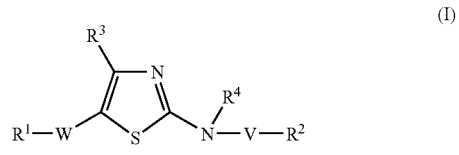

wherein:

W is selected from —O—, —OC(O)—, —OC(O)N(R⁵)—, —OS(O)₂N(R⁵)—, —C(O)—, —C(O)O—, —C(O)N(R⁵)—, —N(R⁵)—, —N(R⁵)C(O)—, —N(R⁵)C(O)O—, —N(R⁵)C(O)N(R⁵)—, —N(R⁵)S(O)₂—, —S(O)$_t$— (where t is 0, 1 or 2), or —S(O)₂N(R⁵)—;

V is selected from —C(O)—, —C(O)N(R⁵)—, —C(O)O—, —S(O)$_t$— (where t is 1 or 2) or a direct bond;

R¹ is selected from the group consisting of alkyl, alkenyl, —R⁶—OR⁷, hydroxyalkenyl, cycloalkyl, cycloalkylalkyl, aryl, aralkyl, aralkenyl, heterocyclyl, heterocyclylalkyl, heteroaryl, and heteroarylalkyl;

or R¹ is a multi-ring structure having 2 to 4 rings wherein the rings are independently selected from the group consisting of cycloalkyl, heterocyclyl, aryl and heteroaryl and where some or all of the rings may be fused to each other;

R² is selected from the group consisting of alkyl, alkenyl, —R⁶—OR⁷, hydroxyalkenyl, cycloalkyl, cycloalkylalkyl, aryl, aralkyl, aralkenyl, heterocyclyl, heterocyclylalkyl, heteroaryl and heteroarylalkyl;

or R² is a multi-ring structure having 2 to 4 rings wherein the rings are independently selected from the group consisting of cycloalkyl, heterocyclyl, aryl and heteroaryl and where some or all of the rings may be fused to each other;

R³ is selected from hydrogen, alkyl, alkenyl, hydroxyalkyl, hydroxyalkenyl, alkoxyalkyl, cycloalkyl, cycloalkylalkyl, heterocyclyl, aryl, aralkyl, heteroaryl, fluoro, chloro, bromo, trihaloalkyl, trihaloalkoxy, cyano, nitro, —OR⁴, —OC(O)R², —OC(O)N(R⁴)(R⁵), —OS(O)₂N(R⁴)(R⁵), —S(O)$_t$R² (where t is 0, 1 or 2), —S(O)$_t$N(R⁴)(R⁵) (where t is 1 or 2), —C(O)R², —C(O)OR², —C(O)N(R⁴)(R⁵), —N(R⁴)(R⁵), —N(R⁵)C(O)R⁵, —N(R⁵)C(O)OR⁵, —N(R⁵)C(O)N(R⁴)(R⁵) or —N(R⁵)S(O)₂R²;

each R⁴ and R⁵ is independently selected from the group consisting of —R⁶—N(R⁷)₂, —R⁶—OR⁷, —R⁶—C(O)OR⁷, hydrogen, alkyl, cycloalkylalkyl and aralkyl;

each R⁶ is a straight or branched alkylene chain; and each R⁷ is hydrogen, alkyl, aryl or aralkyl;

or a stereoisomer, enantiomer or tautomer thereof, or a racemic or non-racemic mixture thereof, or a pharmaceutically acceptable salt or prodrug thereof.

In another aspect, the invention provides methods of treating an SCD-mediated disease or condition in a mammal, preferably a human, wherein the methods comprise administering to the mammal in need thereof a therapeutically effective amount of a compound of formula (I) as set forth above.

In another aspect, the invention provides compounds of formula (I) or pharmaceutical compositions comprising compounds of formula (I) that are useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a compound of formula (I) or a pharmaceutical composition comprising a compound of formula (I) as disclosed herein. The present invention also relates to compounds having therapeutic ability to reduce lipid levels in an animal, especially triglyceride and cholesterol levels.

In another aspect, the invention provides pharmaceutical compositions comprising the compounds of formula (I) as set forth above, and pharmaceutically acceptable excipients. In one embodiment, the present invention relates to a pharmaceutical composition comprising a compound of formula (I) in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound of formula (I) that inhibits activity of SCD in a patient when administered thereto.

In another aspect, the invention provides methods for treating a range of diseases involving lipid metabolism utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

In another aspect is the use of the pharmaceutical composition as described above for production of a medicament for the treatment of SCD-mediated disease or conditions.

In another aspect is the use of a pharmaceutical composition or combination as described above for the preparation of a medicament for the treatment of conditions associated with stearoyl-CoA desatruase activity.

In another aspect, is a pharmaceutical composition as described above for the treatment of conditions associated with the inhibition of stearoyl-CoA desaturase.

DETAILED DESCRIPTION OF THE INVENTION

Definitions

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of seven to twelve carbon atoms, and $C_4$-$C_{12}$cycloalkylalkyl describes a cycloalkylalkyl group, as defined below, having a total of four to twelve carbon atoms. The total number of carbons in the shorthand notation does not include carbons that may exist in substituents of the group described.

Accordingly, as used in the specification and appended claims, unless specified to the contrary, the following terms have the meaning indicated:

"Methoxy" refers to the —OCH₃ radical.

"Cyano" refers to the —CN radical.

"Nitro" refers to the —NO₂ radical.

"Trifluoromethyl" refers to the —CF₃ radical.

"Oxo" refers to the =O substituent.

"Thioxo" refers to the =S substituent.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})S(O)_tR^{16}$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each IV is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"$C_1$-$C_3$alkyl" refers to an alkyl radical as defined above containing one to three carbon atoms. The $C_1$-$C_3$alkyl radical may be optionally substituted as defined for an alkyl group.

"$C_1$-$C_6$alkyl" refers to an alkyl radical as defined above containing one to six carbon atoms. The $C_1$-$C_6$alkyl radical may be optionally substituted as defined for an alkyl group.

"$C_1$-$C_{12}$alkyl" refers to an alkyl radical as defined above containing one to twelve carbon atoms. The $C_1$-$C_{12}$alkyl radical may be optionally substituted as defined for an alkyl group.

"$C_2$-$C_6$alkyl" refers to an alkyl radical as defined above containing two to six carbon atoms. The $C_2$-$C_6$alkyl radical may be optionally substituted as defined for an alkyl group.

"$C_3$-$C_6$alkyl" refers to an alkyl radical as defined above containing three to six carbon atoms. The $C_3$-$C_6$alkyl radical may be optionally substituted as defined for an alkyl group.

"$C_3$-$C_{12}$alkyl" refers to an alkyl radical as defined above containing three to twelve carbon atoms. The $C_3$-$C_{12}$alkyl radical may be optionally substituted as defined for an alkyl group.

"$C_6$-$C_{12}$alkyl" refers to an alkyl radical as defined above containing six to twelve carbon atoms. The $C_6$-$C_{12}$alkyl radical may be optionally substituted as defined for an alkyl group.

"$C_7$-$C_{12}$alkyl" refers to an alkyl radical as defined above containing seven to twelve carbon atoms. The $C_7$-$C_{12}$alkyl radical may be optionally substituted as defined for an alkyl group.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})S(O)_tR^{16}$) (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$alkenyl" refers to an alkenyl radical as defined above containing three to twelve carbon atoms. The $C_3$-$C_{12}$alkenyl radical may be optionally substituted as defined for an alkenyl group.

"$C_2$-$C_{12}$alkenyl" refers to an alkenyl radical as defined above containing two to twelve carbon atoms. The $C_2$-$C_{12}$alkenyl radical may be optionally substituted as defined above for an alkenyl group.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkylene bridge" refers to a straight or branched divalent hydrocarbon bridge, linking two different carbons of the same ring structure, or linking one carbon of a substituent of a ring structure with a carbon in the ring structure, consisting solely of carbon and hydrogen, containing no unsaturation and having from one to twelve carbon atoms, preferably having from one to eight carbons, e.g., methylene, ethylene, propylene, n-butylene, and the like. The alkylene bridge may link any two carbons within the ring structure.

"Alkoxy" refers to a radical of the formula —$OR_a$, where $R_a$ is an alkyl radical as defined above. The alkyl part of the alkoxy radical may be optionally substituted as defined above for an alkyl radical.

"$C_1$-$C_6$alkoxy" refers to an alkoxy radical as defined above containing one to six carbon atoms. The alkyl part of the $C_1$-$C_6$alkoxy radical may be optionally substituted as defined above for an alkyl group.

"$C_1$-$C_{12}$alkoxy" refers to an alkoxy radical as defined above containing one to twelve carbon atoms. The alkyl part of the $C_1$-$C_{12}$alkoxy radical may be optionally substituted as defined above for an alkyl group.

"$C_3$-$C_{12}$alkoxy" refers to an alkoxy radical as defined above containing three to twelve carbon atoms. The alkyl part of the $C_3$-$C_{12}$alkoxy radical may be optionally substituted as defined above for an alkyl group.

"Alkoxyalkyl" refers to a radical of the formula —$R_a$—O—$R_a$, where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"$C_2$-$C_{12}$alkoxyalkyl" refers to an alkoxyalkyl radical as defined above containing two to twelve carbon atoms. Each alkyl part of the $C_2$-$C_{12}$alkoxyalkyl radical may be optionally substituted as defined above for an alkyl group.

"$C_3$alkoxyalkyl" refers to an alkoxyalkyl radical as defined above containing three carbon atoms. Each alkyl part of the $C_3$alkoxyalkyl radical may be optionally substituted as defined above for an alkyl group.

"$C_3$-$C_{12}$alkoxyalkyl" refers to an alkoxyalkyl radical as defined above containing three to twelve carbon atoms. Each alkyl part of the $C_3$-$C_{12}$alkoxyalkyl radical may be optionally substituted as defined above for an alkyl group.

"Alkylsulfonyl" refers to a radical of the formula —S(O)$_2$R$_a$ where R$_a$ is an alkyl group as defined above. The alkyl part of the alkylsulfonyl radical may be optionally substituted as defined above for an alkyl group.

"$C_1$-$C_6$alkylsulfonyl" refers to an alkylsulfonyl radical as defined above having one to six carbon atoms. The $C_1$-$C_6$alkylsulfonyl group may be optionally substituted as defined above for an alkylsulfonyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, ..R$^{15}$—N(R$^{14}$)C(O)R$^{16}$, —R$^{15}$—S(O)$_t$R$^{16}$ (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{16}$—S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"$C_7$-$C_{12}$aralkyl" refers to an aralkyl group as defined above containing seven to twelve carbon atoms. The aryl part of the $C_7$-$C_{12}$aralkyl radical may be optionally substituted as described above for an aryl group. The alkyl part of the $C_7$-$C_{12}$aralkyl radical may be optionally substituted as defined above for an alkyl group.

"$C_{13}$-$C_{19}$aralkyl" refers to an aralkyl group as defined above containing thirteen to nineteen carbon atoms. The aryl part of the $C_{13}$-$C_{19}$aralkyl radical may be optionally substituted as described above for an aryl group. The alkyl part of the $C_{13}$-$C_{19}$aralkyl radical may be optionally substituted as defined above for an alkyl group.

"Aralkenyl" refers to a radical of the formula —R$_c$R$_b$ where R$_c$ is an alkenyl radical as defined above and R$_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aryloxy" refers to a radical of the formula —OR$_b$ where R$_b$ is an aryl group as defined above. The aryl part of the aryloxy radical may be optionally substituted as defined above.

"Aryl-$C_1$-$C_6$alkyl" refers to a radical of the formula —R$_h$—R$_i$, where R$_h$ is an unbranched alkyl radical having one to six carbons and R$_i$ is an aryl group attached to the terminal carbon of the alkyl radical.

"Cycloalkyl" refers to a stable non-aromatic monocyclic, bicyclic or tricyclic hydrocarbon radical consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{16}$—N(R$^{14}$)C(O)R$^{16}$, —R$^{15}$—N$^{14}$)S(O)$_t$R$^{16}$) (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{15}$—S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted. Examples of such cycloalkyl radicals include, but are not limited to, cyclopropyl, cyclobutyl, adamantyl, etc.

"$C_3$-$C_6$cycloalkyl" refers to a cycloalkyl radical as defined above having three to six carbon atoms. The $C_3$-$C_6$cycloalkyl radical may be optionally substituted as defined above for a cycloalkyl group.

"$C_3$-$C_{12}$cycloalkyl" refers to a cycloalkyl radical as defined above having three to twelve carbon atoms. The $C_3$-$C_{12}$cycloalkyl radical may be optionally substituted as defined above for a cycloalkyl group.

"Cycloalkylalkyl" refers to a radical of the formula —R$_a$R$_d$ where R$_a$ is an alkyl radical as defined above and R$_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"$C_4$-$C_{12}$cycloalkylalkyl" refers to a cycloalkylalkyl radical as defined above having four to twelve carbon atoms. The $C_4$-$C_{12}$cycloalkylalkyl radical may be optionally substituted as defined above for a cycloalkylalkyl group.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3-bromoprop-1-enyl, and the like. The alkenyl part of the haloalkenyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—$N(R^{14})_2$, —$R^{15}$—C(O)$R^{14}$, —$R^{15}$—C(O)$OR^{14}$, —$R^{15}$—C(O)N($R^{14})_2$, —$R^{15}$—N($R^{14}$)C(O)$OR^{16}$, —$R^{15}$—N($R^{14}$)C(O)$R^{16}$, —$R^{15}$—N($R^{14}$)S(O)$_tR^{16}$ (where t is 1 to 2), —$R^{15}$—S(O)$_tOR^{16}$ (where t is 1 to 2), —$R^{15}$—S(O)$_tR^{16}$ (where t is 0 to 2), and —$R^{15}$—S(O)$_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$heterocyclyl" refers to a heterocyclyl radical as defined above having three to twelve carbons. The $C_3$-$C_{12}$heterocyclyl may be optionally substituted as defined above for a heterocyclyl group.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"$C_3$-$C_{12}$heterocyclylalkyl" refers to a heterocyclylalkyl radical as defined above having three to twelve carbons. The $C_3$-$C_{12}$heterocyclylalkyl radical may be optionally substituted as defined above for a heterocyclylalkyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—$N(R^{14})_2$, —$R^{15}$—C(O)$R^{14}$, —$R^{15}$—C(O)$OR^{14}$, —$R^{15}$—C(O)N($R^{14})_2$, —$R^{15}$—N($R^{14}$)C(O)$OR^{16}$, —$R^{15}$—N($R^{14}$)C(O)$R^{16}$, —$R^{15}$—N($R^{14}$)S(O)$_tR^{16}$ (where t is 1 to 2), —$R^{15}$—S(O)$_tOR^{16}$ (where t is 1 to 2), —$R^{15}$—S(O)$_tR^{16}$ (where t is 0 to 2), and —$R^{15}$—S(O)$_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_1$-$C_{12}$heteroaryl" refers to a heteroaryl radical as defined above having one to twelve carbon atoms. The $C_1$-$C_{12}$heteroaryl group may be optionally substituted as defined above for a heteroaryl group.

"$C_5$-$C_{12}$heteroaryl" refers to a heteroaryl radical as defined above having five to twelve carbon atoms. The $C_5$-$C_{12}$heteroaryl group may be optionally substituted as defined above for a heteroaryl group.

"Heteroarylalkyl" refers to a radical of the formula —$R_aR_f$ where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"$C_3$-$C_{12}$heteroarylalkyl" refers to a heteroarylalkyl radical as defined above having three to twelve carbon atoms. The $C_3$-$C_{12}$heteroarylalkyl group may be optionally substituted as defined above for a heteroarylalkyl group.

"Heteroarylcycloalkyl" refers to a radical of the formula —$R_dR_f$ where $R_d$ is a cycloalkyl radical as defined above and $R_f$ is a heteroaryl radical as defined above. The cycloalkyl part of the heteroarylcycloalkyl radical may be optionally substituted as defined above for a cycloalkyl group. The heteroaryl part of the heteroarylcycloalkyl radical may be optionally substituted as defined above for a heteroaryl group.

"Heteroarylalkenyl" refers to a radical of the formula —$R_bR_f$ where $R_b$ is an alkenyl radical as defined above and $R_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"$C_2$-$C_{12}$hydroxyalkyl" refers to a hydroxyalkyl radical as defined above containing two to twelve carbon atoms. The alkyl part of the $C_2$-$C_{12}$hydroxyalkyl radical may be optionally substituted as defined above for an alkyl group.

"$C_3$-$C_{12}$hydroxyalkyl" refers to a hydroxyalkyl radical as defined above containing three to twelve carbon atoms. The alkyl part of the $C_3$-$C_{12}$hydroxyalkyl radical may be optionally substituted as defined above for an alkyl group.

"$C_7$-$C_{12}$hydroxyalkyl" refers to a hydroxyalkyl radical as defined above containing seven to twelve carbon atoms. The alkyl part of the $C_7$-$C_{12}$hydroxyalkyl radical may be optionally substituted as defined above for an alkyl group.

"Hydroxyalkenyl" refers to a radical of the formula —$R_c$—OH where $R_c$ is an alkenyl radical as defined above. The hydroxy group may be attached to the alkenyl radical on any carbon within the alkenyl radical. The alkenyl part of the hydroxyalkenyl group may be optionally substituted as defined above for an alkenyl group.

"$C_2$-$C_{12}$hydroxyalkenyl" refers to a hydroxyalkenyl radical as defined above containing two to twelve carbon atoms. The alkenyl part of the $C_2$-$C_{12}$hydroxyalkenyl radical may be optionally substituted as defined above for an alkenyl group.

"$C_3$-$C_{12}$hydroxyalkenyl" refers to a hydroxyalkenyl radical as defined above containing three to twelve carbon atoms. The alkenyl part of the $C_3$-$C_{12}$hydroxyalkenyl radical may be optionally substituted as defined above for an alkenyl group.

"Hydroxyl-$C_1$-$C_6$-alkyl" refers to a radical of the formula —$R_h$—OH where $R_h$ is an unbranched alkyl radical having one to six carbons and the hydroxy radical is attached to the terminal carbon.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"$C_1$-$C_6$-trihaloalkyl" refers to a trihaloalkyl radical as defined above having one to six carbon atoms. The $C_1$-$C_6$-trihaloalkyl may be optionally substituted as defined above for a trihaloalkyl group.

"Trihaloalkoxy" refers to a radical of the formula —$OR_g$ where $R_g$ is a trihaloalkyl group as defined above. The trihaloalkyl part of the trihaloalkoxy group may be optionally substituted as defined above for a trihaloalkyl group.

"$C_1$-$C_6$-trihaloalkoxy" refers to a trihaloalkoxy radical as defined above having one to six carbon atoms. The $C_1$-$C_6$-trihaloalkoxy group may be optionally substituted as defined above for a trihaloalkoxy group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to other through direct bonds or some or all of the rings may be fused to each other. Examples include, but are not limited to a cycloalkyl radical substituted by aryl group; and a cycloalkyl group substituted by an aryl group.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amides of amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein employ and rely on the chemical naming features as utilized by ChemDraw versions 7.0.1 and 10.0 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

For example, a compound of formula (I) wherein W is —N(H)C(O)—, V is —C(O)N(H)—, R$^1$ is benzyl, R$^2$ is 4-chlorophenyl, R$^3$ is methyl and R$^4$ is hydrogen, i.e., a compound of the following formula:

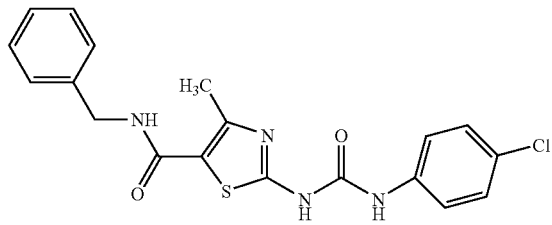 [SMILES: Cc1nc(NC(=O)Nc2ccc(Cl)cc2)sc1C(=O)NCc1ccccc1]

is named herein as 2-[3-(4-chlorophenyl)ureido]-4-methylthiazole-5-carboxylic acid benzylamide.

Certain radical groups of the compounds of the invention are depicted herein as linkages between two parts of the compounds of the invention. For example, in the following formula (I):

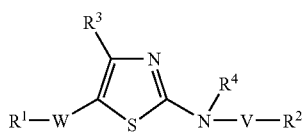

W is described, for example, as being —N(R$^5$)C(O)—; and V is described as —C(O)N(R$^5$)—. This description is meant to describe a W group attached to the R$^1$ group as follows: R$^1$—N(R$^5$)C(O)—; and meant to describe a V group attached to the R$^2$ group as follows: —C(O)N(R$^5$)—R$^2$. In other words, the descriptions of the W and V linkage groups are meant to be read from left to right in view of formula (I) as depicted above.

EMBODIMENTS OF THE INVENTION

In one embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome, dermatological disorders and the like by administering an effective amount of a compound of formula (I).

Accordingly, one embodiment of the invention is a method of treating a disease or condition mediated by stearoyl-CoA desaturase (SCD) in a mammal, wherein the method comprises administering to the mammal in need thereof a therapeutically effective amount of a compound of formula (I) wherein the mammal is a human.

Of this embodiment, another embodiment is wherein the disease or condition is selected from the group consisting of Type II diabetes, impaired glucose tolerance, insulin resistance, obesity, fatty liver, non-alcoholic steatohepatitis, dyslipidemia and metabolic syndrome, dermatological disorders and any combination of these.

Of this embodiment, one embodiment is wherein the disease or condition is Type II diabetes.

Of this embodiment, another embodiment is wherein the disease or condition is obesity.

Of this embodiment, another embodiment is wherein the disease or condition is metabolic syndrome.

Of this embodiment, another embodiment is wherein the disease or condition is fatty liver.

Of this embodiment, another embodiment is wherein the disease or condition is non-alcoholic steatohepatitis.

Of this embodiment, another embodiment is wherein the disease or condition is dermatological disorders. Of the embodiments disclosed above, one embodiment is wherein the compound of formula (I) is selected from the group consisting of the following:

2-(4-Bromobenzoylamino)-4-methylthiazole-5-carboxylic acid o-tolylamide;
2-(4-Bromobenzoylamino)-4-methylthiazole-5-carboxylic acid (2-chlorophenyl)amide;
2-(4-Bromobenzoylamino)-4-methylthiazole-5-carboxylic acid (3-methoxyphenyl)amide;
4-Methyl-2-(3,4,5-trimethoxybenzoylamino)thiazole-5-carboxylic acid phenylamide;
4-Methyl-2-(4-methylbenzoylamino)thiazole-5-carboxylic acid (4-methoxyphenyl)amide;
4-Methyl-2-[(thiophene-2-carbonyl)amino]thiazole-5-carboxylic acid (4-chlorophenyl)amide;
2-(Cyclohexanecarbonylamino)-4-methylthiazole-5-carboxylic acid (2,3-dihydro-benzo[1,4]dioxin-6-yl)amide;
2-(4-Methoxybenzoylamino)-4-methylthiazole-5-carboxylic acid pyridin-3-ylamide;
2-Benzoylamino-4-methylthiazole-5-carboxylic acid (5-methyl[1,3,4]thiadiazol-2-yl)amide;
2-[(Furan-2-carbonyl)amino]-4-methylthiazole-5-carboxylic acid o-tolylamide;
2-[(Furan-2-carbonyl)amino]-4-methylthiazole-5-carboxylic acid (4-bromophenyl)amide;
2-(3-Methoxybenzoylamino)-4-methylthiazole-5-carboxylic acid (4-bromophenyl)amide;
2-[(Furan-2-carbonyl)amino]-4-methylthiazole-5-carboxylic acid (4-chlorophenyl)amide;
2-[(Furan-2-carbonyl)amino]-4-methylthiazole-5-carboxylic acid (3-methoxyphenyl)amide;
2-[(Furan-2-carbonyl)amino]-4-methylthiazole-5-carboxylic acid (4-methoxyphenyl)amide;
4-Methyl-2-(2-phenoxyacetylamino)thiazole-5-carboxylic acid phenylamide;
4-Methyl-2-(2-phenoxyacetylamino)thiazole-5-carboxylic acid benzylamide;
2-Chloro-N-[4-methyl-5-(morpholine-4-carbonyl)thiazol-2-yl]benzamide;
2-(3-Fluorobenzoylamino)-4-methylthiazole-5-carboxylic acid (4-bromophenyl)amide;
2-(2-Fluorobenzoylamino)-4-methylthiazole-5-carboxylic acid (4-bromophenyl)amide;
2-Acetylamino-4-methylthiazole-5-carboxylic acid indan-5-ylamide;
2-Acetylamino-4-methylthiazole-5-carboxylic acid cyclohexylamide;
2-(4-Fluorobenzoylamino)-4-methylthiazole-5-carboxylic acid (4-bromophenyl)amide;
2-Benzoylamino-4-methylthiazole-5-carboxylic acid phenylamide;
2-Benzoylamino-4-methylthiazole-5-carboxylic acid (3-methoxyphenyl)amide;
2-(4-Fluorobenzoylamino)-4-methylthiazole-5-carboxylic acid (4-methoxyphenyl)amide;

4-Methyl-2-propionylaminothiazole-5-carboxylic acid indan-5-ylamide;
2-(Cyclopropanecarbonylamino)-4-methylthiazole-5-carboxylic acid phenylamide;
2-(Cyclopropanecarbonylamino)-4-methylthiazole-5-carboxylic acid (4-chlorophenyl)amide;
2-(4-Fluorobenzoylamino)-4-methylthiazole-5-carboxylic acid phenylamide;
2-(4-Fluorobenzoylamino)-4-methylthiazole-5-carboxylic acid o-tolylamide;
2-(4-Fluorobenzoylamino)-4-methylthiazole-5-carboxylic acid (4-chlorophenyl)amide;
2-(4-Fluorobenzoylamino)-4-methylthiazole-5-carboxylic acid (2-chlorophenyl)amide;
2-(4-Fluorobenzoylamino)-4-methylthiazole-5-carboxylic acid (3-methoxyphenyl)amide;
N-[4-Methyl-5-(piperidine-1-carbonyl)-thiazol-2-yl]benzamide;
2-(Cyclopropanecarbonylamino)-4-methylthiazole-5-carboxylic acid benzylamide;
2-(Cyclopropanecarbonylamino)-4-methylthiazole-5-carboxylic acid indan-5-ylamide;
4-Methyl-2-(4-methylbenzoylamino)thiazole-5-carboxylic acid pyridin-3-ylamide;
4-Methyl-2-propionylaminothiazole-5-carboxylic acid benzylamide;
[(2-Benzoylamino-4-methylthiazole-5-carbonyl)amino]acetic acid ethyl ester;
N-[4-Methyl-5-(morpholine-4-carbonyl)thiazol-2-yl]propionamide;
N-(5-Benzylcarbamoyl-4-methylthiazol-2-yl)isonicotinamide;
N-[5-(3-Chlorophenylcarbamoyl)-4-methylthiazol-2-yl]isonicotinamide;
N-[5-(2-Chlorophenylcarbamoyl)-4-methylthiazol-2-yl]isonicotinamide;
N-(4-Oxo-5,6,7,8-tetrahydro-4H-thiazolo[5,4-c]azepin-2-yl)acetamide;
N-(7,7-Dimethyl-4-oxo-5,6,7,8-tetrahydro-4H-thiazolo[5,4-c]azepin-2-yl)acetamide;
2-(3-Fluorobenzoylamino)-4-methylthiazole-5-carboxylic acid phenylamide;
4-Methyl-2-(4-methylbenzoylamino)thiazole-5-carboxylic acid o-tolylamide;
2-(2-Fluorobenzoylamino)-4-methylthiazole-5-carboxylic acid o-tolylamide;
2-(4-Bromobenzoylamino)-4-methylthiazole-5-carboxylic acid (4-chlorophenyl)amide;
4-Methyl-2-(3,4,5-trimethoxybenzoylamino)thiazole-5-carboxylic acid (4-chlorophenyl)amide;
2-(4-Bromobenzoylamino)-4-methylthiazole-5-carboxylic acid (3-chlorophenyl)amide;
4-Methyl-2-(3-methylbenzoylamino)thiazole-5-carboxylic acid (3-chlorophenyl)amide;
2-(3-Fluorobenzoylamino)-4-methylthiazole-5-carboxylic acid (3-chlorophenyl)amide;
4-Methyl-2-(2-methylbenzoylamino)thiazole-5-carboxylic acid (2-chlorophenyl)amide;
4-Methyl-2-(3,4,5-trimethoxybenzoylamino)thiazole-5-carboxylic acid (2-chlorophenyl)amide;
4-Methyl-2-(3-methylbenzoylamino)thiazole-5-carboxylic acid (2-chlorophenyl)amide;
2-(3-Fluorobenzoylamino)-4-methylthiazole-5-carboxylic acid (2-chlorophenyl)amide;
2-(4-Bromobenzoylamino)-4-methylthiazole-5-carboxylic acid (2,3-dihydro-benzo[1,4]dioxin-6-yl)amide;
2-(4-Methoxybenzoylamino)-4-methylthiazole-5-carboxylic acid (2,3-dihydro-benzo[1,4]dioxin-6-yl)amide;
4-Methyl-2-(3-methylbenzoylamino)thiazole-5-carboxylic acid (2,3-dihydrobenzo[1,4]dioxin-6-yl)amide;
2-(4-Bromobenzoylamino)-4-methylthiazole-5-carboxylic acid benzylamide;
2-(4-Bromobenzoylamino)-4-methylthiazole-5-carboxylic acid indan-5-ylamide;
4-Methyl-2-(3-methylbenzoylamino)thiazole-5-carboxylic acid indan-5-ylamide;
4-Methyl-2-(3,4,5-trimethoxybenzoylamino)thiazole-5-carboxylic acid cyclohexylamide;
2-Fluoro-N-[4-methyl-5-(piperidine-1-carbonyl)thiazol-2-yl]benzamide;
4-Bromo-N-[4-methyl-5-(morpholine-4-carbonyl)thiazol-2-yl]benzamide;
4-Methoxy-N-[4-methyl-5-(morpholine-4-carbonyl)thiazol-2-yl]benzamide;
2-(Cyclohexanecarbonylamino)-4-methylthiazole-5-carboxylic acid (4-methoxyphenyl)amide;
4-Methyl-2-(3,4,5-trimethoxybenzoylamino)thiazole-5-carboxylic acid o-tolylamide;
4-Methyl-2-(3,4,5-trimethoxybenzoylamino)thiazole-5-carboxylic acid (3-chlorophenyl)amide;
2-(4-Methoxybenzoylamino)-4-methylthiazole-5-carboxylic acid (3-methoxyphenyl)amide;
4-Methyl-2-(4-methylbenzoylamino)thiazole-5-carboxylic acid (2,3-dihydrobenzo[1,4]dioxin-6-yl)amide;
4-Methyl-2-(3,4,5-trimethoxybenzoylamino)thiazole-5-carboxylic acid (2,3-dihydro-benzo[1,4]dioxin-6-yl)amide;
4-Methyl-2-(4-methylbenzoylamino)thiazole-5-carboxylic acid benzylamide;
4-Methyl-2-(4-methylbenzoylamino)thiazole-5-carboxylic acid indan-5-ylamide;
4-Methyl-2-(4-methylbenzoylamino)thiazole-5-carboxylic acid (4-chlorophenyl)amide;
4-Methyl-2-(4-methylbenzoylamino)thiazole-5-carboxylic acid (3-chlorophenyl)amide;
4-Methyl-2-(4-methylbenzoylamino)thiazole-5-carboxylic acid (2-chlorophenyl)amide;
4-Methyl-2-(4-methylbenzoylamino)thiazole-5-carboxylic acid (3-methoxyphenyl)amide;
4-Methyl-2-(4-methylbenzoylamino)thiazole-5-carboxylic acid phenylamide;
2-(Cyclohexanecarbonylamino)-4-methylthiazole-5-carboxylic acid (4-chlorophenyl)amide;
2-(Cyclohexanecarbonylamino)-4-methylthiazole-5-carboxylic acid (2-chlorophenyl)amide;
3-Methyl-1-phenyl-1H-thieno[2,3-c]pyrazole-5-carboxylic acid [5-(2-chloro-phenylcarbamoyl)-4-methylthiazol-2-yl]amide;
2-(Cyclohexanecarbonylamino)-4-methylthiazole-5-carboxylic acid indan-5-ylamide;
{[2-(4-Methoxy-benzoylamino)-4-methylthiazole-5-carbonyl]amino}acetic acid ethyl ester;
3-Fluoro-N-[4-methyl-5-(morpholine-4-carbonyl)thiazol-2-yl]benzamide;
2-[(5-Chloro-3-methyl-1-phenyl-1H-pyrazole-4-carbonyl)amino]-4-methylthiazole-5-carboxylic acid cyclohexylamide;
4-Methyl-2-(3-phenylacryloylamino)thiazole-5-carboxylic acid (2-dimethylaminoethyl)amide;
2-[(Furan-2-carbonyl)amino]-4-methylthiazole-5-carboxylic acid phenylamide;
2-[(Adamantane-1-carbonyl)amino]-4-methylthiazole-5-carboxylic acid phenylamide;

2-[(Adamantane-1-carbonyl)amino]-4-methylthiazole-5-carboxylic acid (4-bromophenyl)amide;
2-(3-Methoxybenzoylamino)-4-methylthiazole-5-carboxylic acid (4-chlorophenyl)amide;
2-[(Furan-2-carbonyl)amino]-4-methylthiazole-5-carboxylic acid (3-chlorophenyl)amide;
2-(3-Methoxybenzoylamino)-4-methylthiazole-5-carboxylic acid (3-chlorophenyl)amide;
2-(3-Methoxybenzoylamino)-4-methylthiazole-5-carboxylic acid (2-chlorophenyl)amide;
2-(3-Methoxybenzoylamino)-4-methylthiazole-5-carboxylic acid (2,3-dihydro-benzo[1,4]dioxin-6-yl)amide;
2-(3-Methoxybenzoylamino)-4-methylthiazole-5-carboxylic acid indan-5-ylamide;
{[2-(3-Methoxybenzoylamino)-4-methylthiazole-5-carbonyl]amino}acetic acid ethyl ester;
2-(4-Bromobenzoylamino)-4-methylthiazole-5-carboxylic acid (5-methyl[1,3,4]thiadiazol-2-yl)amide;
2-(3-Methoxy-benzoylamino)-4-methylthiazole-5-carboxylic acid (4-methoxyphenyl)amide;
2-[(Adamantane-1-carbonyl)amino]-4-methylthiazole-5-carboxylic acid (4-methoxyphenyl)amide;
3-Methyl-1-phenyl-1H-thieno[2,3-c]pyrazole-5-carboxylic acid (4-methyl-5-phenylcarbamoyl-thiazol-2-yl)amide;
3-Methyl-1-phenyl-1H-thieno[2,3-c]pyrazole-5-carboxylic acid (4-methyl-5-o-tolylcarbamoyl-thiazol-2-yl)amide;
2-[(5-Chloro-3-methyl-1-phenyl-1H-pyrazole-4-carbonyl)amino]-4-methylthiazole-5-carboxylic acid (4-bromophenyl)amide;
2-[(5-Chloro-3-methyl-1-phenyl-1H-pyrazole-4-carbonyl)amino]-4-methylthiazole-5-carboxylic acid (2-chlorophenyl)amide;
3-Methyl-1-phenyl-1H-thieno[2,3-c]pyrazole-5-carboxylic acid [5-(2,3-dihydro-benzo[1,4]dioxin-6-ylcarbamoyl)-4-methylthiazol-2-yl]amide;
3-Methyl-1-phenyl-1H-thieno[2,3-c]pyrazole-5-carboxylic acid [5-(indan-5-ylcarbamoyl)-4-methylthiazol-2-yl]amide;
3-Methyl-1-phenyl-1H-thieno[2,3-c]pyrazole-5-carboxylic acid [4-methyl-5-(5-methyl-[1,3,4]thiadiazol-2-ylcarbamoyl)thiazol-2-yl]amide;
3-Methyl-1-phenyl-1H-thieno[2,3-c]pyrazole-5-carboxylic acid [4-methyl-5-(piperidine-1-carbonyl)thiazol-2-yl]amide;
3-Methyl-N-[4-methyl-5-(piperidine-1-carbonyl)thiazol-2-yl]benzamide;
3-Methyl-1-phenyl-1H-thieno[2,3-c]pyrazole-5-carboxylic acid [5-(4-methoxy-phenylcarbamoyl)-4-methylthiazol-2-yl]amide;
4-Methyl-2-(4-methylbenzoylamino)thiazole-5-carboxylic acid cyclohexylamide;
2-(Cyclohexanecarbonylamino)-4-methylthiazole-5-carboxylic acid (3-chlorophenyl)amide;
4-Methyl-2-[(thiophene-2-carbonyl)amino]thiazole-5-carboxylic acid (2,3-dihydro-benzo[1,4]dioxin-6-yl)amide;
2-[(Adamantane-1-carbonyl)amino]-4-methylthiazole-5-carboxylic acid benzylamide;
4-Methyl-2-(4-methylbenzoylamino)thiazole-5-carboxylic acid (4-bromophenyl)amide;
2-(Cyclohexanecarbonylamino)-4-methylthiazole-5-carboxylic acid (4-bromophenyl)amide;
4-Methyl-2-(3-methylbenzoylamino)thiazole-5-carboxylic acid (4-bromophenyl)amide;
2-(2-Fluorobenzoylamino)-4-methylthiazole-5-carboxylic acid (4-chlorophenyl)amide;
2-(2-Fluorobenzoylamino)-4-methylthiazole-5-carboxylic acid (2-chlorophenyl)amide;
2-(3-Fluorobenzoylamino)-4-methylthiazole-5-carboxylic acid indan-5-ylamide;
3-Methyl-1-phenyl-1H-thieno[2,3-c]pyrazole-5-carboxylic acid [5-(4-chloro-phenylcarbamoyl)-4-methylthiazol-2-yl]amide;
4-Methyl-2-(3-phenylacryloylamino)thiazole-5-carboxylic acid (3-chlorophenyl)amide;
2-Acetylamino-4-methylthiazole-5-carboxylic acid (3-methoxyphenyl)amide;
4-Methyl-2-(4-nitrobenzoylamino)thiazole-5-carboxylic acid (4-methoxyphenyl)amide;
2-Acetylamino-4-methylthiazole-5-carboxylic acid (4-chlorophenyl)amide;
2-Acetylamino-4-methylthiazole-5-carboxylic acid (4-methoxyphenyl)amide;
4-Methyl-2-(4-methylbenzoylamino)thiazole-5-carboxylic acid (5-methyl[1,3,4]thiadiazol-2-yl)amide;
2-(4-Bromobenzoylamino)-4-methylthiazole-5-carboxylic acid phenylamide;
4-Methyl-2-(3-phenylacryloylamino)thiazole-5-carboxylic acid (4-methoxyphenyl)amide;
4-Methyl-2-propionylaminothiazole-5-carboxylic acid (4-methoxyphenyl)amide;
2-(Cyclopropanecarbonylamino)-4-methylthiazole-5-carboxylic acid (4-methoxyphenyl)amide;
4-Methyl-2-propionylamino-thiazole-5-carboxylic acid (4-bromophenyl)amide;
4-Methyl-2-(4-nitrobenzoylamino)thiazole-5-carboxylic acid (2-chlorophenyl)amide;
{[2-(4-Fluorobenzoylamino)-4-methylthiazole-5-carbonyl]amino}acetic acid ethyl ester;
{[2-(3-Fluorobenzoylamino)-4-methylthiazole-5-carbonyl]amino}acetic acid ethyl ester;
2-(2-Fluorobenzoylamino)-4-methylthiazole-5-carboxylic acid (4-methoxyphenyl)amide;
N-[4-Methyl-5-(piperidine-1-carbonyl)thiazol-2-yl]-2-phenoxyacetamide;
2-(4-tert-Butylbenzoylamino)-4-methylthiazole-5-carboxylic acid (4-bromophenyl)amide;
4-Methyl-2-(3-phenylacryloylamino)thiazole-5-carboxylic acid (4-bromophenyl)amide;
4-Methyl-2-(3-phenylacryloylamino)thiazole-5-carboxylic acid (4-chlorophenyl)amide;
2-(4-tert-Butylbenzoylamino)-4-methylthiazole-5-carboxylic acid (3-chlorophenyl)amide;
2-(4-tert-Butylbenzoylamino)-4-methylthiazole-5-carboxylic acid (2-chlorophenyl)amide;
4-Methyl-2-(3-phenylacryloylamino)thiazole-5-carboxylic acid benzylamide;
2-(4-tert-Butylbenzoylamino)-4-methylthiazole-5-carboxylic acid cyclohexylamide;
2-(4-Methoxybenzoylamino)-4-methylthiazole-5-carboxylic acid (5-methyl[1,3,4]thiadiazol-2-yl)amide;
4-Methyl-2-(4-nitro-benzoylamino)thiazole-5-carboxylic acid o-tolylamide;
2-Benzoylamino-4-methylthiazole-5-carboxylic acid (4-bromophenyl)amide;
4-Methyl-2-(2-methylbenzoylamino)thiazole-5-carboxylic acid (4-bromophenyl)amide;
4-Methyl-2-(2-phenoxyacetylamino)thiazole-5-carboxylic acid (4-bromophenyl)amide;
3-Methyl-1-phenyl-1H-thieno[2,3-c]pyrazole-5-carboxylic acid [5-(4-bromo-phenylcarbamoyl)-4-methylthiazol-2-yl]amide;
4-Methyl-2-(4-nitrobenzoylamino)thiazole-5-carboxylic acid (4-chlorophenyl)amide;

2-Benzoylamino-4-methylthiazole-5-carboxylic acid (3-chlorophenyl)amide;
4-Methyl-2-(2-phenoxyacetylamino)thiazole-5-carboxylic acid (3-chlorophenyl)amide;
3-Methyl-1-phenyl-1H-thieno[2,3-c]pyrazole-5-carboxylic acid [5-(3-chloro-phenylcarbamoyl)-4-methylthiazol-2-yl]amide;
2-Benzoylamino-4-methylthiazole-5-carboxylic acid o-tolylamide;
4-Methyl-2-(2-phenoxy-acetylamino)thiazole-5-carboxylic acid (3-methoxyphenyl)amide;
2-Benzoylamino-4-methylthiazole-5-carboxylic acid (2,3-dihydrobenzo[1,4]dioxin-6-yl)amide;
3-Methyl-1-phenyl-1H-thieno[2,3-c]pyrazole-5-carboxylic acid (5-benzylcarbamoyl-4-methylthiazol-2-yl)amide;
4-Methyl-2-propionylaminothiazole-5-carboxylic acid (3-methoxyphenyl)amide;
3-Methyl-1-phenyl-1H-thieno[2,3-c]pyrazole-5-carboxylic acid [5-(3-methoxy-phenylcarbamoyl)-4-methylthiazol-2-yl]amide;
4-Methyl-2-(2-methylbenzoylamino)thiazole-5-carboxylic acid indan-5-ylamide;
2-Benzoylamino-4-methylthiazole-5-carboxylic acid (4-methoxyphenyl)amide;
4-Methyl-2-(2-phenoxyacetylamino)thiazole-5-carboxylic acid (4-methoxyphenyl)amide;
4-Methyl-2-(3,4,5-trimethoxybenzoylamino)thiazole-5-carboxylic acid (4-methoxyphenyl)amide;
2-(Cyclopropanecarbonylamino)-4-methylthiazole-5-carboxylic acid o-tolylamide;
4-Methyl-2-propionylaminothiazole-5-carboxylic acid (4-chlorophenyl)amide;
4-Methyl-2-propionylaminothiazole-5-carboxylic acid (3-chlorophenyl)amide;
4-Methyl-2-propionylaminothiazole-5-carboxylic acid (2-chlorophenyl)amide;
4-Methyl-2-(4-nitrobenzoylamino)thiazole-5-carboxylic acid (3-chlorophenyl)amide;
2-(4-Fluorobenzoylamino)-4-methylthiazole-5-carboxylic acid (2,3-dihydrobenzo[1,4]dioxin-6-yl)amide;
2-(4-Fluorobenzoylamino)-4-methylthiazole-5-carboxylic acid indan-5-ylamide;
4-Fluoro-N-[4-methyl-5-(piperidine-1-carbonyl)thiazol-2-yl]benzamide;
2-(4-tert-Butylbenzoylamino)-4-methylthiazole-5-carboxylic acid indan-5-ylamide;
4-Methyl-2-propionylaminothiazole-5-carboxylic acid cyclohexylamide;
N-[4-Methyl-5-(piperidine-1-carbonyl)thiazol-2-yl]propionamide;
2-(Cyclopropanecarbonylamino)-4-methylthiazole-5-carboxylic acid (3-chlorophenyl)amide;
2-(3-Fluorobenzoylamino)-4-methylthiazole-5-carboxylic acid (3-methoxyphenyl)amide;
2-(Cyclopropanecarbonylamino)-4-methylthiazole-5-carboxylic acid (2-chlorophenyl)amide;
4-Methyl-2-(4-nitrobenzoylamino)thiazole-5-carboxylic acid phenylamide;
2-(Cyclopropanecarbonylamino)-4-methylthiazole-5-carboxylic acid cyclohexylamide;
4-Methyl-2-(4-nitrobenzoylamino)thiazole-5-carboxylic acid (2,3-dihydrobenzo[1,4]dioxin-6-yl)amide;
2-(4-tert-Butylbenzoylamino)-4-methylthiazole-5-carboxylic acid phenylamide;
4-Methyl-2-(3-phenylacryloylamino)thiazole-5-carboxylic acid phenylamide;
4-Methyl-2-(3-phenylacryloylamino)thiazole-5-carboxylic acid o-tolylamide;
4-Methyl-2-[(thiophene-2-carbonyl)amino]thiazole-5-carboxylic acid (5-methyl-[1,3,4]thiadiazol-2-yl)amide;
4-Methyl-2-(3-phenylacryloylamino)thiazole-5-carboxylic acid (2-chlorophenyl)amide;
4-Methyl-2-(4-nitrobenzoylamino)thiazole-5-carboxylic acid (4-bromophenyl)amide;
4-Methyl-2-(3-phenylacryloylamino)thiazole-5-carboxylic acid indan-5-ylamide;
4-Methyl-2-(3-phenylacryloylamino)thiazole-5-carboxylic acid (2-hydroxy-ethyl)amide;
3-Methyl-1-phenyl-1H-thieno[2,3-c]pyrazole-5-carboxylic acid (5-cyclohexylcarbamoyl-4-methylthiazol-2-yl)amide;
{[2-(2-Fluorobenzoylamino)-4-methylthiazole-5-carbonyl]amino}acetic acid ethyl ester;
4-Methyl-2-(3,4,5-trimethoxybenzoylamino)thiazole-5-carboxylic acid (4-bromophenyl)amide;
2-(Cyclohexanecarbonylamino)-4-methylthiazole-5-carboxylic acid benzylamide;
N-[4-Methyl-5-(morpholine-4-carbonyl)thiazol-2-yl]-3-phenylacrylamide;
N-[4-Methyl-5-(morpholine-4-carbonyl)thiazol-2-yl]-4-nitrobenzamide;
{[4-Methyl-2-(3-phenylacryloylamino)thiazole-5-carbonyl]amino}acetic acid ethyl ester;
4-Methyl-2-(3-phenylacryloylamino)thiazole-5-carboxylic acid (2,3-dihydrobenzo[1,4]dioxin-6-yl)amide;
4-Methyl-2-(3-phenylacryloylamino)thiazole-5-carboxylic acid pyridin-3-ylamide;
N-[4-Methyl-5-(piperidine-1-carbonyl)thiazol-2-yl]-3-phenylacrylamide;
4-Methyl-2-(3-phenylacryloylamino)thiazole-5-carboxylic acid cyclohexylamide;
4-Methyl-2-(3,4,5-trimethoxybenzoylamino)thiazole-5-carboxylic acid (5-methyl-[1,3,4]thiadiazol-2-yl)amide;
4-Methyl-2-propionylaminothiazole-5-carboxylic acid o-tolylamide;
Cyclopropanecarboxylic acid [4-methyl-5-(piperidine-1-carbonyl)thiazol-2-yl]amide;
4-Methyl-2-(2-phenoxyacetylamino)thiazole-5-carboxylic acid o-tolylamide;
4-Methyl-2-(2-phenoxyacetylamino)thiazole-5-carboxylic acid (2,3-dihydrobenzo[1,4]dioxin-6-yl)amide;
2-(Cyclopropanecarbonylamino)-4-methylthiazole-5-carboxylic acid (4-bromophenyl)amide;
4-Methyl-2-(3,4,5-trimethoxybenzoylamino)thiazole-5-carboxylic acid indan-5-ylamide;
2-[(Adamantane-1-carbonyl)amino]-4-methylthiazole-5-carboxylic acid cyclohexylamide;
2-(3-Chlorobenzoylamino)-4-methylthiazole-5-carboxylic acid pyridin-3-ylamide;
2-(3-Chlorobenzoylamino)-4-methylthiazole-5-carboxylic acid cyclohexylamide;
{[4-Methyl-2-(3,4,5-trimethoxybenzoylamino)thiazole-5-carbonyl]amino}acetic acid ethyl ester;
4-Methyl-2-(2-methylbenzoylamino)thiazole-5-carboxylic acid (3-chlorophenyl)amide;
2-(4-Chlorobenzoylamino)-4-methylthiazole-5-carboxylic acid cyclohexylamide;
4-Methyl-2-(4-methylbenzoylamino)thiazole-5-carboxylic acid (2-dimethylaminoethyl)amide;
5-tert-Butyl-2-methyl-2H-pyrazole-3-carboxylic acid (7,7-dimethyl-4-oxo-5,6,7,8-tetrahydro-4H-thiazolo[5,4-c]azepin-2-yl)amide;

2-[(5-Chloro-3-methyl-1-phenyl-1H-pyrazole-4-carbonyl)
amino]-4-methylthiazole-5-carboxylic acid indan-5-ylamide;
4-Methyl-2-(4-nitrobenzoylamino)thiazole-5-carboxylic
acid indan-5-ylamide;
2-Acetylamino-4-methylthiazole-5-carboxylic acid (5-methyl[1,3,4]thiadiazol-2-yl)amide;
2-Chloro-N-(7,7-dimethyl-4-oxo-5,6,7,8-tetrahydro-4H-thiazolo[5,4-c]azepin-2-yl)-benzamide;
N-(7,7-Dimethyl-4-oxo-5,6,7,8-tetrahydro-4H-thiazolo[5,4-c]azepin-2-yl)benzamide;
N-(4-Oxo-5,6,7,8-tetrahydro-4H-thiazolo[5,4-c]azepin-2-yl)benzamide;
2-Chloro-N-(4-oxo-5,6,7,8-tetrahydro-4H-thiazolo[5,4-c]azepin-2-yl)benzamide;
2-(3,4-Dimethoxybenzoylamino)-4-methylthiazole-5-carboxylic acid dimethylamide;
4-Methyl-2-(2-phenyl-propionylamino)thiazole-5-carboxylic acid dimethylamide;
2-(2,6-Difluorobenzoylamino)-4-methylthiazole-5-carboxylic acid dimethylamide;
3-Chloro-N-[4-methyl-5-(piperidine-1-carbonyl)thiazol-2-yl]benzamide;
2-[2-(4-Chloro-2-methylphenoxy)propionylamino]-4-methylthiazole-5-carboxylic acid dimethylamide;
6,8-Dimethyl-2-pyridin-4-ylquinoline-4-carboxylic acid (5-dimethylcarbamoyl-4-methylthiazol-2-yl)amide;
4-Methyl-2-[(3-methylbenzofuran-2-carbonyl)amino]thiazole-5-carboxylic acid dimethylamide;
2-Acetylamino-4-methylthiazole-5-carboxylic acid (3-chlorophenyl)amide;
4-Methyl-2-(2-phenoxyacetylamino)thiazole-5-carboxylic acid indan-5-ylamide;
5-(7,7-Dimethyl-4-oxo-5,6,7,8-tetrahydro-4H-thiazolo[5,4-c]azepin-2-ylcarbamoyl)-thiophene-2-carboxylic acid methyl ester;
4-Methyl-2-(3-methylbenzoylamino)thiazole-5-carboxylic acid cyclohexylamide;
4-Methyl-2-(3-phenylacryloylamino)thiazole-5-carboxylic acid (3-methoxyphenyl)amide;
4-Methyl-2-(4-nitrobenzoylamino)thiazole-5-carboxylic acid (3-methoxyphenyl)amide;
2-[(Adamantane-1-carbonyl)amino]-4-methylthiazole-5-carboxylic acid (3-methoxyphenyl)amide;
N-[5-(2-Cyclopropylethylcarbamoyl)-4-methylthiazol-2-yl]isonicotinamide;
N-(4-Methyl-5-phenethylcarbamoylthiazol-2-yl)isonicotinamide;
N-[4-Methyl-5-(3-phenylpropylcarbamoyl)thiazol-2-yl]isonicotinamide;
N-[5-(4-Chlorobenzylcarbamoyl)-4-methylthiazol-2-yl]isonicotinamide;
2-(Cyclopropanecarbonylamino)-4-methylthiazole-5-carboxylic acid 4-chloro-benzylamide;
2-(2,5-Difluorobenzoylamino)-4-methylthiazole-5-carboxylic acid benzylamide;
2-(Cyclobutanecarbonylamino)-4-methylthiazole-5-carboxylic acid benzylamide;
4-Methyl-2-[(2-phenylcyclopropanecarbonyl)amino]thiazole-5-carboxylic acid benzylamide;
2-(2-Fluorobenzoylamino)-4-methylthiazole-5-carboxylic acid benzylamide;
2-(2,2-Dimethylpropionylamino)-4-methylthiazole-5-carboxylic acid benzylamide;
2-Benzoylamino-4-methylthiazole-5-carboxylic acid benzylamide;
4-Methyl-2-(2-trifluoromethylbenzoylamino)thiazole-5-carboxylic acid benzylamide;
2-(4-Chlorobenzoylamino)-4-methylthiazole-5-carboxylic acid benzylamide;
2-(4-Fluorobenzoylamino)-4-methylthiazole-5-carboxylic acid benzylamide;
4-Methyl-2-(4-trifluoromethylbenzoylamino)thiazole-5-carboxylic acid benzylamide;
2-(2-Chlorobenzoylamino)-4-methylthiazole-5-carboxylic acid benzylamide;
2-(2,4-Dichlorobenzoylamino)-4-methylthiazole-5-carboxylic acid benzylamide;
2-(Cyclopentanecarbonylamino)-4-methylthiazole-5-carboxylic acid benzylamide;
2-(2-Chloro-4-fluorobenzoylamino)-4-methylthiazole-5-carboxylic acid benzylamide;
2-(3-Chlorobenzoylamino)-4-methylthiazole-5-carboxylic acid benzylamide;
4-Methyl-2-(2-trifluoromethoxybenzoylamino)thiazole-5-carboxylic acid benzylamide;
2-(3,5-Dichlorobenzoylamino)-4-methylthiazole-5-carboxylic acid benzylamide;
2-(3-Cyanobenzoylamino)-4-methylthiazole-5-carboxylic acid benzylamide;
2-(5-Chloro-2-fluorobenzoylamino)-4-methylthiazole-5-carboxylic acid benzylamide;
2-(3-Fluorobenzoylamino)-4-methylthiazole-5-carboxylic acid benzylamide;
4-Methyl-2-(4-trifluoromethoxybenzoylamino)thiazole-5-carboxylic acid benzylamide;
4-Methyl-2-(3-trifluoromethylbenzoylamino)thiazole-5-carboxylic acid benzylamide;
2-(3-Methoxybenzoylamino)-4-methylthiazole-5-carboxylic acid benzylamide;
4-Methyl-2-[(naphthalene-1-carbonyl)amino]thiazole-5-carboxylic acid benzylamide;
2-(4-Cyanobenzoylamino)-4-methylthiazole-5-carboxylic acid benzylamide;
2-(3,5-Difluorobenzoylamino)-4-methylthiazole-5-carboxylic acid benzylamide;
4-Methyl-2-(3-trifluoromethoxybenzoylamino)thiazole-5-carboxylic acid benzylamide;
2-(4-Methoxybenzoylamino)-4-methylthiazole-5-carboxylic acid benzylamide;
2-(3-Methanesulfonylbenzoylamino)-4-methylthiazole-5-carboxylic acid benzylamide;
2-(2-Methanesulfonylbenzoylamino)-4-methylthiazole-5-carboxylic acid benzylamide;
2-Benzoylamino-4-trifluoromethylthiazole-5-carboxylic acid benzylamide;
N-(5-Benzylcarbamoyl-4-methylthiazol-2-yl)nicotinamide;
2-(3,4-Dichlorobenzoylamino)-4-methylthiazole-5-carboxylic acid benzylamide;
2-(4-Methanesulfonylbenzoylamino)-4-methylthiazole-5-carboxylic acid benzylamide;
4-Methyl-2-(3-phenylpropionylamino)thiazole-5-carboxylic acid benzylamide;
2-Benzylamino-4-methylthiazole-5-carboxylic acid benzylamide;
4-Methyl-2-phenylacetylaminothiazole-5-carboxylic acid benzylamide;
2-Benzoylamino-4-phenylthiazole-5-carboxylic acid benzylamide;
4-Methyl-2-(3-phenylureido)thiazole-5-carboxylic acid benzylamide;
2-[3-(4-Fluorophenyl)ureido]-4-methylthiazole-5-carboxylic acid benzylamide;

2-[3-(4-Chlorophenyl)ureido]-4-methylthiazole-5-carboxylic acid benzylamide;
2-(2-Cyclopropylacetylamino)-4-methylthiazole-5-carboxylic acid benzylamide;
2-Benzoylamino-4-methylthiazole-5-carboxylic acid 2-trifluoromethylbenzylamide;
2-Benzoylamino-4-methylthiazole-5-carboxylic acid 3-chlorobenzylamide;
2-Benzoylamino-4-methylthiazole-5-carboxylic acid cyclopropylmethyl-amide;
2-Benzoylamino-4-methylthiazole-5-carboxylic acid 3-fluorobenzylamide;
2-Benzoylamino-4-methylthiazole-5-carboxylic acid 2-chlorobenzylamide;
2-Benzoylamino-4-methylthiazole-5-carboxylic acid 2-fluorobenzylamide;
2-Benzoylamino-4-methylthiazole-5-carboxylic acid 4-fluorobenzylamide;
2-Benzoylamino-4-methylthiazole-5-carboxylic acid benzylmethylamide;
2-Benzoylamino-4-chlorothiazole-5-carboxylic acid benzylamide;
2-[(4-Pentylbenzoyl)amino]-N-(phenylmethyl)-4-(trifluoromethyl)-5-thiazolecarboxamide;
2-Benzoylamino-4-methylthiazole-5-carboxylic acid (1-phenylpropyl)amide;
4-Methyl-2-(toluene-4-sulfonylamino)thiazole-5-carboxylic acid benzylamide;
4-Methyl-2-[4-(2H-tetrazol-5-yl)benzoylamino]thiazole-5-carboxylic acid benzylamide;
2-Benzoylamino-thiazole-5-carboxylic acid benzylamide;
4-Amino-2-benzoylaminothiazole-5-carboxylic acid benzylamide;
N-[5-(N-Benzoylhydrazinocarbonyl)-4-methylthiazol-2-yl]benzamide;
N-[5-(Imidazole-1-carbonyl)-4-methylthiazol-2-yl]benzamide;
4-Methyl-2-(4-phenylbutyrylamino)thiazole-5-carboxylic acid benzylamide;
4-Methyl-2-(5-phenylpentanoylamino)thiazole-5-carboxylic acid benzylamide;
4-Methyl-2-[4-(2-oxo-2H-pyridin-1-yl)benzoylamino]-thiazole-5-carboxylic acid benzylamide;
2-[(5-Benzylcarbamoyl-4-methyl-thiazol-2-ylcarbamoyl)methyl]benzoic acid;
N-(5-Benzylcarbamoyl-4-methylthiazol-2-yl)-2-methoxyisonicotinamide;
2-Oxo-1,2-dihydropyridine-4-carboxylic acid (5-benzylcarbamoyl-4-methylthiazol-2-yl)amide;
2-Oxo-1-phenyl-1,2-dihydropyridine-4-carboxylic acid (5-benzylcarbamoyl-4-methyl-thiazol-2-yl)amide;
N,4-Dibenzyl-2-(3-phenylpropanamido)thiazole-5-carboxamide;
2-Benzamido-N,4-dibenzylthiazole-5-carboxamide;
2-(4-Bromo-2-hydroxymethylbenzoylamino)-4-methylthiazole-5-carboxylic acid benzylamide;
4-Methyl-2-[(1-phenylcyclopentanecarbonyl)amino]thiazole-5-carboxylic acid benzylamide;
2-{(4-Fluorobenzoyl)-[2-(4-fluorobenzoylamino)ethyl]amino}-4-methylthiazole-5-carboxylic acid benzylamide;
N-benzyl-4-methyl-2-(N-methylbenzamido)thiazole-5-carboxamide;
N-benzyl-N,4-dimethyl-2-(N-methylbenzamido)thiazole-5-carboxamide;
2-(4-((1H-pyrazol-1-yl)methyl)benzamido)-N-benzyl-4-methylthiazole-5-carboxamide;
N-Benzyl-4-(morpholinomethyl)-2-(3-phenylpropanamido)thiazole-5-carboxamide;
N-benzyl-2-(4-benzylbenzamido)-4-methylthiazole-5-carboxamide;
2-(4-Benzylbenzoylamino)-4-diethylaminomethylthiazole-5-carboxylic acid benzylamide;
2-Benzamido-N-benzyl-4-((diethylamino)methyl)thiazole-5-carboxamide;
2-(4-Benzylbenzamido)-N-(2-cyanoethyl)-4-methylthiazole-5-carboxamide;
2-(4-Benzylbenzamido)-N-ethyl-4-methylthiazole-5-carboxamide; and
N-Benzyl-2-(4-benzylbenzamido)-4-((methylamino)methyl)thiazole-5-carboxamide.

The present invention also relates to pharmaceutical composition containing the compounds of formula (I). In one embodiment, the invention relates to a composition comprising compounds of formula (I) in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of formula (I) is present in an amount effective to reduce said lipid level.

Specific embodiments of the compounds of formula (I) are described in more detail below in the Preparation of the Compounds of the Invention.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome, dermatological disorders and the like, by administering to a patient in need of such treatment an effective amount of an SCD-modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described herein. Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montréal, Quebec)), and Sprague Dawley rats (Charles Rivers), as used in models for diet-induced obesity (Ghibaudi, L. et al. (2002), *Obes. Res.* Vol. 10, pp. 956-963). Similar models have also been developed for mice.

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition is any disease or condition in which the activity of SCD is elevated and/or where inhibition of SCD activity can be demonstrated to bring about symptomatic improvements for the individual so treated. As defined herein, an SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy. In a preferred embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In a preferred embodiment, compounds of the invention will be used to treat diabetes mellitus and/or obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia. The American Heart Association has published guidelines for the diagnosis of metabolic syndrome, Grundy, S., et. al. (2006) *Cardiol. Rev.* Vol. 13, No. 6, pp. 322-327.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including but not limited to eczema, acne, psoriasis, keloid scar formation or prevention, diseases related to production or secretions from mucous membranes, such as monounsaturated fatty acids, wax esters, and the like. Preferably, the compounds of the invention inhibition of SCD activity can prevent or attenuate keloid scar formation by reduction of excessive sebum production that typically results in their formation.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the $C_9$-$C_{10}$ desaturation of stearoyl-CoA) which is accomplished by delta-9 desaturases, such as stearoyl-CoA desaturase 1 (SCD1). As such these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 2 mg/Kg, 1 mg/Kg, or 0.5 mg/Kg and the target human dose is between 50 and 250 mg/70 Kg, although doses outside of this range may be acceptable. ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 μM, preferably below 1 μM and most preferably below 50 nM. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ in a 15 minute microsomal assay of preferably less than 10 μM, less than 5 μM, less than 2.5 μM, less than 1 μM, less than 750 nM, less than 500 nM, less than 250 nM, less than 100 nM, less than 50 nM, and most preferably less than 20 nM. The compound of the invention may show reversible inhibition (i.e., competitive inhibition) and preferably does not inhibit other iron binding proteins. The required dosage should preferably be no more than about once or twice a day or at meal times.

The identification of compounds of the invention as SCD inhibitors was readily accomplished using the SCD enzyme and microsomal assay procedure described in Shanklin J. and Summerville C., *Proc. Natl. Acad. Sci. USA* (1991), Vol. 88, pp. 2510-2514. When tested in this assay, compounds of the invention had less than 50% remaining SCD activity at 10 μM concentration of the test compound, preferably less than 40% remaining SCD activity at 10 μM concentration of the test compound, more preferably less than 30% remaining SCD activity at 10 μM concentration of the test compound, and even more preferably less than 20% remaining SCD activity at 10 μM concentration of the test compound, thereby demonstrating that the compounds of the invention are potent inhibitors of SCD activity.

These results provide the basis for analysis of the structure-activity relationship (SAR) between test compounds and SCD. Certain substituents on the test compounds tend to provide more potent inhibitory compounds. SAR analysis is one of the tools those skilled in the art may now employ to identify preferred embodiments of the compounds of the invention for use as therapeutic agents.

Other methods of testing the compounds disclosed herein are also readily available to those skilled in the art. Thus, in addition, the determination of the ability of a compound to inhibit SCD may be accomplished in vivo. In one such embodiment, this is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase or other enzymes containing Fe at the active site.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available. Rabbits and hamsters are also useful as animal models, especially those expressing CETP (cholesteryl ester transfer protein).

Another suitable method for determining the in vivo efficacy of the compounds of the invention is to indirectly measure their impact on inhibition of SCD enzyme by measuring a subject's Desaturation Index after administration of the compound. "Desaturation Index" as employed in this specification means the ratio of the product over the substrate for the SCD enzyme as measured from a given tissue sample. This may be calculated using three different equations 18:1n-9/18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate). Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, with a subsequent modulation of the activity of multiple enzymes present within the membrane, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art know how to determine suitable doses of the compounds for use in treating the diseases and disorders contemplated herein. Therapeutic doses are generally identified through a dose ranging study in humans based on preliminary evidence derived from animal studies. Doses must be sufficient to result in a desired therapeutic benefit without causing unwanted side-effects for the patient. The preferred dosage range for an animal is 0.001 mg/Kg to 10,000 mg/Kg, including 0.5 mg/Kg, 1.0 mg/Kg and 2.0 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

The pharmaceutical compositions according to the invention are those suitable for enteral, such as oral or rectal, transdermal and parenteral administration to mammals, including man, to inhibit stearoyl-CoA desaturase, and for the treatment of conditions associated with stearoyl desaturase activity. In general, the pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. For enteral or parenteral application, preferred to administer an effective amount of a pharmaceutical composition according to the invention as Preferred tablets or gelatin capsules. Such pharmaceutical compositions may comprise, for example, the active ingredient together with diluents (e.g., lactose, dextrose, sucrose, mannitol, sorbitol, cellulose and/or glycine); lubricants (e.g., silica, talcum, stearic acid, its magnesium or calcium salt and/or polyethyleneglycol); and for tablets also comprises binders (e.g., magnesium aluminum silicate, starch paste, gelatin, tragacanth, methylcellulose, sodium carboxymethylcellulose and/or polyvinylpyrrolidone); and disintegrants (e.g., starches, agar, alginic acid or its sodium salt); or effervescent mixtures; and absorbants; colorants; flavors and sweeteners.

In another aspect of the present invention the compounds may be in the form of injectable compositions, e.g. preferably aqueous isotonic solutions or suspensions, and suppositories, which can be advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are may be prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

The most suitable route will depend on the nature and severity of the condition being treated. Those skilled in the art are also familiar with determining administration methods, dosage forms, suitable pharmaceutical excipients and other matters relevant to the delivery of the compounds to a subject in need thereof.

The compounds of the invention may be usefully combined with one or more other therapeutic agents for the treatment of SCD-mediated diseases and conditions. Preferably, the other therapeutic agent is selected from antidiabetics, hypolipidemic agents, anti-obesity agents, anti-hypertensive agents or inotropic agents.

Thus, an additional aspect of the present invention concerns a pharmaceutical composition comprising a therapeutically effective amount of a compound of the invention in combination with one or more other therapeutic agents. For example, the pharmaceutical composition can be formulated to comprise a therapeutically effective amount of a compound of the invention as defined above, in combination with another therapeutic agent, each at an effective therapeutic dose as reported in the art. Such therapeutic agents may, for example, include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; PPARg and/or PPARa (peroxisome proliferator-activated receptor) ligands such as MCC-555, MK767, L-165041, GW7282 or thiazolidinediones such as rosiglitazone, pioglitazone, troglitazone; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441, N,N-57-05445 or RXR ligands such as GW-0791, AGN-194204; sodium-dependent glucose cotransporter inhibitors, such as T-1095, glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors such as LAF237 (Vildagliptin); hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (farnesoid X receptor) and LXR (liver X receptor) ligands, cholestyramine, fibrates, nicotinic acid and aspirin; anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na—K-ATPase membrane pump, such as digoxin; neutral-endopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; b-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil. Other specific antidiabetic compounds are described by Patel Mona (*Expert Opin. Investig. Drugs.* (2003) April; 12(4):623-33) in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

Preparation of the Compounds of the Invention

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. In the following Reaction Schemes, $R^1, R^2, R^3, R^4, R^5$, W and V are defined as in the Summary of the Invention for compounds of formula (I) unless specifically defined, X is chloro or bromo and R' is a protecting group.

In general, the aminothiazole compounds of formula (I) of this invention can be synthesized following the general procedure as described in Scheme 1 where W is —N($R^5$)C(O)— and V is —C(O)—:

REACTION SCHEME 1

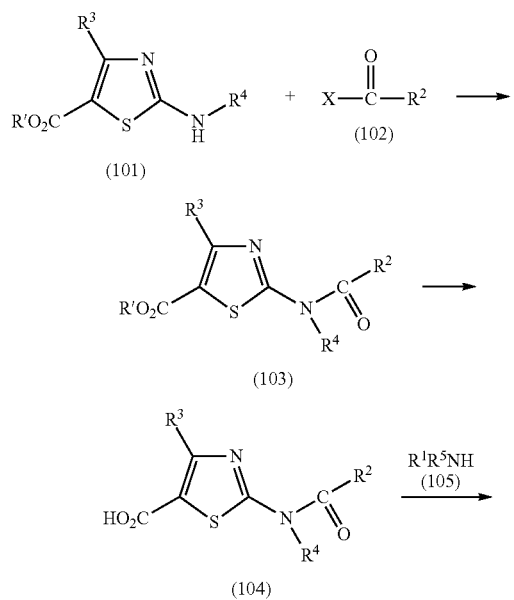

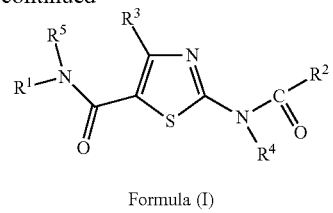

Formula (I)

The starting materials for the above reaction scheme are commercially available or can be prepared according to methods known to one skilled in the art or by methods disclosed herein. In general, the compounds of the invention are prepared in the above reaction scheme as follows:

Compound (101) is treated with compound (102) in the presence of a base, such as, but not limited to, triethylamine to generate compound (103) which undergoes a standard deprotecting procedure known to the one skilled in the art to generate the carboxylic acid of (104). The coupling between compounds (104) and (105) under standard amide bond formation conditions known to the one skilled in the art affords the compound of formula (I) of the invention where W is —N(R$^5$)C(O)— and V is —C(O)—.

Alternatively, the aminothiazole compounds of formula (I) of this invention can be synthesized following the general procedure as described in Scheme 2 where W is —N(R$^5$)C(O)—:

REACTION SCHEME 2

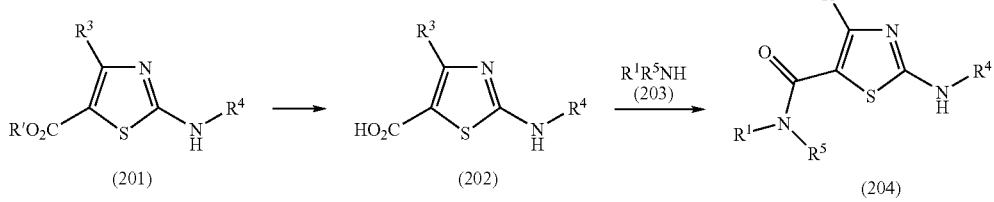

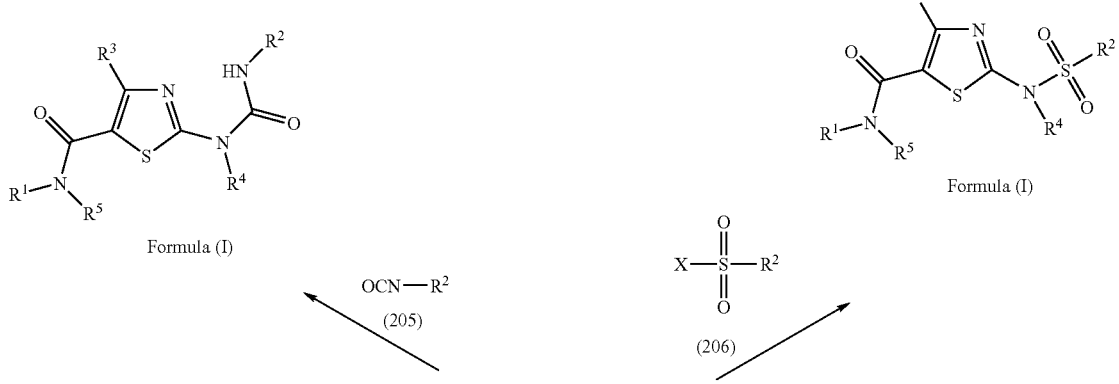

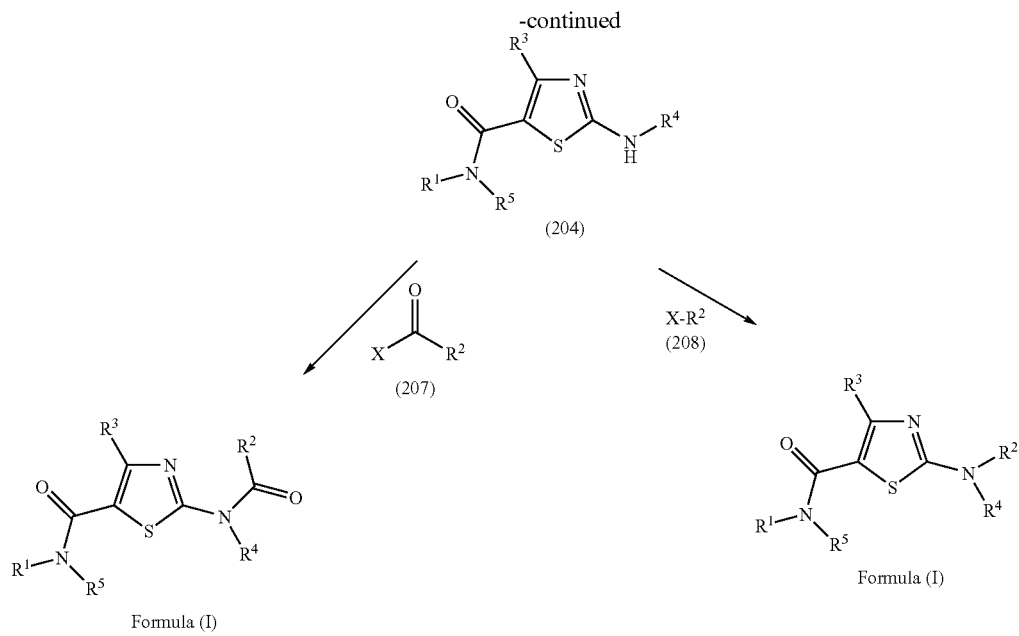

The starting materials for the above reaction scheme are commercially available or can be prepared according to methods known to one skilled in the art or by methods disclosed herein. In general, the compounds of the invention are prepared in the above reaction scheme as follows:

The starting ester compound (201) undergoes a standard deprotecting procedure known to the one skilled in the art to generate the carboxylic acid of (202). The coupling between compounds (202) and (203) under standard amide bond formation conditions known to the one skilled in the art affords compound (204). Compound (204) then is used as a starting material to generate compounds with different linker V.

Compound (204) reacts with isocyanate of (205) to generate the urea compound of formula (I) of the invention where W is —N($R^5$)C(O)— and V is —C(O)NH—. Alternatively, compound (204) is treated with the sulfonyl compound (206) to afford compound of (I) of the invention where W is —N($R^5$)C(O)— and V is —S(O)$_2$—. Alternatively, compound (204) is coupled with acid chloride or bromide (207) to generate compound of formula (I) of the invention where W is —N($R^5$)C(O)— and V is —C(O)—. Alternatively, compound (204) reacts with the halide (208) to afford the compound of formula (I) of the invention where W is —N($R^5$)C(O)— and V is a direct bond.

Alternatively, the aminothiazole compounds of formula (I) of this invention can be synthesized following the general procedure as described in Scheme 3 where W is —N($R^5$)C(O)— and V is —NHCH($R^1$)—:

REACTION SCHEME 3

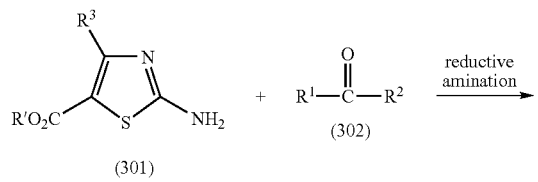

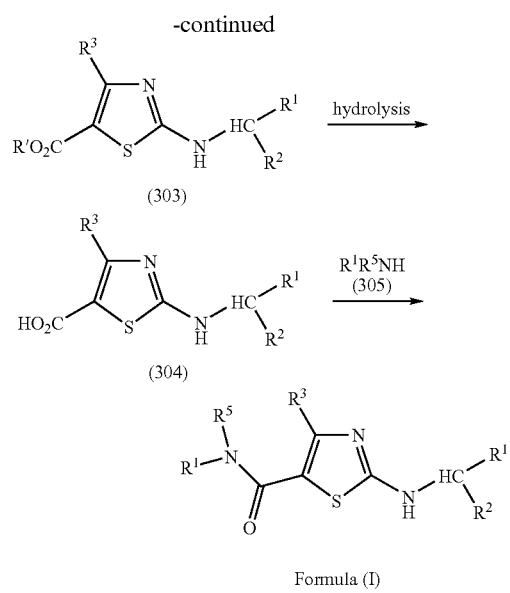

The starting materials for the above reaction scheme are commercially available or can be prepared according to methods known to one skilled in the art or by methods disclosed herein. In general, the compounds of the invention are prepared in the above reaction scheme as follows:

Compound (301) is treated with compound (302) under reductive amination conditions to generate compound (303) which undergoes standard hydrolysis procedure known to the one skilled in the art to generate the carboxylic acid of (304). The coupling between compounds (304) and (305) under standard amide bond formation conditions known to the one skilled in the art affords the compound of formula (I) of the invention where W is —N($R^5$)C(O)— and V is —NHCH ($R^1$)—.

Although anyone skilled in the art is capable of preparing the compounds of the invention according to the general techniques disclosed above, more specific details on synthetic

39 techniques for compounds of the invention are provided elsewhere in this specification for convenience. Again, all reagents and reaction conditions employed in synthesis are known to those skilled in the art and are available from ordinary commercial sources.

The syntheses of compounds of this invention are illustrated by, but not limited to the following Preparations (for starting materials and intermediates) and Examples (for compounds of formula (I)).

Preparation 1

Preparation of
2-Amino-4-methylthiazole-5-carboxylic Acid Benzylamide

A. A mixture of ethyl 2-amino-4-methylthiazole-5-carboxylate (6.58 g, 35.5 mmol) and NaOH (5.40 g, 135.00 mmol) in tetrahydrofuran (60 mL) and water (30 mL) was heated to reflux overnight. Tetrahydrofuran was removed by evaporation, and the residue was neutralized with 5% hydrochloric acid solution to pH 5~6. The precipitate obtained was collected by filtration and dried to afford 2-amino-4-methylthiazole-5-carboxylic acid (5.20 g, 94%); $^1$H NMR (DMSO-$d_6$, 300 MHz) δ 7.63 (s, 2H), 2.30 (s, 3H). MS (ES+) m/z 159.1 (M+1).

B. To a suspension of 2-amino-4-methylthiazole-5-carboxylic acid (5.20 g, 32.90 mmol) and di-iso-propylethylamine (15.00 mL, 86.70 mmol) in N,N-dimethylformamide (40 mL) was added N-(3-dimethylaminopropyl)-N'-ethylcarbodiimide hydrochloride (8.18 g, 42.70 mmol). The resulting mixture was stirred for 30 min, then 1-hydroxybenzotriazole hydrate (5.78 g, 42.70 mmol) was added, and followed by the addition of benzylamine (4.30 mL, 39.30 mmol). The reaction mixture was stirred at ambient temperature for 2 days, then diluted with ethyl acetate, washed with water and brine, dried over anhydrous sodium sulfate and filtered. The filtrate was concentrated in vacuo. The residue was purified by column chromatography to afford the title compound in 60% yield (4.90 g); $^1$H NMR (DMSO-$d_6$, 300 MHz) δ 7.36-7.25 (m, 5H), 5.79 (s, br, 1H), 5.36 (s, br, 2H), 4.54 (dd, J=5.7 Hz, 2H), 2.47 (s, 3H). MS (ES+) m/z 248.4 (M+1).

Preparation 2

Preparation of
2-Amino-4-trifluoromethylthiazole-5-carboxylic Acid Benzylamide

Following the procedure as described in Preparation 1, making variation only as required to use 2-amino-4-(trifluoromethyl)thiazole-5-carboxylate to replace 2-amino-4-methylthiazole-5-carboxylate, the title compound was obtained as a white solid in 55% yield (1.48 g); $^1$H NMR (CDCl$_3$, 300 MHz) δ 9.30 (t, J=5.5 Hz, 1H), 7.77 (s, 2H), 7.30-7.10 (m, 15H), 4.38 (d, J=5.5 Hz, 2H). MS (ES+) m/z 302.2 (M+1).

Preparation 3

Preparation of
2-Amino-4-methylthiazole-5-carboxylic Acid 4-Chlorobenzylamide

Following the procedure as described in Preparation 1, making variation only as required to use 4-chlorobenzylamine to replace benzylamine to react with 2-amino-4-methylthiazole-5-carboxylic acid, the title compound was

40 obtained as a white solid in 15% yield; $^1$H NMR (CD$_3$OD, 300 MHz) δ 7.26-7.32 (m, 4H), 4.41 (s, 2H), 2.38 (s, 3H). MS (ES+) m/z 282.1 (M+1).

Preparation 4

Preparation of
4-Amino-2-benzamidothiazole-5-carboxylic Acid

A. To a solution of benzoyl isothiocyanate (4.00 mL, 29.70 mmol) and cyanamide (1.37 g, 32.50 mmol) in tetrahydrofuran (80 mL) was added 1,8-diazabicyclo[5.4.0]undec-7-ene (4.90 mL, 32.80 mmol) at 0° C. The resulting reaction mixture was stirred at ambient temperature for 3 hours. Methyl bromoacetate (3.00 mL, 32.00 mmol) was added to the reaction mixture. The reaction mixture was kept stirring for 1 hour at ambient temperature. Another portion of 1,8-diazabicyclo[5.4.0]undec-7-ene (4.90 mL, 32.80 mmol) was added. The reaction mixture was stirred at ambient temperature for another 16 hours. The solvent was removed in vacuo, and the residue was dissolved in ethyl acetate (200 mL), washed with brine, dried over anhydrous sodium sulfate and filtered. The filtrate was concentrated and the residue was purified by column chromatography to give methyl 4-amino-2-benzamidothiazole-5-carboxylate (0.16 g, 2%); $^1$H NMR (CDCl$_3$, 300 MHz) δ 7.60-7.41 (m, 5H), 5.43 (s, 2H), 3.95 (s, 3H); MS (ES+) m/z 277.3 (M+1).

B. To a solution of methyl 4-amino-2-benzamidothiazole-5-carboxylate (0.16 g, 0.57 mmol) in tetrahydrofuran (10 mL) and water (5 mL) was added lithium hydroxide monohydrate (0.007 g, 1.60 mmol). The reaction mixture was stirred at ambient temperature for 16 hours and adjusted to pH 5~6 with 5% hydrochloric acid. The mixture was extracted with ethyl acetate (3×100 mL) and the combined organic extract was washed with brine, dried over anhydrous sodium sulfate and filtered. The filtrate was concentrated to afford the title compound (0.14 g, 88%); MS (ES+) m/z 263.4 (M+1).

Preparation 5

Preparation of 4-(2-oxopyridin-1(2H)-yl)benzoic acid

A. A mixture of 4-bromobenzoic acid ethyl ester (4.58 g, 20.00 mmol), 2-hydroxypyridine (0.95 g, 10.00 mmol), potassium carbonate (1.39 g, 10.00 mmol), and CuI (0.095 g, 0.50 mmol) was stirred at 120° C. for 6 h under a nitrogen atmosphere. The diluted aqueous ammonia (50 mL) was added, and the solution was extracted with ethyl acetate (3×50 mL). The organic extracts were dried over anhydrous sodium sulfate, filtered. The solvent was removed in vacuo to afford ethyl 4-(2-oxopyridin-1(2H)-yl)benzoate in 86% yield (2.10 g); NMR (CDCl$_3$, 300 MHz) δ 8.15 (d, J=8.5 Hz, 2H), 7.46 (d, J=8.5 Hz, 2H), 7.39 (ddd, J=2.0, 6.6, 9.0 Hz, 1H), 7.31 (dd, J=2.0, 6.6 Hz, 1H), 6.65 (d, J=9.0 Hz, 1H), 6.26 (dt, J=1.1, 6.6 Hz, 1H), 4.38 (q, J=7.1 Hz, 2H), 1.39 (t, J=7.1 Hz, 3H).

B. A mixture of ethyl 4-(2-oxopyridin-1(2H)-yl)benzoate (0.40 g, 1.64 mmol) and lithium hydroxide (0.28 g, 6.60 mmol) in tetrahydrofuran/water mixture was stirred at 70° C. for 1 h. The organic solvent was removed in vacuo. The water layer was washed with ethyl acetate (25 mL) and then acidified by addition of 15% hydrochloric acid solution. The solid obtained was collected by filtration, washed with water and dried in air to afford the title compound in 85% yield (0.30 g); $^1$H NMR (300 MHz, DMSO-$d_6$) δ 13.14 (s, 1H), 8.02 (d, J=8.4 Hz, 2H), 7.65 (dd, J=1.9, 6.9 Hz, 1H), 7.51 (d, J=8.5 Hz, 2H), 7.48 (dd, J=1.9, 6.9 Hz, 1H), 6.47 (d, J=9.2 Hz, 1H), 6.31 (dt, J=1.0, 6.9 Hz, 1H).

Preparation 6

Preparation of 2-Amino-4-benzylthiazole-5-carboxylic Acid Benzylamide

To a solution of 2-amino-4-benzylthiazole-5-carboxylic acid (0.033 g, 0.14 mmol) and diisopropylethylamine (0.08 mL, 0.46 mmol) in N,N-dimethylformamide (5 mL) was added N-ethyl-N'-(3-dimethylaminopropyl)carbodiimide hydrochloride (0.039 g, 0.20 mmol), followed by the addition of 1-hydroxybenzotriazole (0.026 g, 0.19 mmol). After 30 minutes, benzylamine (0.02 mL, 0.18 mmol) was added. The reaction mixture was stirred at ambient temperature for 12 h, diluted with ethyl acetate, washed with water, brine, dried over anhydrous $Na_2SO_4$, filtered and concentrated in vacuo. The crude product was purified by flash column chromatography eluting with ethyl acetate/hexanes (5/95 to 100/0) to afford the title compound (0.029 g, 65% yield).

Preparation 7

Preparation of 2-(Isonicotinamido)-4-methylthiazole-5-carboxylic Acid

A mixture of ethyl 2-(isonicotinamido)-4-methylthiazole-5-carboxylate (1.46 g, 5.0 mmol) and sodium hydroxide (0.40 g, 10.00 mmol) in methanol (100 mL) and water (25 mL) was stirred at ambient temperature overnight and then heated to reflux for 2 h. The mixture was concentrated and then neutralized with 5% hydrochloric acid solution to pH 5~6. The precipitate obtained was collected by filtration and dried to give the title compound in 89% yield (1.17 g); $^1$H NMR (DMSO-$d_5$, 300 MHz) δ 8.74 (d, J=6.0 Hz, 2H), 7.93 (d, J=6.0 Hz, 2H), 2.46 (s, 3H); MS (ES+) m/z 264.1 (M+1).

Preparation 8

Preparation of 2-Benzoylamino-4-phenylthiazole-5-carboxylic Acid

A mixture of ethyl 2-benzamido-4-phenylthiazole-5-carboxylate (1.62 g, 4.60 mmol) and lithium hydroxide (0.96 g, 23.00 mmol) was stirred at 50° C. in tetrahydrofuran/water mixture for 96 h. The organic solvent was removed in vacuo and the water layer was washed with ethyl acetate and then acidified by the addition of 15% hydrochloric acid solution to pH 5. The white precipitate obtained was collected by filtration and dried to afford 0.89 g of the title compound in 59% yield; $^1$H NMR (CDCl$_3$, 300 MHz) δ 13.05 (s, 1H), 8.09 (d, J=7.1 Hz, 2H), 7.80-7.35 (m, 8H); MS (ES+) m/z 325.1 (M+1).

Preparation 9

Preparation of 2-Benzoylamino-4-chlorothiazole-5-carboxylic Acid

A. Benzoyl chloride (1.25 mL, 10.70 mmol) was added to a solution of 2-amino-4-chlorothiazole-5-carbaldehyde (1.63 g, 10.00 mmol), pyridine (79.10, 12.30 mmol) and 4-dimethylaminopyridine (10 mg) in tetrahydrofuran (100 mL) at 0° C. The reaction mixture was stirred at ambient temperature overnight and then concentrated. Purification of the residue by column chromatography afforded N-(4-chloro-5-formylthiazol-2-yl)benzamide in 19% yield (0.52 g); $^1$H NMR (CDCl$_3$, 300 MHz) δ 10.0 (s, 1H), 8.28-7.45 (m, 5H); MS (ES+) m/z 267.1 (M+1).

B. A solution of sodium chlorite (2.20 g, 19.40 mmol) and NaH$_2$PO$_4$ (2.32 g, 19.10 mmol) in water (10 mL) was added to a mixture of N-(4-chloro-5-formylthiazol-2-yl)benzamide (0.52 g, 1.95 mmol) in acetonitrile (20 mL), t-BuOH (20 mL) and 2-methyl-2-butene (4 mL) at 0° C. The mixture was stirred for 1 h, then extracted with chloroform, dried over anhydrous sodium sulfate and filtered. The filtrate was concentrated to give the crude product in 17% yield (0.097 g), which was used for next step without purification; MS (ES+) m/z 283.3 (M+1).

Preparation 10

Preparation of 2-Benzamido-4-methylthiazole-5-carboxylic Acid

A mixture of ethyl 2-benzamido-4-methylthiazole-5-carboxylate (3.00 g, 10.00 mmol) and lithium hydroxide (2.50 g, 103.00 mmol) in a mixture of tetrahydrofuran (40 mL) and water (10 mL) was stirred at 50° C. for 20 h. The mixture was then cooled to 0° C. and neutralized with acetic acid to pH 7. The precipitate obtained was collected by filtration, washed with water and dried in vacuo to afford the title compound as a white solid in 75% yield (2.0 g); $^1$H NMR (DMSO-$d_6$, 300 MHz) δ 12.92 (s, br, 1H), 8.06-8.04 (m, 2H), 7.63-7.48 (m, 3H), 2.53 (s, 3H).

Example 1

Synthesis of N-(5-Benzylcarbamoyl-4-methylthiazol-2-yl)isonicotinamide

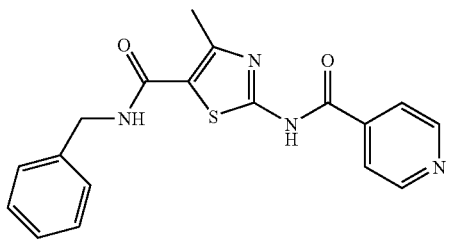 [SMILES: Cc1nc(NC(=O)c2ccncc2)sc1C(=O)NCc1ccccc1]

To a mixture of 4-methyl-2-[(pyridine-4-carbonyl)amino] thiazole-5-carboxylic acid (0.40 g, 1.50 mmol) and 4-methylmorpholine (0.25 mL, 2.20 mmol) in tetrahydrofuran (50 mL) was added 2-chloro-4,6-dimethoxy-1,3,5-triazine (0.32 g, 1.80 mmol). The resulting mixture was stirred at ambient temperature for 4 h, and then benzylamine (0.2 mL, 1.80 mmol) was added. The reaction mixture was stirred at room temperature for 47 h and then concentrated. Purification of the residue by column chromatography afforded the title compound in 45% yield (0.24 g); m.p. 171-172° C.; $^1$H NMR (DMSO-$d_6$, 300 MHz) δ 13.15 (s, 1H), 8.78-8.63 (m, 3H), 7.94 (dd, J=1.5, 4.5 Hz, 2H), 7.32-7.17 (m, 5H), 4.38 (d, J=6.0 Hz, 2H), 2.51 (s, 3H); $^{13}$C NMR (DMSO-$d_6$, 75 MHz) δ 162.0, 150.9, 140.0, 139.5, 128.7, 127.7, 127.2, 122.2, 114.3, 43.1, 17.1; MS (ES+) m/z 353.3 (M+1).

Example 1.1

Synthesis of N-(4-Methyl-5-phenethylcarbamoylthiazol-2-yl)isonicotinamide

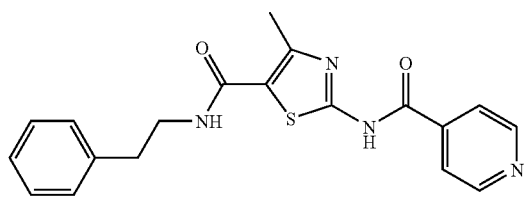 [SMILES: Cc1nc(NC(=O)c2ccncc2)sc1C(=O)NCCc1ccccc1]

Following the procedure as described in Example 1, making variations only as required to use phenethylamine in place of benzylamine to react with 4-methyl-2-[(pyridine-4-carbonyl)amino]thiazole-5-carboxylic acid, the title compound was obtained as a white solid in 34% yield; $^1$H NMR (DMSO-$d_6$, 300 MHz) δ 13.2 (s, br, 1H), 8.89-8.66 (m, 2H), 8.16-7.88 (m, 3H), 7.29-7.14 (m, 5H), 3.47-3.32 (m, 2H), 2.81-2.65 (m, 2H), 2.46 (s, 3H); MS (ES+) m/z 367.2 (M+1).

Example 1.2

Synthesis of N-[4-Methyl-5-(3-phenylpropylcarbamoyl)thiazol-2-yl]isonicotinamide

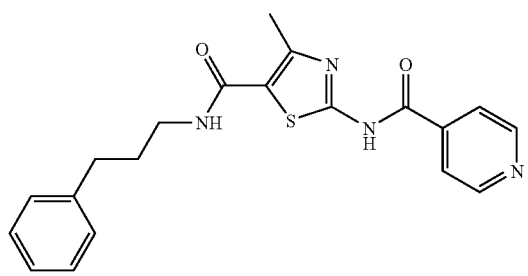 [SMILES: Cc1nc(NC(=O)c2ccncc2)sc1C(=O)NCCCc1ccccc1]

Following the procedure as described in Example 1, making variations only as required to use 3-phenylpropylamine in place of benzylamine to react with 4-methyl-2-[(pyridine-4-carbonyl)amino]thiazole-5-carboxylic acid, the title compound was obtained as a white solid in 22% yield; $^1$H NMR (DMSO-$d_6$, 300 MHz) δ 8.78-8.76 (m, 2H), 8.13-7.93 (m, 3H), 7.27-7.11 (m, 5H), 3.32-3.11 (m, 2H), 2.70-2.46 (m, 5H), 1.84-1.72 (m, 2H); MS (ES+) m/z 381.1 (M+1).

Example 1.3

Synthesis of N-[5-(2-Cyclopropylethylcarbamoyl)-4-methylthiazol-2-yl]isonicotinamide

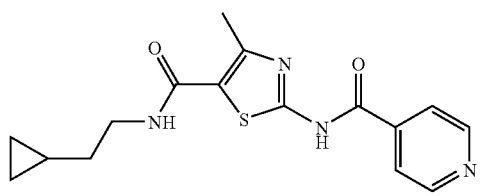 [SMILES: Cc1nc(NC(=O)c2ccncc2)sc1C(=O)NCCC1CC1]

Following the procedure as described in Example 1, making variations only as required to use 2-cyclopropylethylamine in place of benzylamine to react with 4-methyl-2-[(pyridine-4-carbonyl)amino]thiazole-5-carboxylic acid, the title compound was obtained as a white solid in 20% yield; $^1$H NMR (DMSO-$d_6$, 300 MHz) δ 8.82-8.80 (m, 2H), 8.08-7.72 (m, 3H), 3.27-3.16 (m, 2H), 2.45 (s, 3H), 1.41-1.34 (m, 2H), 0.73-0.65 (m, 1H), 0.48-0.25 (m, 2H), 0.12-0.80 (m, 2H); MS (ES+) m/z 331.1 (M+1).

Example 1.4

Synthesis of 2-Benzoylamino-4-phenylthiazole-5-carboxylic Acid Benzylamide

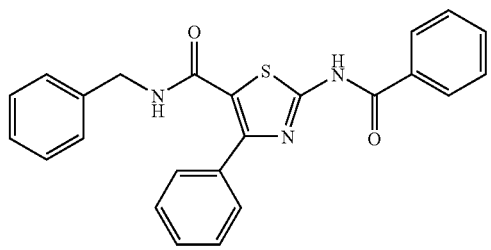 [SMILES: O=C(Nc1nc(-c2ccccc2)c(C(=O)NCc2ccccc2)s1)c1ccccc1]

Following the procedure as described in Example 1, making variations only as required to use 2-amino-4-phenylthiazole-5-carboxylic acid in place of 4-methyl-2-[(pyridine-4-carbonyl)amino]thiazole-5-carboxylic acid to react with benzylamine, the title compound was obtained as a white solid in 89% yield; $^1$H NMR (CDCl$_3$, 300 MHz) δ 12.96 (s, 1H), 8.77 (t, J=5.9 Hz, 1H), 8.11 (d, J=7.3 Hz, 1H), 7.65-7.60 (m, 3H), 7.53 (t, J=7.5 Hz, 1H), 7.40-7.20 (m, 8H), 4.36 (d, J=5.9 Hz, 1H); $^{13}$C NMR (CDCl$_3$, 75 MHz) δ 166.0, 162.4, 157.5, 148.9, 139.3, 134.6, 133.4, 132.0, 129.1, 129.0, 128.8, 128.6, 127.9, 127.4, 121.3, 43.4; MS (ES+) m/z 414.1 (M+1).

Example 2

Synthesis of 2-Benzoylamino-4-methylthiazole-5-carboxylic Acid Benzylamide

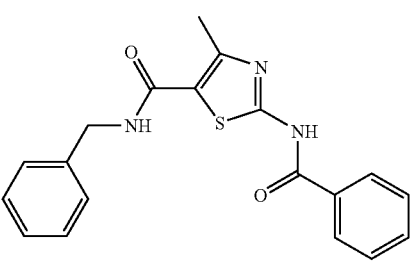 [SMILES: Cc1nc(NC(=O)c2ccccc2)sc1C(=O)NCc1ccccc1]

Benzoyl chloride (0.04 mL, 0.36 mmol) was added to a mixture of 2-amino-4-methylthiazole-5-carboxylic acid benzylamide (0.083 g, 0.033 mmol), 4-dimethylamino-pyridine (10 mg) and triethylamine (0.06 mL, 0.43 mmol) in tetrahydrofuran (10 mL) at 0° C. The reaction mixture was stirred at ambient temperature for 8 h, then concentrated. The residue was purified by column chromatography to afford the title compound in 75% yield (87 mg); $^1$H NMR (CDCl$_3$, 300

MHz) δ 7.90-7.24 (m, 11H), 5.97 (s, br, 1H), 4.59 (d, J=5.8 Hz, 2H), 2.45 (s, 3H); MS (ES+) m/z 352.0 (M+1).

Example 2.1

Synthesis of 4-Methyl-2-propionylaminothiazole-5-carboxylic Acid Benzylamide

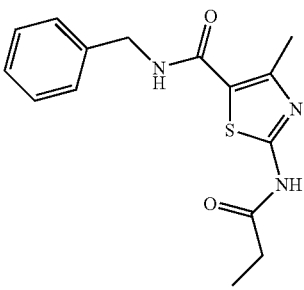 [SMILES: CCC(=O)Nc1nc(C)c(C(=O)NCc2ccccc2)s1]

Following the procedure as described in Example 2, making variations only as required to use propionyl chloride in place of benzoyl chloride to react with 2-amino-4-methylthiazole-5-carboxylic acid benzylamide, the title compound was obtained as a white solid in 31% yield; m. p. 175-176° C.; $^1$H NMR (DMSO-d$_6$, 300 MHz) δ 12.15, (s, 1H), 8.51 (t, J=6.0 Hz, 1H), 7.32-7.16 (m, 5H), 4.34 (d, J=6.0 Hz, 2H), 2.65-2.22 (m, 5H), 1.07 (t, J=7.5 Hz, 3H); MS (ES+) m/z 304.3 (M+1).

Example 2.2

Synthesis of 2-(Cyclopropanecarbonylamino)-4-methylthiazole-5-carboxylic Acid Benzylamide

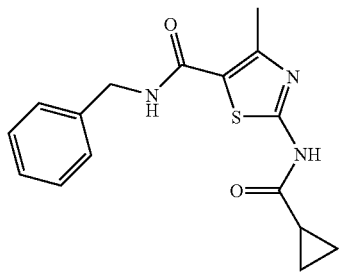 [SMILES: Cc1nc(NC(=O)C2CC2)sc1C(=O)NCc1ccccc1]

Following the procedure as described in Example 2, making variations only as required to use cyclopropanecarbonyl chloride in place of benzoyl chloride to react with 2-amino-4-methylthiazole-5-carboxylic acid benzylamide, the title compound was obtained as a white solid in 87% yield; m. p. 241-243° C.; $^1$H NMR (DMSO-d$_6$, 300 MHz) δ 12.5 (s, 1H), 8.49 (t, J=6.0 Hz, 1H), 7.31-7.17 (m, 5H), 4.34 (d, J=6.0 Hz, 2H), 1.94-1.84 (m, 1H), 1.15-1.08 (m, 4H); $^{13}$C NMR (DMSO-d$_6$, 75 MHz) δ 172.7, 162.2, 157.3, 151.0, 140.1, 128.7, 127.6, 127.1, 118.8, 43.0, 17.4, 14.1, 9.0; MS (ES+) m/z 316.3 (M+1).

Example 2.3

Synthesis of 2-(2,5-Difluorobenzoylamino)-4-methylthiazole-5-carboxylic Acid Benzylamide

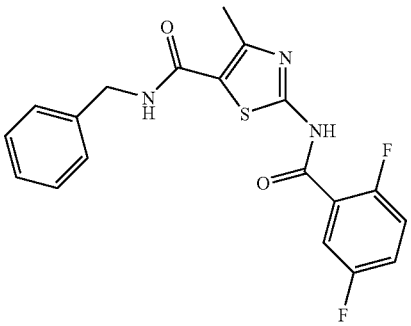 [SMILES: Cc1nc(NC(=O)c2cc(F)ccc2F)sc1C(=O)NCc1ccccc1]

Following the procedure as described in Example 2, making variations only as required to use 2,5-difluorobenzoyl chloride in place of benzoyl chloride to react with 2-amino-4-methylthiazole-5-carboxylic acid benzylamide, the title compound was obtained as a white solid in 86% yield; $^1$H NMR (DMSO-d$_6$, 300 MHz) δ 8.63 (t, J=5.8 Hz, 1H), 7.60-7.17 (m, 8H), 4.36 (d, J=5.8 Hz, 2H), 2.51 (s, 3H); MS (ES+) m/z 388.2 (M+1).

Example 2.4

Synthesis of 2-(2,2-Dimethylpropionylamino)-4-methylthiazole-5-carboxylic Acid Benzylamide

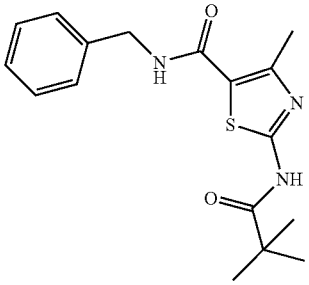 [SMILES: Cc1nc(NC(=O)C(C)(C)C)sc1C(=O)NCc1ccccc1]

Following the procedure as described in Example 2, making variations only as required to use 2,2-dimethylpropionyl chloride in place of benzoyl chloride to react with 2-amino-4-methylthiazole-5-carboxylic acid benzylamide, the title compound was obtained as a white solid in 23% yield; $^1$H NMR (CDCl$_3$, 300 MHz) δ 8.85 (s, br, 1H), 7.36-7.25 (m, 5H), 5.91 (s, br, 1H), 4.56 (d, J=5.8 Hz, 2H), 2.60 (s, 3H), 1.27 (s, 9H); MS (ES+) m/z 332.0 (M+1).

Example 2.5

Synthesis of 2-(Cyclobutanecarbonylamino)-4-methylthiazole-5-carboxylic acid benzylamide

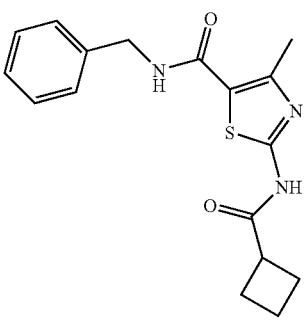 [SMILES: Cc1nc(NC(=O)C2CCC2)sc1C(=O)NCc1ccccc1]

Following the procedure as described in Example 2, making variations only as required to use cyclobutanecarbonyl chloride in place of benzoyl chloride to react with 2-amino-4-methylthiazole-5-carboxylic acid benzylamide, the title compound was obtained as a white solid in 46% yield; $^1$H NMR (DMSO-d$_5$, 300 MHz) δ 7.38-7.25 (m, 4H), 5.96 (s, br, 1H), 4.58-4.50 (m, 2H), 3.25-3.14 (m, 1H), 2.53 (s, 3H), 2.42-1.90 (m, 6H); MS (ES+) m/z 330.0 (M+1).

Example 2.6

Synthesis of 4-Methyl-2-[(2-phenylcyclopropanecarbonyl)amino]thiazole-5-carboxylic Acid Benzylamide

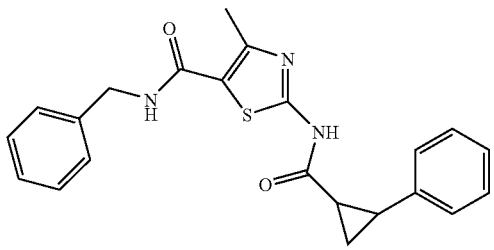 [SMILES: Cc1nc(NC(=O)C2CC2c2ccccc2)sc1C(=O)NCc1ccccc1]

Following the procedure as described in Example 2, making variations only as required to use 2-phenylcyclopropanecarbonyl chloride in place of benzoyl chloride to react with 2-amino-4-methylthiazole-5-carboxylic acid benzylamide, the title compound was obtained as a white solid in 73% yield; $^1$H NMR (DMSO-d$_6$, 300 MHz) δ 7.38-7.03 (m, 10H), 5.87 (s, br, 1H), 4.56-4.50 (m, 2H), 2.70-2.63 (m, 1H), 2.41 (s, 3H), 1.81-1.73 (m, 2H), 1.52-1.23 (m, 1H); MS (ES+) m/z 391.8 (M+1).

Example 2.7

Synthesis of 2-(2-Fluorobenzoylamino)-4-methylthiazole-5-carboxylic Acid Benzylamide

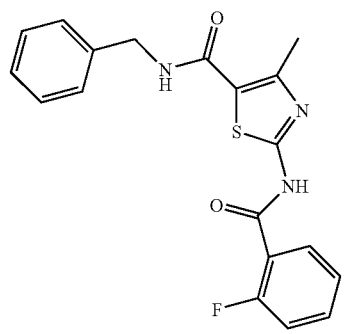 [SMILES: Cc1nc(NC(=O)c2ccccc2F)sc1C(=O)NCc1ccccc1]

Following the procedure as described in Example 2, making variations only as required to use 2-fluorobenzoyl chloride in place of benzoyl chloride to react with 2-amino-4-methylthiazole-5-carboxylic acid benzylamide, the title compound was obtained as a white solid in 99% yield; $^1$H NMR (CDCl$_3$, 300 MHz) δ 8.63 (t, J=5.8 Hz, 1H), 7.62-7.17 (m, 9H), 6.01 (s, br, 1H), 4.59 (d, J=5.8 Hz, 2H), 2.61 (s, 3H); MS (ES+) m/z 369.7 (M+1).

Example 2.8

Synthesis of 2-(Cyclopentanecarbonylamino)-4-methylthiazole-5-carboxylic Acid Benzylamide

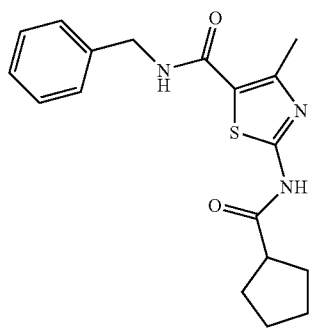 [SMILES: Cc1nc(NC(=O)C2CCCC2)sc1C(=O)NCc1ccccc1]

Following the procedure as described in Example 2, making variations only as required to use cyclopentanecarbonyl chloride in place of benzoyl chloride to react with 2-amino-4-methylthiazole-5-carboxylic acid benzylamide, the title compound was obtained as a white solid in 38% yield; $^1$H NMR (CDCl$_3$, 300 MHz) δ 9.56 (s, br, 1H), 7.35-7.24 (m, 5H), 5.92 (s, br, 1H), 4.56 (d, J=5.7 Hz, 2H), 2.81-2.69 (m, 1H), 2.62 (s, 3H), 1.97-1.72 (m, 8H); MS (ES+) m/z 344.2 (M+1).

Example 2.9

Synthesis of 4-Methyl-2-(2-trifluoromethylbenzoylamino)thiazole-5-carboxylic Acid Benzylamide

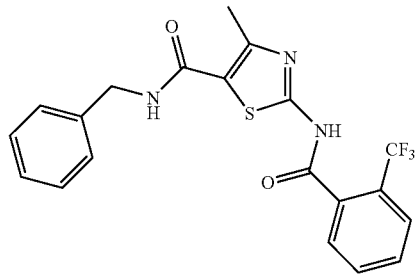 [SMILES: Cc1nc(NC(=O)c2ccccc2C(F)(F)F)sc1C(=O)NCc1ccccc1]

Following the procedure as described in Example 2, making variations only as required to use 2-trifluoromethylbenzoyl chloride in place of benzoyl chloride to react with 2-amino-4-methylthiazole-5-carboxylic acid benzylamide, the title compound was obtained as a white solid in 36% yield; $^1$H NMR (CDCl$_3$, 300 MHz) δ 7.79-7.26 (m, 10H), 5.94 (s, br, 1H), 4.59 (d, J=5.8 Hz, 2H), 2.22 (s, 3H); MS (ES+) m/z 420.0 (M+1).

Example 2.10

Synthesis of 2-(Cyclopropanecarbonylamino)-4-methylthiazole-5-carboxylic Acid 4-Chlorobenzylamide

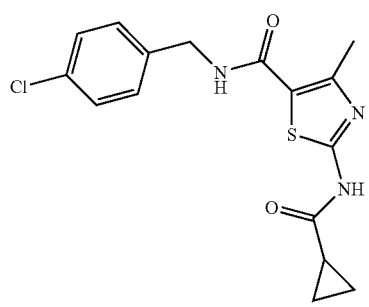 [SMILES: Cc1nc(NC(=O)C2CC2)sc1C(=O)NCc1ccc(Cl)cc1]

Following the procedure as described in Example 2, making variations only as required to use cyclopropanecarbonyl chloride in place of benzoyl chloride to react with 2-amino-4-methylthiazole-5-carboxylic acid 4-chlorobenzylamide, the title compound was obtained as a white solid in 55% yield; $^1$H NMR (DMSO-d$_6$, 300 MHz) δ 8.51 (t, J=6.0 Hz, 1H), 7.36-7.25 (m, 4H), 4.32 (d, J=6.0 Hz, 2H), 2.50 (s, 3H), 1.94-1.84 (m, 1H), 0.93-0.87 (m, 4H); MS (ES+) m/z 350.1 (M+1).

Example 2.11

Synthesis of N-[5-(4-Chlorobenzylcarbamoyl)-4-methylthiazol-2-yl]isonicotinamide

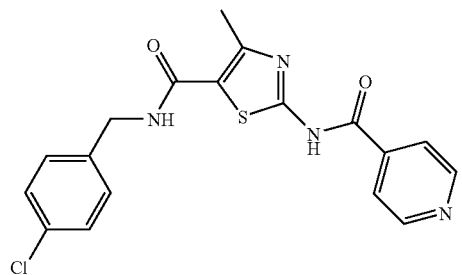 [SMILES: Cc1nc(NC(=O)c2ccncc2)sc1C(=O)NCc1ccc(Cl)cc1]

Following the procedure as described in Example 2, making variations only as required to use isonicotinoyl chloride hydrochloride in place of benzoyl chloride to react with 2-amino-4-methylthiazole-5-carboxylic acid 4-chlorobenzylamide, the title compound was obtained as a white solid in 99% yield; $^1$H NMR (DMSO-d$_6$, 300 MHz) δ 8.75-8.73 (m, 2H), 7.95-7.93 (m, 2H), 7.34 (s, 2H), 7.31 (s; 2H), 4.86 (s, 2H), 2.54 (s, 3H); MS (ES+) m/z 387.0 (M+1).

Example 2.12

Synthesis of 2-Benzoylamino-4-trifluoromethylthiazole-5-carboxylic Acid Benzylamide

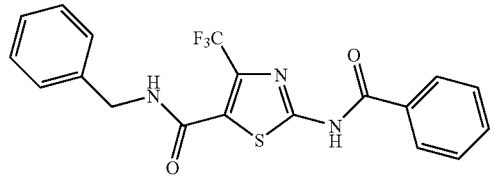 [SMILES: O=C(Nc1nc(C(F)(F)F)c(C(=O)NCc2ccccc2)s1)c1ccccc1]

Following the procedure as described in Example 2, making variations only as required to use 2-amino-4-trifluoromethylthiazole-5-carboxylic acid benzylamide in place of 2-amino-4-methylthiazole-5-carboxylic acid 4-chlorobenzylamide to react with benzoyl chloride, the title compound was obtained as a white solid in 62% yield; $^1$H NMR (CDCl$_3$, 300 MHz) δ 13.28 (t, J=6.2 Hz, 1H), 9.30-9.25 (m, 1H), 8.10-8.08 (m, 2H), 7.65-7.50 (m, 3H), 7.35-7.20 (m, 5H), 4.40-4.35 (m, 2H); $^{13}$C NMR (CDCl$_3$, 75 MHz) δ 166.4, 159.5, 158.7, 139.1, 136.2, 135.7, 133.7, 131.4, 129.2, 128.8, 127.7, 127.5, 122.9, 119.3, 43.4; MS (ES+) m/z 406.1 (M+1).

Example 2.13

Synthesis of 2-[(4-Pentylbenzoyl)amino]-N-(phenylmethyl)-4-(trifluoromethyl)-5-thiazolecarboxamide

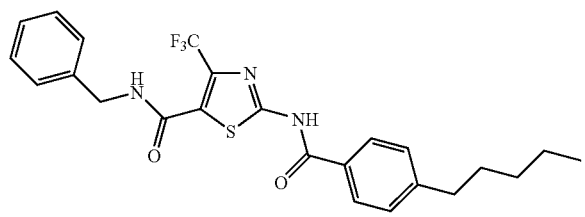 [SMILES: CCCCCc1ccc(C(=O)Nc2nc(C(F)(F)F)c(C(=O)NCc3ccccc3)s2)cc1]

Following the procedure as described in Example 2, making variations only as required to use 2-amino-4-trifluoromethylthiazole-5-carboxylic acid benzylamide in place of 2-amino-4-methylthiazole-5-carboxylic acid 4-chlorobenzylamide to react with 4-pentylbenzoyl chloride, the title compound was obtained as a white solid in 89% yield; $^1$H NMR (CDCl$_3$, 300 MHz) δ 13.18 (s, 1H), 9.28 (t, J=5.8 Hz, 1H), 8.02 (d, J=8.1 Hz, 2H), 7.36-7.23 (m, 7H), 4.41 (d, J=5.8 Hz, 2H), 2.61 (t, J=7.4 Hz, 2H), 1.58-1.51 (m, 2H), 1.26-1.20 (m, 4H), 0.81 (t, J=6.8 Hz, 3H); $^{13}$C NMR (CDCl$_3$, 75 MHz) δ 166.2, 148.9, 139.1, 159.5, 158.7, 129.1, 128.9, 128.8, 127.9, 127.8, 127.7, 127.5, 43.4, 35.5, 31.3, 30.7, 22.4, 14.3; MS (ES+) m/z 476.1 (M+1).

Example 2.14

Synthesis of 2-(4-Fluorobenzoylamino)-4-methylthiazole-5-carboxylic Acid Benzylamide

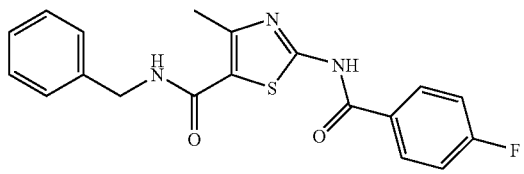 [SMILES: Cc1nc(NC(=O)c2ccc(F)cc2)sc1C(=O)NCc1ccccc1]

Following the procedure as described in Example 2, making variations only as required to use 4-fluorobenzoyl chloride in place of benzoyl chloride to react with 2-amino-4-methylthiazole-5-carboxylic acid benzylamide, the title compound was obtained as a white solid in 30% yield; $^1$H NMR (CDCl$_3$, 300 MHz) δ 7.99-7.94 (dd, J=5.1, 8.8 Hz, 2H), 7.19-7.16 (m, 7H), 5.96 (s, 1H), 4.59 (d, J=4.6 Hz, 2H), 2.56 (s, 3H); MS (ES+) m/z 370.2 (M+1).

Example 2.15

Synthesis of 2-(2,4-Dichlorobenzoylamino)-4-methylthiazole-5-carboxylic Acid Benzylamide

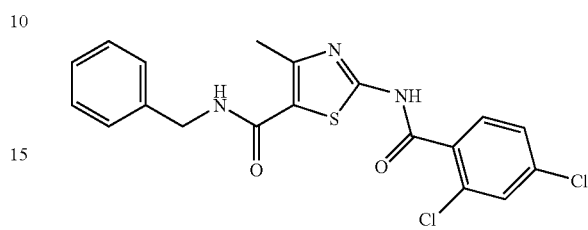

Following the procedure as described in Example 2, making variations only as required to use 2,4-dichlorobenzoyl chloride in place of benzoyl chloride to react with 2-amino-4-methylthiazole-5-carboxylic acid benzylamide, the title compound was obtained as a white solid in 21% yield; $^1$H NMR (CDCl$_3$, 300 MHz) δ 7.74 (d, J=8.3 Hz, 1H), 7.45-7.24 (m, 7H), 5.99 (s, 1H), 4.57 (d, J=5.4 Hz, 2H), 2.35 (s, 3H); MS (ES+) m/z 420.0 (M+1).

Example 2.16

Synthesis of 2-(4-Chlorobenzoylamino)-4-methylthiazole-5-carboxylic Acid Benzylamide

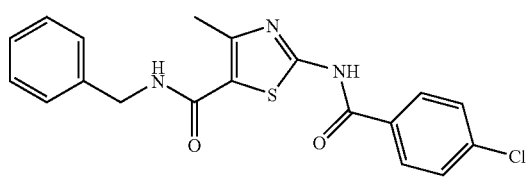 [SMILES: Cc1nc(NC(=O)c2ccc(Cl)cc2)sc1C(=O)NCc1ccccc1]

Following the procedure as described in Example 2, making variations only as required to use 4-chlorobenzoyl chloride in place of benzoyl chloride to react with 2-amino-4-methylthiazole-5-carboxylic acid benzylamide, the title compound was obtained as a white solid in 23% yield; $^1$H NMR (CDCl$_3$, 300 MHz) δ 7.84 (d, J=8.5 Hz, 2H), 7.45 (d, J=8.5 Hz, 2H), 7.32-7.24 (m, 5H), 6.02 (s, 1H), 5.27 (s, 2H), 2.01 (s, 3H); MS (ES+) m/z 386.1 (M+1).

Example 2.17

Synthesis of 4-Methyl-2-(4-trifluoromethylbenzoylamino)thiazole-5-carboxylic Acid Benzylamide

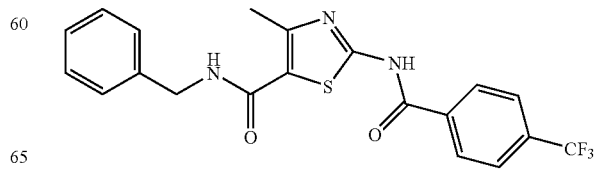

Following the procedure as described in Example 2, making variations only as required to use 4-trifluoromethylbenzoyl chloride in place of benzoyl chloride to react with 2-amino-4-methylthiazole-5-carboxylic acid benzylamide, the title compound was obtained as a white solid in 45% yield; $^1$H NMR (CDCl$_3$, 300 MHz) δ 8.05 (d, J=8.2 Hz, 2H), 7.77 (d, J=8.2 Hz, 2H), 7.36-7.29 (m, 5H), 5.97 (s, 1H), 4.60 (d, J=5.6 Hz, 2H), 2.57 (s, 3H); MS (ES+) m/z 420.1 (M+1).

Example 2.18

Synthesis of 2-(2-Chlorobenzoylamino)-4-methylthiazole-5-carboxylic Acid Benzylamide

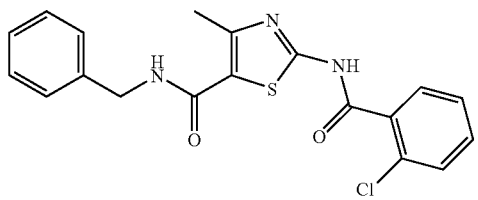 [SMILES: Cc1nc(NC(=O)c2ccccc2Cl)sc1C(=O)NCc1ccccc1]

Following the procedure as described in Example 2, making variations only as required to use 2-chlorobenzoyl chloride in place of benzoyl chloride to react with 2-amino-4-methylthiazole-5-carboxylic acid benzylamide, the title compound was obtained as a white solid in 13% yield; $^1$H NMR (CDCl$_3$, 300 MHz) δ 7.78 (d, J=7.8 Hz, 1H), 7.46-7.27 (m, 8H), 5.95 (s, 1H), 4.57 (d, J=4.6 Hz, 2H), 2.33 (s, 3H); MS (ES+) m/z 386.1 (M+1).

Example 2.19

Synthesis of 2-(3-Chlorobenzoylamino)-4-methylthiazole-5-carboxylic Acid Benzylamide

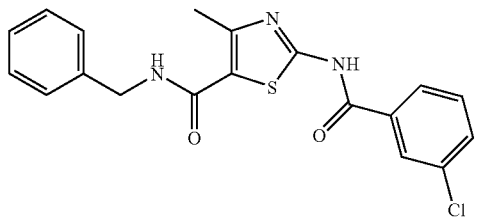 [SMILES: Cc1nc(NC(=O)c2cccc(Cl)c2)sc1C(=O)NCc1ccccc1]

Following the procedure as described in Example 2, making variations only as required to use 3-chlorobenzoyl chloride in place of benzoyl chloride to react with 2-amino-4-methylthiazole-5-carboxylic acid benzylamide, the title compound was obtained as a white solid in 32% yield; m.p. 178-179° C.; $^1$H NMR (CDCl$_3$, 300 MHz) δ 8.05 (t, J=1.6 Hz, 1H), 7.86 (ddd, J=1.1, 1.6, and 7.8 Hz, 1H), 7.59-7.27 (m, 7H), 5.98 (t, J=5.3 Hz, 1H), 4.59 (d, J=5.6 Hz, 2H), 2.57 (s, 3H); MS (ES+) m/z 386 (M+1).

Example 2.20

Synthesis of 2-(2-Chloro-4-fluorobenzoylamino)-4-methylthiazole-5-carboxylic Acid Benzylamide

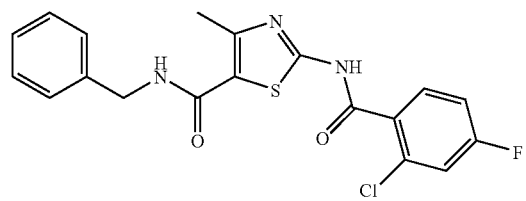 [SMILES: Cc1nc(NC(=O)c2ccc(F)cc2Cl)sc1C(=O)NCc1ccccc1]

Following the procedure as described in Example 2, making variations only as required to use 4-fluorobenzoyl chloride in place of benzoyl chloride to react with 2-amino-4-methylthiazole-5-carboxylic acid benzylamide, the title compound was obtained as a white solid in 28% yield; m.p. 95-96° C.; $^1$H NMR (CDCl$_3$, 300 MHz) δ 7.49 (dd, J=3.1, 8.3 Hz, 1H), 7.39 (dd, J=4.7, 8.9 Hz, 1H), 7.35-7.14 (m, 6H), 5.99 (t, J=5.4 Hz, 1H), 4.57 (d, J=5.4 Hz, 2H), 2.30 (s, 3H); MS (ES+) m/z 404.1 (M+1).

Example 2.21

Synthesis of 4-Methyl-2-(2-trifluoromethoxybenzoylamino)thiazole-5-carboxylic Acid Benzylamide

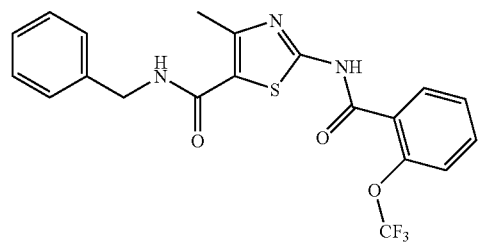 [SMILES: Cc1nc(NC(=O)c2ccccc2OC(F)(F)F)sc1C(=O)NCc1ccccc1]

Following the procedure as described in Example 2, making variations only as required to use 2-trifluoromethoxybenzoyl chloride in place of benzoyl chloride to react with 2-amino-4-methylthiazole-5-carboxylic acid benzylamide, the title compound was obtained as a white solid in 30% yield; m.p. 140-141° C.; $^1$H NMR (CDCl$_3$, 300 MHz) δ 7.98 (dd, J=1.8, 7.8 Hz, 1H), 7.60 (ddd, J=1.8, 7.6, 8.2 Hz, 1H), 7.43 (dt, J=1.0, 7.6 Hz, 1H), 7.46-7.25 (m, 6H), 5.98 (t, J=5.3 Hz, 1H), 4.57 (d, J=5.6 Hz, 2H), 3.1 (s, 3H); MS (ES+) m/z 436 (M+1).

Example 2.22

Synthesis of 4-Methyl-2-(3-trifluoromethylbenzoylamino)thiazole-5-carboxylic Acid Benzylamide

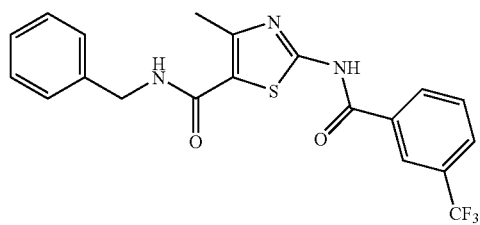 [SMILES: Cc1nc(NC(=O)c2cccc(C(F)(F)F)c2)sc1C(=O)NCc1ccccc1]

Following the procedure as described in Example 2, making variations only as required to use 3-trifluoromethylbenzoyl chloride in place of benzoyl chloride to react with 2-amino-4-methylthiazole-5-carboxylic acid benzylamide, the title compound was obtained as a white solid in 27% yield; m.p. 195-196° C.; $^1$H NMR (CDCl$_3$, 300 MHz) δ 8.15 (s, 1H), 8.07 (d, J=7.8 Hz, 1H), 7.85 (d, J=7.8 Hz, 1H), 7.65 (t, J=7.8 Hz, 1H), 7.40-7.27 (m, 5H), 5.97 (t, J=4.7 Hz, 1H), 4.59 (d, J=5.5 Hz, 2H), 2.49 (s, 3H); MS (ES+) m/z 420 (M+1).

Example 2.23

Synthesis of 4-Methyl-2-[(naphthalene-1-carbonyl)amino]thiazole-5-carboxylic Acid Benzylamide

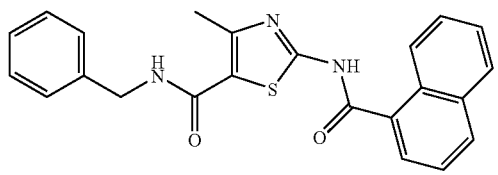 [SMILES: Cc1nc(NC(=O)c2cccc3ccccc23)sc1C(=O)NCc1ccccc1]

Following the procedure as described in Example 2, making variations only as required to use naphthalene-1-carbonyl chloride in place of benzoyl chloride to react with 2-amino-4-methylthiazole-5-carboxylic acid benzylamide, the title compound was obtained as a white solid in 12% yield; m.p. 99-101° C.; $^1$H NMR (CDCl$_3$, 300 MHz) δ 8.40 (d, J=7.5 Hz, 1H), 7.99 (d, J=8.3 Hz, 1H), 7.87 (d, J=7.5 Hz, 1H), 7.85 (d, J=7.5 Hz, 1H), 7.79-7.76 (m, 8H), 5.93 (t, J=5.6 Hz, 1H), 4.57 (d, J=5.6 Hz, 2H), 2.09 (s, 3H); MS (ES+) m/z 402.2 (M+1).

Example 2.24

Synthesis of 2-(3,5-Dichlorobenzoylamino)-4-methylthiazole-5-carboxylic Acid Benzylamide

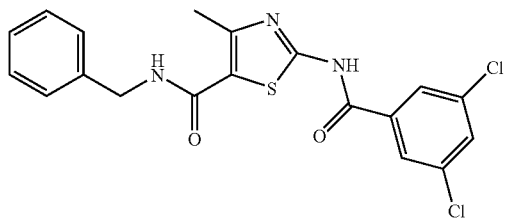 [SMILES: Cc1nc(NC(=O)c2cc(Cl)cc(Cl)c2)sc1C(=O)NCc1ccccc1]

Following the procedure as described in Example 2, making variations only as required to use 3,5-dichlorobenzoyl chloride in place of benzoyl chloride to react with 2-amino-4-methylthiazole-5-carboxylic acid benzylamide, the title compound was obtained as a white solid in 34% yield; m.p. 104-105° C.; $^1$H NMR (CDCl$_3$, 300 MHz) δ 7.69 (d, J=1.9 Hz, 2H), 7.52 (t, J=1.9, 1H), 7.35-7.31 (m, 5H), 6.04 (t, J=5.6 Hz, 1H), 4.59 (d, J=5.6 Hz, 2H), 2.44 (s, 3H); MS (ES+) m/z 420 (M+1).

Example 2.25

Synthesis of 2-(4-Cyanobenzoylamino)-4-methylthiazole-5-carboxylic Acid Benzylamide

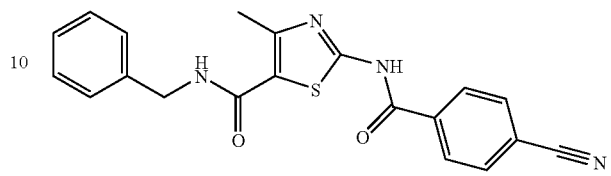

Following the procedure as described in Example 2, making variations only as required to use 4-cyanobenzoyl chloride in place of benzoyl chloride to react with 2-amino-4-methylthiazole-5-carboxylic acid benzylamide, the title compound was obtained as a white solid in 23% yield; m.p. 256-258° C.; $^1$H NMR (DMSO-d$_6$, 300 MHz) δ 8.64 (t, J=5.7 Hz, 1H), 8.19 (d, J=8.2 Hz, 2H), 7.99 (d, J=8.2 Hz, 2H), 7.49-7.18 (m, 5H), 4.37 (d, J=5.7 Hz, 2H), 2.51 (s, 3H); MS (ES+) m/z 377.2 (M+1).

Example 2.26

Synthesis of 2-(3-Cyanobenzoylamino)-4-methylthiazole-5-carboxylic Acid Benzylamide

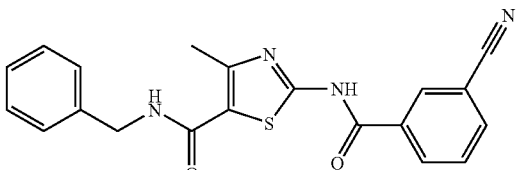

Following the procedure as described in Example 2, making variations only as required to use 3-cyanobenzoyl chloride in place of benzoyl chloride to react with 2-amino-4-methylthiazole-5-carboxylic acid benzylamide, the title compound was obtained as a white solid in 36% yield; m.p. 207-208° C.; $^1$H NMR (CDCl$_3$, 300 MHz) δ 8.21 (s, 1H), 8.11 (d, J=7.8 Hz, 1H), 7.87 (d, J=7.8 Hz, 1H) 7.67-7.58 (m, 1H), 7.36-7.32 (m, 5H), 5.99 (t, J=5.6 Hz, 1H), 4.59 (d, J=5.6 Hz, 2H), 2.53 (s, 3H); MS (ES+) m/z 377.2 (M+1).

Example 2.27

Synthesis of N-(5-Benzylcarbamoyl-4-methylthiazol-2-yl)nicotinamide

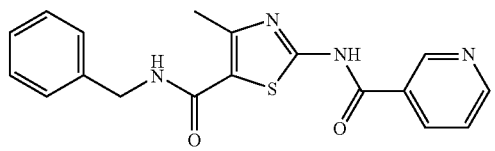 [SMILES: Cc1nc(NC(=O)c2cccnc2)sc1C(=O)NCc1ccccc1]

Following the procedure as described in Example 2, making variations only as required to use nicotinoyl chloride in place of benzoyl chloride to react with 2-amino-4-methylthiazole-5-carboxylic acid benzylamide, the title compound was obtained as a white solid in 33% yield. m.p. 224-226° C.; $^1$H NMR (DMSO-d$_6$, 300 MHz) δ 9.17 (d, J=1.5 Hz, 1H), 8.76 (dd, J=1.5, 4.6 Hz, 1H), 8.63 (t, J=5.7 Hz, 1H), 8.40-8.36 (m, 1H), 7.55 (dd, J=4.6, 8.1 Hz, 1H), 7.33-7.19 (m, 5H), 4.38 (d, J=5.7 Hz, 2H), 2.51 (s, 3H); MS (ES+) m/z 353.2 (M+1).

Example 2.28

Synthesis of 4-Methyl-2-(3-trifluoromethoxybenzoylamino)thiazole-5-carboxylic Acid Benzylamide

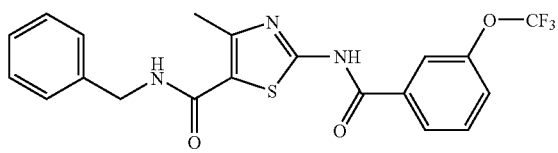 [SMILES: Cc1nc(NC(=O)c2cccc(OC(F)(F)F)c2)sc1C(=O)NCc1ccccc1]

Following the procedure as described in Example 2, making variations only as required to use 3-trifluoromethoxybenzoyl chloride in place of benzoyl chloride to react with 2-amino-4-methylthiazole-5-carboxylic acid benzylamide, the title compound was obtained as a white solid in 28% yield; m.p. 230-232° C.; $^1$H NMR (CDCl$_3$, 300 MHz) δ 7.78 (d, J=7.8 Hz, 1H), 7.76 (s, 1H), 7.54-7.24 (m, 7H), 6.00 (t, J=4.8 Hz, 1H), 4.58 (d, J=5.6 Hz, 2H), 2.38 (s, 3H); MS (ES+) m/z 436.1 (M+1).

Example 2.29

Synthesis of 2-(3,5-Difluorobenzoylamino)-4-methylthiazole-5-carboxylic Acid Benzylamide

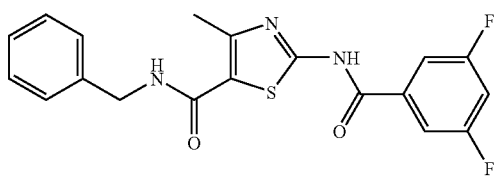 [SMILES: Cc1nc(NC(=O)c2cc(F)cc(F)c2)sc1C(=O)NCc1ccccc1]

Following the procedure as described in Example 2, making variations only as required to use 3,5-difluorobenzoyl chloride in place of benzoyl chloride to react with 2-amino-4-methylthiazole-5-carboxylic acid benzylamide, the title compound was obtained as a white solid in 48% yield; m.p. 84-86° C.; $^1$H NMR (CDCl$_3$, 300 MHz) δ 7.44-7.24 (m, 7H), 7.01 (tt, J=2.2, 8.4 Hz, 1H), 6.05 (s, 1H), 4.58 (d, J=5.6 Hz, 2H), 2.41 (s, 3H); MS (ES+) m/z 388.1 (M+1).

Example 2.30

Synthesis of 2-(5-Chloro-2-fluorobenzoylamino)-4-methylthiazole-5-carboxylic Acid Benzylamide

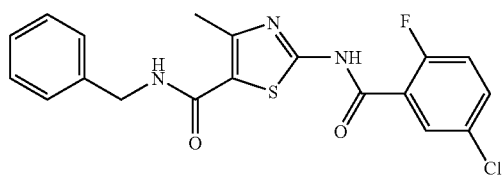 [SMILES: Cc1nc(NC(=O)c2cc(Cl)ccc2F)sc1C(=O)NCc1ccccc1]

Following the procedure as described in Example 2, making variations only as required to use 5-chloro-2-fluorobenzoyl chloride in place of benzoyl chloride to react with 2-amino-4-methylthiazole-5-carboxylic acid benzylamide, the title compound was obtained as a white solid in 22% yield. m.p. 175-178° C.; $^1$H NMR (CDCl$_3$, 300 MHz) δ 8.12 (dd, J=2.8, 6.6 Hz, 1H), 7.53 (ddd, J=2.8, 4.4, 8.8 Hz, 1H), 7.38-7.24 (m, 6H), 7.17 (dd, J=8.8, 11.3 Hz, 1H), 6.01 (t, J=4.7 Hz, 1H), 4.59 (d, J=5.6 Hz, 2H), 2.61 (s, 3H); MS (ES+) m/z 404.1 (M+1).

Example 2.31

Synthesis of 2-(3-Fluorobenzoylamino)-4-methylthiazole-5-carboxylic Acid Benzylamide

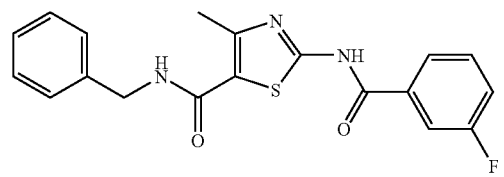 [SMILES: Cc1nc(NC(=O)c2cccc(F)c2)sc1C(=O)NCc1ccccc1]

Following the procedure as described in Example 2, making variations only as required to use 3-fluorobenzoyl chloride in place of benzoyl chloride to react with 2-amino-4-methylthiazole-5-carboxylic acid benzylamide, the title compound was obtained as a white solid in 18% yield; m.p. 162-165° C.; $^1$H NMR (CDCl$_3$, 300 MHz) δ 7.64-7.24 (m, 9H), 5.97 (t, J=5.4 Hz, 1H), 4.58 (d, J=5.4 Hz, 2H), 2.47 (s, 3H); MS (ES+) m/z 370.2 (M+1).

Example 2.32

Synthesis of 4-Methyl-2-(4-trifluoromethoxybenzoylamino)thiazole-5-carboxylic Acid Benzylamide

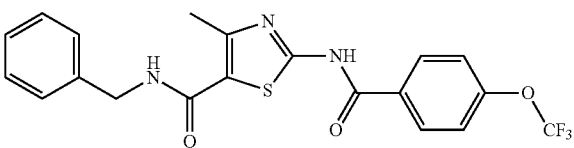 [SMILES: Cc1nc(NC(=O)c2ccc(OC(F)(F)F)cc2)sc1C(=O)NCc1ccccc1]

Following the procedure as described in Example 2, making variations only as required to use 4-trifluoromethoxybenzoyl chloride in place of benzoyl chloride to react with 2-amino-4-methylthiazole-5-carboxylic acid benzylamide, the title compound was obtained as a white solid in 20% yield; m.p. 168-170° C.; $^1$H NMR (CDCl$_3$, 300 MHz) δ 7.98 (d, J=8.8 Hz, 2H), 7.41-7.23 (m, 7H), 5.97 (t, J=5.6 Hz, 1H), 4.58 (d, J=5.6 Hz, 2H), 2.49 (s, 3H); MS (ES+) m/z 436.1 (M+1).

Example 2.33

Synthesis of 2-(4-Methoxybenzoylamino)-4-methylthiazole-5-carboxylic Acid Benzylamide

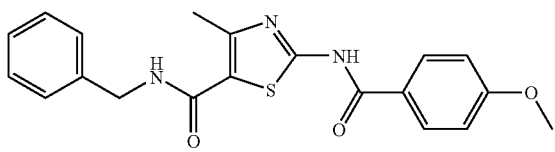 [SMILES: COc1ccc(C(=O)Nc2nc(C)c(C(=O)NCc3ccccc3)s2)cc1]

Following the procedure as described in Example 2, making variations only as required to use 4-methoxybenzoyl chloride in place of benzoyl chloride to react with 2-amino-4-methylthiazole-5-carboxylic acid benzylamide, the title compound was obtained as a white solid in 10% yield; m.p. 203-204° C.; $^1$H NMR (CDCl$_3$, 300 MHz) δ 7.86 (d, J=8.8 Hz, 2H), 7.35-7.30 (m, 5H), 6.96 (d, J=8.8 Hz, 2H), 5.97 (t, J=5.6 Hz, 1H), 4.58 (d, J=5.6 Hz, 2H), 3.86 (s, 3H), 2.49 (s, 3H); MS (ES+) m/z 382.1 (M+1).

Example 2.34

Synthesis of 2-(3-Methoxybenzoylamino)-4-methylthiazole-5-carboxylic Acid Benzylamide

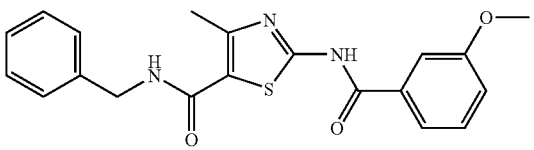

Following the procedure as described in Example 2, making variations only as required to use 3-methoxybenzoyl chloride in place of benzoyl chloride to react with 2-amino-4-methylthiazole-5-carboxylic acid benzylamide, the title compound was obtained as a white solid in 34% yield; m.p. 75-77° C.; $^1$H NMR (CDCl$_3$, 300 MHz) δ 7.43-7.31 (m, 8H), 7.12 (td, J=2.4, 6.7 Hz, 1H), 5.97 (t, J=5.6 Hz, 1H), 4.58 (d, J=5.6 Hz, 2H), 3.82 (s, 3H), 2.47 (s, 3H); MS (ES+) m/z 382.1 (M+1).

Example 2.35

Synthesis of 2-(3-Methanesulfonylbenzoylamino)-4-methylthiazole-5-carboxylic Acid Benzylamide

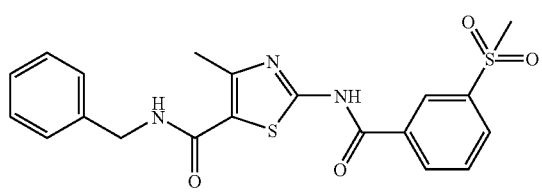 [SMILES: Cc1nc(NC(=O)c2cccc(S(C)(=O)=O)c2)sc1C(=O)NCc1ccccc1]

Following the procedure as described in Example 2, making variations only as required to use 3-methanesulfonylbenzoyl chloride in place of benzoyl chloride to react with 2-amino-4-methylthiazole-5-carboxylic acid benzylamide, the title compound was obtained as a white solid in 15% yield; m.p. 111-113° C.; $^1$H NMR (CD$_3$OD, 300 MHz) δ 8.55 (t, J=5.8 Hz, 1H), 8.09 (dd, J=1.2, 7.6 Hz, 1H), 7.36-7.19 (m, 2H), 7.68 (dd, J=1.2, 7.6 Hz, 1H), 7.27 (m, 5H), 4.50 (d, J=1.9 Hz, 2H), 3.33 (s, 3H), 2.52 (s, 3H); MS (ES+) m/z 430.1 (M+1).

Example 2.36

Synthesis of 2-(2-Methanesulfonylbenzoylamino)-4-methylthiazole-5-carboxylic Acid Benzylamide

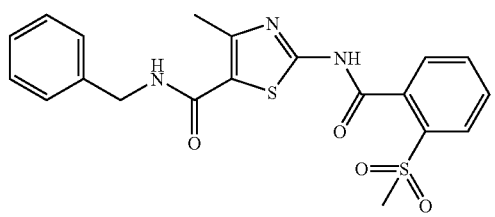 [SMILES: Cc1nc(NC(=O)c2ccccc2S(C)(=O)=O)sc1C(=O)NCc1ccccc1]

Following the procedure as described in Example 2, making variations only as required to use 2-methanesulfonylbenzoyl chloride in place of benzoyl chloride to react with 2-amino-4-methylthiazole-5-carboxylic acid benzylamide, the title compound was obtained as a white solid in 9% yield; m.p. 239-242° C.; $^1$H NMR (DMSO-d$_6$, 300 MHz) δ 8.64 (t, J=5.8 Hz, 1H), 8.59 (s, 1H), 8.35 (d, J=7.8 Hz, 1H), 8.13 (d, J=7.8 Hz, 1H), 7.80 (t, J=7.8 Hz, 1H), 7.33-7.19 (m, 6H), 4.38 (d, J=5.8 Hz, 2H), 3.26 (s, 3H), 2.51 (s, 3H); MS (ES+) m/z 430.1 (M+1).

Example 2.37

Synthesis of 2-(3,4-Dichlorobenzoylamino)-4-methylthiazole-5-carboxylic Acid Benzylamide

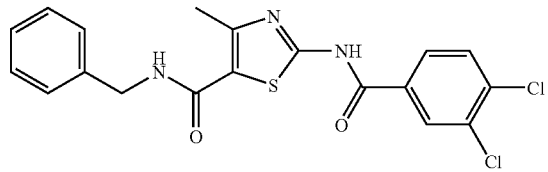 [SMILES: Cc1nc(NC(=O)c2ccc(Cl)c(Cl)c2)sc1C(=O)NCc1ccccc1]

Following the procedure as described in Example 2, making variations only as required to use 3,4-dichlorobenzoyl chloride in place of benzoyl chloride to react with 2-amino-4-methylthiazole-5-carboxylic acid benzylamide, the title compound was obtained as a white solid in 15% yield; m.p. 212-214° C.; $^1$H NMR (CD$_3$OD, 300 MHz) δ 8.21 (d, J=2.0 Hz, 1H), 7.93 (dd, J=2.0, 8.4 Hz, 1H), 7.68 (d, J=8.4 Hz, 1H), 7.33-7.23 (m, 5H), 4.50 (s, 2H), 2.54 (s, 3H); MS (ES+) m/z 420.0 (M+1).

Example 2.38

Synthesis of 2-(4-Methanesulfonylbenzoylamino)-4-methylthiazole-5-carboxylic Acid Benzylamide

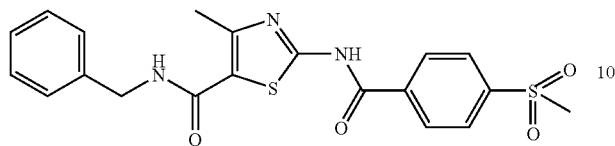

Following the procedure as described in Example 2, making variations only as required to use 4-methanesulfonylbenzoyl chloride in place of benzoyl chloride to react with 2-amino-4-methylthiazole-5-carboxylic acid benzylamide, the title compound was obtained as a white solid in 9% yield; m.p. 262-265° C.; $^1$H NMR (DMSO-d$_6$, 300 MHz) δ 8.65 (s, 1H), 8.27 (d, J=8.3 Hz, 2H), 8.06 (d, J=8.3 Hz, 2H), 7.31-7.21 (m, 5H), 4.38 (d, J=3.7 Hz, 2H), 3.27 (s, 3H), 2.51 (s, 3H); MS (ES+) m/z 430.1 (M+1).

Example 2.39

Synthesis of 4-Methyl-2-phenylacetylaminothiazole-5-carboxylic Acid Benzylamide

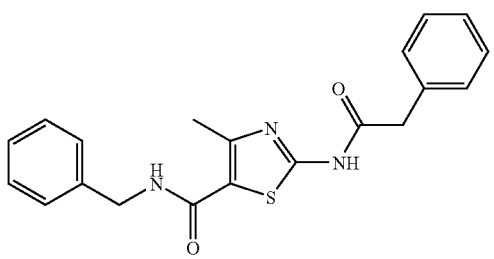 [SMILES: Cc1nc(NC(=O)Cc2ccccc2)sc1C(=O)NCc1ccccc1]

Following the procedure as described in Example 2, making variations only as required to use phenylacetyl chloride in place of benzoyl chloride to react with 2-amino-4-methylthiazole-5-carboxylic acid benzylamide, the title compound was obtained as a white solid in 17% yield; m.p. 63-65° C.; $^1$H NMR (CDCl$_3$, 300 MHz) δ 7.39-7.23 (m, 10H), 5.95 (s, 1H), 4.56 (d, J=5.4 Hz, 2H), 3.79 (s, 2H), 2.54 (s, 3H); MS (ES+) m/z 366.1 (M+1).

Example 2.40

Synthesis of 4-Methyl-2-(3-phenylpropionylamino)thiazole-5-carboxylic Acid Benzylamide

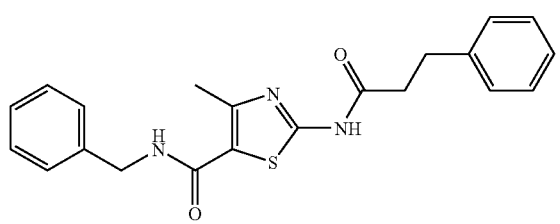 [SMILES: Cc1nc(NC(=O)CCc2ccccc2)sc1C(=O)NCc1ccccc1]

Following the procedure as described in Example 2, making variations only as required to use 3-phenylpropionyl chloride in place of benzoyl chloride to react with 2-amino-4-methylthiazole-5-carboxylic acid benzylamide, the title compound was obtained as a white solid in 25% yield; m.p. 63-65° C.; $^1$H NMR (CDCl$_3$, 300 MHz) δ 7.34-7.14 (m, 10H), 5.97 (t, J=4.9 Hz, 1H), 4.57 (d, J=5.6 Hz, 2H), 3.06-2.93 (m, 2H), 2.79-2.64 (m, 2H), 2.54 (s, 3H); MS (ES+) m/z 380.2 (M+1).

Example 2.41

Synthesis of 2-(2-Cyclopropylacetylamino)-4-methylthiazole-5-carboxylic Acid Benzylamide

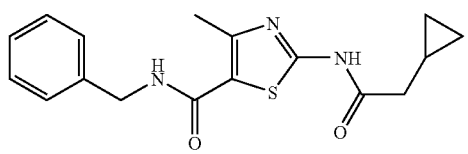 [SMILES: Cc1nc(NC(=O)CC2CC2)sc1C(=O)NCc1ccccc1]

Following the procedure as described in Example 2, making variations only as required to use cyclopropylacetyl chloride in place of benzoyl chloride to react with 2-amino-4-methylthiazole-5-carboxylic acid benzylamide, the title compound was obtained as a white solid in 27% yield; m.p. 136-139° C.; $^1$H NMR (CDCl$_3$, 300 MHz) δ 7.34-7.24 (m, 5H), 5.97 (s, 1H), 4.57 (d, J=5.6 Hz, 2H), 2.60 (s, 3H), 2.39 (d, J=7.2 Hz, 2H), 1.05-1.00 (m, 1H), 0.71-0.68 (m, 2H), 0.27 (q, J=4.8 Hz, 2H); MS (ES+) m/z 330.1 (M+1).

Example 2.42

Synthesis of 4-Methyl-2-(toluene-4-sulfonylamino)thiazole-5-carboxylic Acid Benzylamide

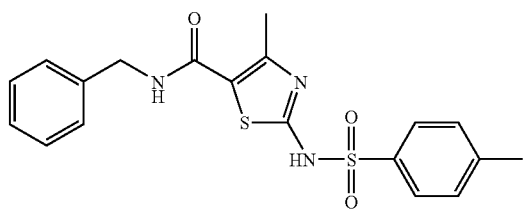 [SMILES: Cc1ccc(S(=O)(=O)Nc2nc(C)c(C(=O)NCc3ccccc3)s2)cc1]

Following the procedure as described in Example 2, making variations only as required to use 4-methylbenzenesulfonyl chloride in place of benzoyl chloride to react with 2-amino-4-methylthiazole-5-carboxylic acid benzylamide, the title compound was obtained as a white solid in 43% yield; m.p. 242-245° C.; $^1$H NMR (DMSO-d$_6$, 300 MHz) δ 12.89 (s, br, 1H), 8.58 (s, br, 1H), 7.66 (d, J=8.2 Hz, 2H), 7.33-7.17 (m, 7H), 4.32 (d, J=5.8 Hz, 2H), 2.32 (s, 3H), 2.31 (s, 3H); $^{13}$C NMR (DMSO-d$_6$, 75 MHz) δ 166.2, 160.6, 143.0, 139.7, 139.6, 139.5, 129.9, 128.7, 127.8, 127.3, 126.2, 111.7, 43.1, 21.4, 13.6; MS (ES+) m/z 402.4 (M+1).

Example 3

Synthesis of 2-Benzoylamino-4-methylthiazole-5-carboxylic Acid (1-Phenylpropyl)amide

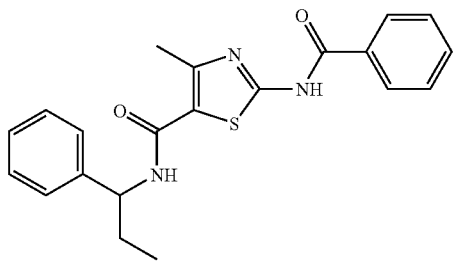 [SMILES: CCC(NC(=O)c1sc(NC(=O)c2ccccc2)nc1C)c1ccccc1]

To a solution of 2-benzoylamino-4-methylthiazole-5-carboxylic acid (0.13 g, 0.50 mmol) and 4-methylmorpholine (0.08 mL, 0.70 mmol) in tetrahydrofuran (20 mL) at 0° C. was added iso-butylchloroformate (0.08 mL, 0.60 mmol). The reaction mixture was stirred for 15 minutes, then warmed to ambient temperature and stirred for another hour before α-ethylbenzylamine (0.1 mL, 0.70 mmol) was added. The reaction mixture was kept stirring at ambient temperature overnight and then concentrated. Purification of the residue by column chromatography afforded the title compound in 19% yield (0.037 g); m. p. 87-89° C.; $^1$H NMR (CDCl$_3$, 300 MHz) δ 7.89-7.86 (m, 2H), 7.61-7.22 (m, 8H), 5.91 (d, J=7.5 Hz, 1H), 5.02-4.94 (m, 1H), 2.33 (s, 3H), 2.27-1.78 (m, 2H), 0.92 (t, J=7.5 Hz, 3H); $^{13}$C NMR (CDCl$_3$, 75 MHz) δ 165.1, 161.4, 157.0, 152.1, 141.8, 133.3, 131.4, 129.1, 128.7, 127.6, 127.5, 126.6, 118.8, 55.6, 29.3, 16.7, 10.8. MS (ES+) m/z 380.5 (M+1).

Example 3.1

Synthesis of 2-Benzoylamino-4-chlorothiazole-5-carboxylic Acid Benzylamide

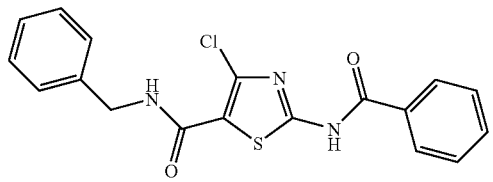 [SMILES: O=C(Nc1nc(Cl)c(C(=O)NCc2ccccc2)s1)c1ccccc1]

Following the procedure as described in Example 3, making variations only as required to use benzylamine in place of α-ethylbenzylamine to react with 2-benzoylamino-4-chlorothiazole-5-carboxylic acid, the title compound was obtained as a white solid in 20% yield; m. p. 247-249° C.; $^1$H NMR (DMSO-d$_6$, 300 MHz) δ 12.5 (s, 1H), 8.11-7.93 (m, 2H), 7.72 (t, J=5.7 Hz, 1H), 7.58-6.95 (m, 8H), 4.48 (d, J=5.7 Hz, 2H); $^{13}$C NMR (DMSO-d$_6$, 75 MHz) δ 166.1, 160.0, 138.5, 134.2, 133.0, 131.4, 128.6, 128.5, 128.4, 127.5, 127.2, 119.6, 43.4; MS (ES+) m/z 372.3 (M+1).

Example 4

Synthesis of 4-Methyl-2-(3-phenylureido)thiazole-5-carboxylic Acid Benzylamide

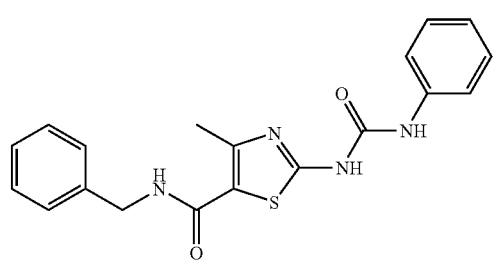 [SMILES: Cc1nc(NC(=O)Nc2ccccc2)sc1C(=O)NCc1ccccc1]

To a stirred solution of 2-amino-4-methylthiazole-5-carboxylic acid benzylamide (0.10 g, 0.40 mmol) in anhydrous tetrahydrofuran (5 mL), triethylamine (0.17 mL, 0.12 g, 1.22 mmol) and phenyl isocyanate (0.07 mL, 0.072 g, 0.61 mmol) were added dropwise at ambient temperature. The reaction mixture was stirred at ambient temperature for 25 h and then diluted with ethyl ether (20 mL). The white precipitate obtained was collected by filtration, washed with ethyl ether (3×6 mL) and dried under the reduced pressure to afford the title compound as a white solid in 80% yield (0.119 g); m.p.>300° C.; $^1$H NMR (DMSO-d$_6$, 300 MHz) δ 9.00 (s, 1H), 8.47 (t, J=5.7 Hz, 1H), 7.46-7.17 (m, 10H), 7.03-6.98 (m, 1H), 4.35 (d, J=6.0 Hz, 2H), 2.43 (s, 3H); $^{13}$C NMR (DMSO-d$_6$, 75 MHz) δ 162.2, 140.2, 140.0, 129.4, 129.2, 128.7, 127.7, 127.1, 123.3, 119.1, 118.6, 43.0, 39.1; MS (ES+) m/z 367.2 (M+1).

Example 4.1

Synthesis of 2-[3-(4-Fluorophenyl)ureido]-4-methylthiazole-5-carboxylic Acid Benzylamide

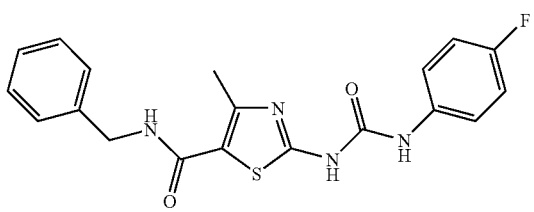 [SMILES: Cc1nc(NC(=O)Nc2ccc(F)cc2)sc1C(=O)NCc1ccccc1]

Following the procedure as described in Example 4, making variations only as required to use 4-fluorophenyl isocyanate in place of phenyl isocyanate to react with 2-amino-4-methylthiazole-5-carboxylic acid benzylamide, the title compound was obtained as a white solid in 83% yield; m.p.>300° C.; $^1$H NMR (DMSO-d$_6$, 300 MHz) δ 9.03 (s, 1H), 8.47 (t, J=6.0 Hz, 1H), 7.49-7.05 (m, 10H), 4.35 (d, J=5.7 Hz, 2H), 2.43 (s, 3H); $^{13}$C NMR (DMSO-d$_6$, 75 MHz) δ 162.2, 140.2, 128.7, 127.7, 127.2, 121.1, 121.0, 120.5, 116.1, 115.9, 115.8, 43.0, 39.1; MS (ES+) m/z 385.1 (M+1).

Example 4.2

Synthesis of 2-[3-(4-Chlorophenyl)ureido]-4-methylthiazole-5-carboxylic Acid Benzylamide

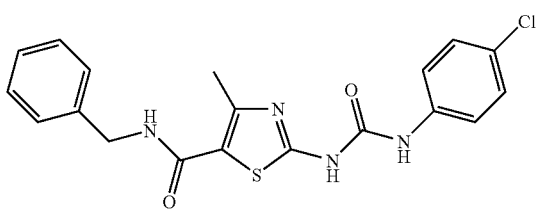 [SMILES: Cc1nc(NC(=O)Nc2ccc(Cl)cc2)sc1C(=O)NCc1ccccc1]

Following the procedure as described in Example 4, making variations only as required to use 4-chlorophenyl isocyanate in place of phenyl isocyanate to react with 2-amino-4-methylthiazole-5-carboxylic acid benzylamide, the title compound was obtained as a white solid in 62% yield; m.p.>300° C.; $^1$H NMR (DMSO-d$_6$, 300 MHz) δ 9.14 (s 1H), 8.47 (t, J=6.0 Hz, 1H), 7.51-7.48 (m, 2H), 7.35-7.17 (m, 8H), 4.35 (d, J=5.7 Hz, 2H), 2.43 (s, 3H); $^{13}$C NMR (DMSO-d$_6$, 75 MHz) δ 162.2, 140.1, 138.1, 129.2, 128.7, 127.7, 127.1, 126.8, 120.7, 43.0, 39.1; MS (ES+) m/z 401.0 (M+1).

Example 5

Synthesis of 2-Benzoylaminothiazole-5-carboxylic Acid Benzylamide

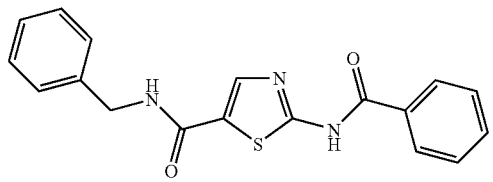 [SMILES: O=C(Nc1ncc(C(=O)NCc2ccccc2)s1)c1ccccc1]

A. Benzoyl chloride (0.44 g, 0.37 mL) was added to a mixture of 2-aminothiazole-5-carboxylic acid methyl ester (0.50 g, 3.16 mmol), 4-dimethylaminopyridine (0.050 g, 0.41 mmol) and pyridine (2.5 mL, 31.60 mmol) in N,N-dimethylformamide (20 mL) at ambient temperature. The reaction mixture was stirred at ambient temperature for 12 h, and concentrated in vacuo. The residue was purified by column chromatography to yield 2-benzoylaminothiazole-5-carboxylic acid methyl ester in 78% yield (0.654 g); MS (ES+) m/z 263.2 (M+1).

B. A mixture of 2-benzoylaminothiazole-5-carboxylic acid methyl ester (0.40 g, 1.52 mmol), sodium cyanide (0.19 g, 3.79 mmol) and benzylamine (4 mL) was stirred at 80° C. for 70 h. The mixture was filtered, washed with ethyl ether, and the filtrate was concentrated in vacuo. The residue was dissolved in a mixture of methanol and tetrahydrofuran and aqueous lithium hydroxide solution (0.24 g in 6 mL water) was added. The mixture was stirred at 50° C. for 4 d. The organic solvents were removed in vacuo. The solid obtained was collected by filtration, washed with water, methanol and dried. The title compound was obtained as a white solid in 5% yield (0.005 g); $^1$H NMR (DMSO-d$_6$, 300 MHz) δ 8.93 (s, 1H), 8.20-8.03 (m, 3H), 7.62-7.41 (m, 3H), 7.39-7.14 (m, 6H), 4.43 (d, J=3.9 Hz, 2H); MS (ES+) m/z 338.5 (M+1).

Example 6

Synthesis of 4-Methyl-2-[4-(2H-tetrazol-5-yl)benzoylamino]thiazole-5-carboxylic Acid Benzylamide

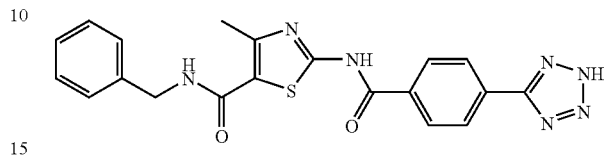

A mixture of 2-(4-cyanobenzoylamino)-4-methylthiazole-5-carboxylic acid benzylamide (0.080 g, 0.21 mmol), sodium azide (0.028 g, 0.43 mmol) and ammonium chloride (0.006 g, 0.11 mmol) in N,N-dimethylformamide (5 mL) was stirred at 80° C. for 18 hours. The reaction mixture was cooled to ambient temperature, and 1 N hydrochloric acid (0.5 mL) solution was added. Ethyl acetate (10 mL) and brine (10 mL) were added to the reaction mixture. The organic layer was separated and dried over anhydrous sodium sulfate, and filtered. The filtrate was concentrate in vacuo and the residue was purified by column chromatography to afford the title compound as a white solid in 23% yield (0.020 g); m.p.>300° C.; $^1$H NMR (CD$_3$OD, 300 MHz) δ 8.20-8.09 (m, 4H), 8.45-7.20 (m, 5H), 4.51 (s, 2H), 2.55 (s, 3H); $^{13}$C NMR (CD$_3$OD, 75 MHz) δ 163.6, 138.8, 128.4, 128.1, 127.1, 126.8, 126.5, 43.1, 15.8; MS (ES+) m/z 420.5 (M+1).

Example 7

Synthesis of 2-Benzoylamino-4-methylthiazole-5-carboxylic Acid Cyclopropylmethylamide

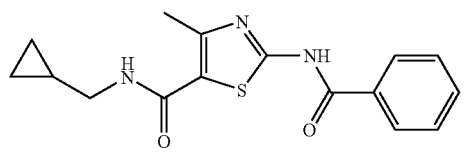 [SMILES: Cc1nc(NC(=O)c2ccccc2)sc1C(=O)NCC1CC1]

A. To a solution of 2-benzoylamino-4-methylthiazole-5-carboxylic acid (0.10 g, 0.38 mmol) in anhydrous dichloromethane (2 mL) was added two drops of N,N-dimethylformamide, following by the addition of oxalyl chloride (0.058 mg, 0.46 mmol) dropwise. After the reaction mixture was stirred at ambient temperature for 2 h, the solvent was removed in vacuo to dryness to obtain 2-benzoylamino-4-methylhiazole-5-carbonyl chloride (0.079 g) as a yellow solid.

B. To a cooled mixture of cyclopropylmethylamine (0.033 g, 0.46 mmol), pyridine (0.090 g, 1.14 mmol) and 4-dimethylaminoyridine (0.010 mg) in anhydrous tetrahydrofuran was added 2-benzoylamino-4-methylthiazole-5-carbonyl chloride (0.079 g, 0.038 mmol) in anhydrous dichloromethane (1 mL) dropwise. The reaction mixture was stirred at ambient temperature for 2 h, then diluted with dichloromethane (10 mL), washed with 1 N hydrochloric acid (5 mL), saturated aqueous sodium bisulfate (2×5 mL), and brine (5 mL), dried over anhydrous sodium sulfate, and filtered. The filtrate was concentrate in vacuo and the residue was purified by column chromatography to afford the title compound as a white solid in 45% yield (45 mg); m.p. 163-166° C.; $^1$H NMR (CDCl$_3$, 300 MHz) δ 7.89 (d, J=7.9 Hz, 2H), 7.57 (t, J=7.4 Hz, 1H), 7.45 (t, J=7.5 Hz, 2H), 5.84 (s, 1H), 3.23 (dd, J=5.4, 7.1 Hz, 2H), 2.23 (s, 3H), 1.00-0.98 (m, 1H), 0.53 (q, J=5.8 Hz, 2H), 0.22 (q, J=5.0 Hz, 2H); MS (ES+) m/z 316.1 (M+1).

Example 7.1

Synthesis of
2-Benzoylamino-4-methylthiazole-5-carboxylic Acid
3-Chlorobenzylamide

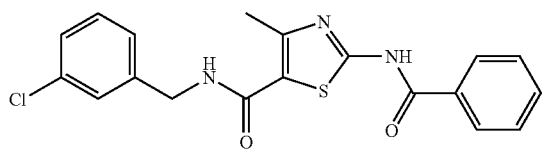 [SMILES: Cc1nc(NC(=O)c2ccccc2)sc1C(=O)NCc1cccc(Cl)c1]

Following the procedure as described in Example 7, making variations only as required to use 3-chlorobenzylamine in place of cyclopropylmethylamine to react with 2-benzoylamino-4-methylhiazole-5-carbonyl chloride, the title compound was obtained as a white solid in 43% yield; m.p. 198-199° C.; $^1$H NMR (CDCl$_3$, 300 MHz) δ 7.89 (d, J=8.4 Hz, 2H), 7.65-7.49 (m, 3H), 7.31-7.20 (m, 4H), 6.00 (t, J=5.7 Hz, 1H), 4.56 (d, J=5.7 Hz, 2H), 2.53 (s, 3H); MS (ES+) m/z 386.1 (M+1).

Example 7.2

Synthesis of
2-Benzoylamino-4-methylthiazole-5-carboxylic Acid
3-Fluorobenzylamide

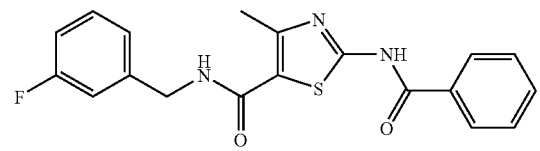 [SMILES: Cc1nc(NC(=O)c2ccccc2)sc1C(=O)NCc1cccc(F)c1]

Following the procedure as described in Example 7, making variations only as required to use 3-fluorobenzylamine in place of cyclopropylmethylamine to react with 2-benzoylamino-4-methylhiazole-5-carbonyl chloride, the title compound was obtained as a white solid in 46% yield; m.p. 216-217° C.; $^1$H NMR (CDCl$_3$, 300 MHz) δ 7.90 (d, J=7.2 Hz, 2H), 7.64-7.51 (m, 3H), 7.32-7.24 (m, 1H), 7.12-6.98 (m, 3H), 6.01 (t, J=5.7 Hz, 1H), 4.58 (d, J=5.7 Hz, 2H), 2.53 (s, 3H); MS (ES+) m/z 370.1 (M+1).

Example 7.3

Synthesis of
2-Benzoylamino-4-methylthiazole-5-carboxylic Acid
2-Fluorobenzylamide

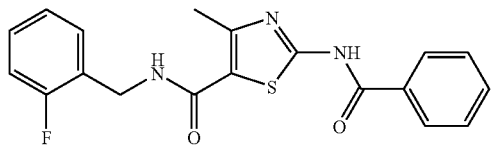 [SMILES: Cc1nc(NC(=O)c2ccccc2)sc1C(=O)NCc1ccccc1F]

Following the procedure as described in Example 7, making variations only as required to use 2-fluorobenzylamine in place of cyclopropylmethylamine to react with 2-benzoylamino-4-methylhiazole-5-carbonyl chloride, the title compound was obtained as a white solid in 46% yield; m.p. 180-183° C.; $^1$H NMR (CDCl$_3$, 300 MHz) δ 7.89 (d, J=7.3 Hz, 2H), 7.60 (t, J=6.8 Hz, 1H), 7.50 (t, J=7.3 Hz, 2H), 7.39 (t, J=6.8 Hz, 1H), 7.26-7.11 (m, 3H), 6.06 (s, 1H), 4.63 (d; J=5.7 Hz, 2H), 2.49 (s, 3H); MS (ES+) m/z 370.4 (M+1).

Example 7.4

Synthesis of
2-Benzoylamino-4-methylthiazole-5-carboxylic acid
2-chlorobenzylamide

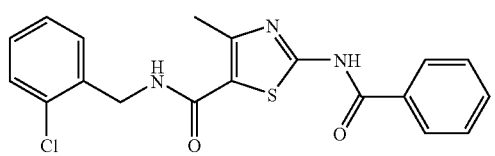 [SMILES: Cc1nc(NC(=O)c2ccccc2)sc1C(=O)NCc1ccccc1Cl]

Following the procedure as described in Example 7, making variations only as required to use 2-chlorobenzylamine in place of cyclopropylmethylamine to react with 2-benzoylamino-4-methylhiazole-5-carbonyl chloride, the title compound was obtained as a white solid in 51% yield; m.p. 191-193° C.; $^1$H NMR (CDCl$_3$, 300 MHz) δ 7.88 (d, J=7.1 Hz, 2H), 7.86-7.28 (m, 5H), 7.29-7.22 (m, 2H), 6.19 (t, J=5.7 Hz, 1H), 4.66 (d, J=5.7 Hz, 2H), 2.39 (s, 3H); MS (ES+) m/z 386.1 (M+1).

Example 7.5

Synthesis of
2-Benzoylamino-4-methylthiazole-5-carboxylic Acid
2-Trifluoromethylbenzylamide

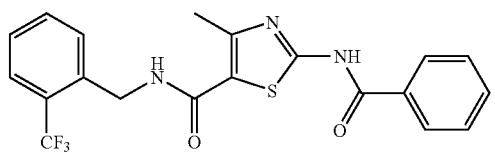 [SMILES: Cc1nc(NC(=O)c2ccccc2)sc1C(=O)NCc1ccccc1C(F)(F)F]

Following the procedure as described in Example 7, making variations only as required to use 2-trifluoromethylbenzylamine in place of cyclopropylmethylamine to react with 2-benzoylamino-4-methylhiazole-5-carbonyl chloride, the title compound was obtained as a white solid in 47% yield; m.p. 198-199° C.; $^1$H NMR (CDCl$_3$, 300 MHz) δ 7.88 (d, J=7.1 Hz, 2H), 7.67-7.37 (m, 7H), 6.07 (t, J=5.8 Hz, 1H), 4.76 (d, J=5.8 Hz, 2H), 2.35 (s, 3H); MS (ES+) m/z 420.1 (M+1).

Example 7.6

Synthesis of
2-Benzoylamino-4-methylthiazole-5-carboxylic Acid
4-Fluorobenzylamide

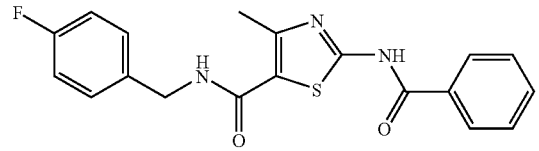 [SMILES: Cc1nc(NC(=O)c2ccccc2)sc1C(=O)NCc1ccc(F)cc1]

Following the procedure as described in Example 7, making variations only as required to use 4-fluorobenzylamine in place of cyclopropylmethylamine to react with 2-benzoylamino-4-methylthiazole-5-carbonyl chloride, the title compound was obtained as a white solid in 47% yield; m.p. 206-208° C.; $^1$H NMR (CDCl$_3$, 300 MHz) δ 7.89 (d, J=7.4 Hz, 2H), 7.60 (t, J=7.2 Hz, 1H), 7.49 (t, J=7.6 Hz, 2H), 7.30 (dd, J=5.4, 8.4 Hz, 2H), 7.02 (t, J=8.6 Hz, 2H), 5.99 (s, 1H), 4.54 (d, J=5.7 Hz, 2H), 2.43 (s, 3H); MS (ES+) m/z 370.4 (M+1).

Example 8

Synthesis of 2-Benzylamino-4-methylthiazole-5-carboxylic Acid Benzylamide

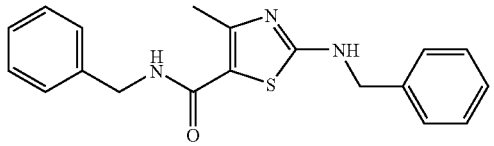 [SMILES: Cc1nc(NCc2ccccc2)sc1C(=O)NCc1ccccc1]

A mixture of 2-amino-4-methylthiazole-5-carboxylic acid benzylamide (0.20 g, 0.81 mmol), benzaldehyde (0.086 g, 0.81 mmol) and titanium(IV) isopropoxide (0.29 g, 1.01 mmol) in anhydrous tetrahydrofuran (2 mL) was stirred at ambient temperature for 18 h. Sodium cyanoborohydride (0.036 g, 0.57 mmol) was added to the mixture and stirring was continued at ambient temperature for another 6 h. The reaction was quenched with the addition of water (2 mL). The precipitate obtained was filtered and washed with ethanol. The filtrate was concentrated in vacuo. The residue was purified by column chromatography to obtain the title compound as a white solid in 58% yield (0.16 g); m.p. 169-172° C.; $^1$H NMR (CDCl$_3$, 300 MHz) δ 7.37-7.23 (m, 10H), 6.02 (s, 1H), 5.69 (s, 1H), 4.54 (d, J=5.6 Hz, 2H), 4.43 (s, 2H), 2.49 (s, 3H); MS (ES+) m/z 338.3 (M+1).

Example 9

Synthesis of N-(5-(2-Benzoylhydrazinecarbonyl)-4-methylthiazol-2-yl)benzamide

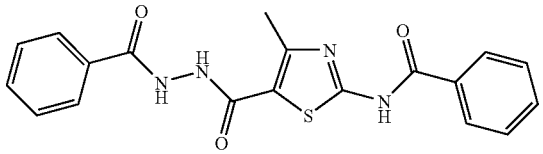 [SMILES: Cc1nc(NC(=O)c2ccccc2)sc1C(=O)NNC(=O)c1ccccc1]

To a solution of 2-benzamido-4-methylthiazole-5-carboxylic acid (0.30 g, 1.14 mmol) in tertahydrofuran (28 mL) was added N-methylmorpholine (0.23 mL, 0.21 g, 2.09 mmol) under nitrogen atmosphere, followed by the addition of isobutyl chloroformate (0.2 mL, 0.21 g, 1.54 mmol) dropwise at ambient temperature. The mixture was stirred at ambient temperature for 7 hours. Benzhydrazide (0.23 g, 1.71 mmol) and 4-methylmorpholine (0.15 mL, 0.14 g, 1.36 mmol) were added to the reaction mixture. After being stirred at ambient temperature for 18 hours, the reaction mixture was diluted with ethyl acetate (50 mL), washed with water (3×10 mL). The organic phase was separated and dried over anhydrous sodium sulfate. After filtration, the filtrate was concentrated in vacuo. The crude product was purified by column chromatography eluted with ethyl acetate/hexanes (20/80 to 30/70) to afford the title compound as a white solid (0.059 g, 14% yield); m.p. 258-260° C.; $^1$H NMR (DMSO-d$_6$, 300 MHz) δ 12.90 (br, 1H), 10.46 (s, 1H), 10.10 (s, 1H), 8.09 (d, J=7.4 Hz, 2H), 7.93 (d, J=6.9 Hz, 2H), 7.65-7.47 (m, 6H), 2.56 (s, 3H); MS (ES+) m/z 381.4 (M+1).

Example 10

Synthesis of N-(5-(1H-Imidazole-1-carbonyl)-4-methylthiazol-2-yl)benzamide

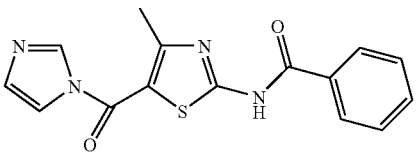 [SMILES: Cc1nc(NC(=O)c2ccccc2)sc1C(=O)n1ccnc1]

To a solution of 2-benzamido-4-methylthiazole-5-carboxylic acid (1.50 g, 5.72 mmol) in dry N,N-dimethylformamide (16 mL) was added N,N'-carbonyldiimidazole (1.22 g, 7.50 mmol) at ambient temperature. The mixture was stirred at ambient temperature for 3 hours. The reaction mixture was diluted with diethyl ether (50 mL) and filtered. The solid was washed with diethyl ether (50 mL) and dried in vacuo to give the title compound as a white solid (1.24 g, 70% yield); m.p. 228-231° C.; $^1$H NMR (DMSO-d$_6$, 300 MHz) δ 13.29 (s, 1H), 8.34 (s, 1H), 8.10-8.08 (m, 2H), 7.74-7.51 (m, 4H), 7.13 (s, 1H), 2.49 (s, 3H); $^{13}$C NMR (DMSO-d$_6$, 75 MHz) δ 166.5, 162.3, 160.1, 159.1, 138.4, 133.7, 131.7, 130.8, 129.2, 128.8, 118.9, 115.9, 18.2; MS (ES+) m/z 313.5 (M+1).

Example 11

Synthesis of N-Benzyl-4-methyl-2-(5-phenylpentanamido)thiazole-5-carboxamide

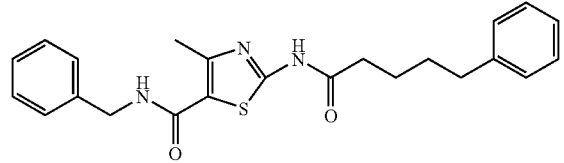 [SMILES: Cc1nc(NC(=O)CCCCc2ccccc2)sc1C(=O)NCc1ccccc1]

A. To a solution of 5-phenylpentanoic acid (0.14 g, 0.81 mmol) in anhydrous dichloromethane (5 mL) was added two drops of N,N-dimethylformamide, followed by the addition of oxalyl chloride (0.11 g, 0.89 mmol). The reaction was stirred at ambient temperature for 2 hours. The solvent was removed in vacuo to dryness to afford 5-phenylpentanoyl chloride (0.16 g, 0.81 mmol) as a yellow oil.

B. To a cooled mixture of 2-amino-4-methylthiazole-5-carboxylic acid benzylamide (0.10 g, 0.40 mmol), pyridine (0.096 g, 1.21 mmol), and dimethylaminopyridine (0.010 mg) in anhydrous tetrahydrofuran (5 mL) was added 5-phenylpentanoyl chloride (0.16 g, 0.81 mmol) in anhydrous dichloromethane (1 mL) dropwise. The reaction mixture was stirred at ambient temperature for 2 hours, then diluted with dichloromethane (10 mL) and washed with saturated sodium bicarbonate solution (2×5 mL), 1 N hydrochloric acid (5 mL), and brine (5 mL). The organic phase was dried over anhydrous sodium sulfate, filtered, and the filtrate was concentrate in vacuo. The residue was purified by column chromatography over silica gel, eluting with ethyl acetate/hexanes (1/1) to afford the title compound as a clear oil (0.16 g, 97%) %); $^1$H NMR (CDCl$_3$, 300 MHz) δ 11.19 (s, br, 1H), 7.33-7.09 (m, 10H), 6.40 (t, J=4.8 Hz, 1H), 4.58 (d, J=5.8 Hz, 2H), 2.60-2.39 (m, 7H), 1.74-1.56 (m, 4H); MS (ES+) m/z 408.6 (M+1).

Example 11.1

Synthesis of N-Benzyl-4-methyl-2-(4-phenylbutanamido)thiazole-5-carboxamide

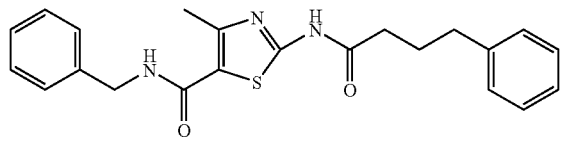 [SMILES: Cc1nc(NC(=O)CCCc2ccccc2)sc1C(=O)NCc1ccccc1]

Following the procedure as described in Example 11, making variations only as required to use 4-phenylbutanoic acid in place of 5-phenylpentanoic acid to react with 2-amino-4-methylthiazole-5-carboxylic acid benzylamide, the title compound was obtained as a white solid in 47% yield; m.p. 45-46° C.; $^1$H NMR (CDCl$_3$, 300 MHz) δ 11.13 (s, br, 1H), 7.35-7.09 (m, 10H), 6.24 (t, J=5.0 Hz, 1H), 4.59 (d, J=5.6 Hz, 2H), 2.63 (t, J=7.5 Hz, 2H), 2.52 (s, 3H), 2.41 (t, J=7.5 Hz, 2H), 2.00 (q, J=7.5 Hz, 2H); MS (ES+) m/z 397.5 (M+1).

Example 11.2

Synthesis of N-Benzyl-4-methyl-2-{[4-(2-oxopyridin-1(2H)-yl)benzoyl]amino}-1,3-thiazole-5-carboxamide

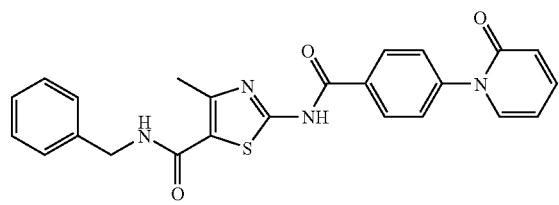 [SMILES: Cc1nc(NC(=O)c2ccc(-n3ccccc3=O)cc2)sc1C(=O)NCc1ccccc1]

Following the procedure as described in Example 11, making variations only as required to use 4-(2-oxopyridin-1-yl)-benzoic acid in place of 5-phenylpentanoic acid to react with 2-amino-4-methylthiazole-5-carboxylic acid benzylamide, the title compound was obtained as a white solid in 58% yield; $^1$H NMR (CDCl$_3$, 300 MHz) δ 12.96 (s, 1H), 8.63 (t, J=5.9 Hz, 1H), 8.18 (d, J=8.6 Hz, 2H), 7.66 (dd, J=1.7, 6.9 Hz, 1H), 7.57 (d, J=8.6 Hz, 2H), 7.50 (ddd, J=2.0, 6.8, 9.0 Hz, 1H), 7.35-7.20 (m, 5H), 6.48 (d, J=9.0 Hz, 1H), 6.32 (dt, J=1.1, 6.8 Hz, 1H), 4.38 (d, J=5.9 Hz, 2H), 2.52 (s, 3H); MS (ES+) m/z 445.4 (M+1).

Example 12

Synthesis of 2-[(5-benzylcarbamoyl-4-methyl-thiazol-2-ylcarbamoyl)-methyl]-benzoic acid

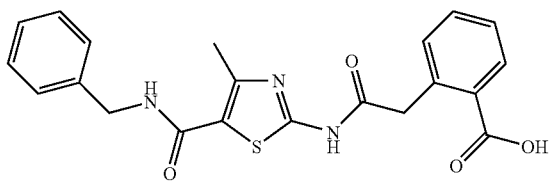 [SMILES: Cc1nc(NC(=O)Cc2ccccc2C(=O)O)sc1C(=O)NCc1ccccc1]

2-Amino-4-methylthiazole-5-carboxylic acid benzylamide (0.25 g, 1.00 mmol) and homophthalic acid (0.18 g, 1.00 mmol) were melted together at 170° C. for 2 hours. A colorless solid formed after the melt was cooled to ambient temperature. The solid was washed with ether (50 mL) and then crystallized from ethyl acetate/methanol to afford the title compound in 60% yield; $^1$H NMR (DMSO-d$_6$, 300 MHz) δ 12.37 (s, 1H), 8.48 (t, J=5.9 Hz, 1H), 7.88 (dd, J=1.4, 7.6 Hz, 1H), 7.50 (dt, J=1.4, 7.6 Hz, 1H), 7.40-7.15 (m, 7H), 4.34 (d, J=5.9 Hz, 2H), 4.14 (s, 2H), 2.45 (s, 3H); MS (ES+) m/z 410.5 (M+1).

Example 13

Synthesis of N-Benzyl-2-(2-methoxyisonicotinamido)-4-methylthiazole-5-carboxamide

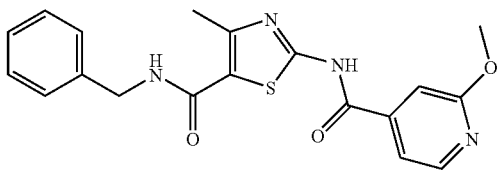 [SMILES: COc1cc(C(=O)Nc2nc(C)c(C(=O)NCc3ccccc3)s2)ccn1]

To a solution of 2-methoxyisonicotinic acid (0.25 g, 1.01 mmol) in anhydrous tetrahydrofuran (10 mL) was added 4-methyl morpholine (0.15 g, 1.45 mmol), followed by the dropwise addition of isobutylchloroformate (0.19 g, 1.36 mmol) at 0° C. The reaction mixture was stirred at ambient temperature for 6 hours. Then a solution of 2-amino-N-benzyl-4-methylthiazole-5-carboxamide in tetrahydrofuran (10 mL) was added to it. The reaction mixture was stirred at ambient temperature for another 6 hours. The solvent was removed in vacuo. The residue was dissolved in ethyl acetate (50 mL) and washed with diluted hydrochloric acid solution (10 mL), saturated sodium bicarbonate solution (10 mL) and brine (10 mL). The organic layer was dried over anhydrous sodium sulfate, filtered and the filtrate was concentrated in vacuo. The residue was recrystallized from ethyl acetate and hexane to yield the title compound as a colorless solid in 83% yield (0.32 g); m.p. 188-190° C.; $^1$H NMR (CDCl$_3$, 300 MHz) δ 8.32 (d, J=5.3 Hz, 1H), 7.37-7.25 (m, 7H), 7.17 (s, 1H), 5.99 (t, J=5.0 Hz, 1H), 4.59 (d, J=5.6 Hz, 2H), 3.96 (s, 3H), 2.55 (s, 3H); $^1$H NMR (CDCl$_3$, 75 MHz) δ 164.9, 163.7, 161.9, 157.1, 151.3, 148.4, 141.5, 137.6, 128.8, 127.8, 127.8, 119.4, 113.8, 109.4, 54.0, 44.2, 16.7; MS (ES+) m/z 383.5 (M+1).

Example 14

Synthesis of N-Benzyl-4-methyl-2-(2-oxo-1,2-dihydropyridine-4-carboxamido)thiazole-5-carboxamide

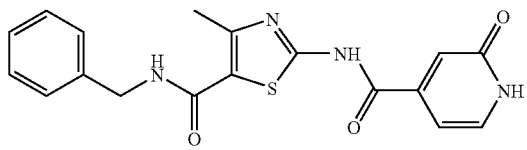 [SMILES: Cc1nc(NC(=O)c2cc[nH]c(=O)c2)sc1C(=O)NCc1ccccc1]

To a solution of N-benzyl-2-(2-methoxyisonicotinamido)-4-methylthiazole-5-carboxamide (0.26 g, 0.68 mmol) in anhydrous chloroform (15 mL) was added iodotrimethylsilane (1.37 g, 6.80 mmol) at 0° C. The mixture was refluxed for 16 hours and cooled down to ambient temperature. Methanol (3 mL) was added dropwise to quench the reaction. The solvent was removed in vacuo. The residue was dissolved in ethyl acetate (100 mL) and washed with saturated sodium bicarbonate solution (2×100 mL), and brine (150 mL). The organic layer was dried over anhydrous sodium sulfate, filtered, and the filtrate was concentrate in vacuo. The residue was recrystallized from ethyl acetate and methanol to yield a colorless solid in 55% yield (0.13 g); m.p. 290-292° C.; $^1$H NMR (DMSO-d$_6$, 300 MHz) δ 12.74 (s, br, 2H), 8.63 (t, J=5.9 Hz, 1H), 7.48 (d, J=6.8 Hz, 1H), 7.35-7.17 (m, 5H), 6.95 (d, J=1.6 Hz, 1H), 6.66 (dd, J=1.6, 6.8 Hz, 1H), 4.37 (d, J=5.9 Hz, 2H), 2.49 (s, 3H); $^{13}$C NMR (DMSO-d$_6$, 75 MHz) δ 165.5, 162.6, 163.1, 162.0, 144.1, 140.0, 136.8, 128.7, 127.6, 127.1, 120.3, 119.2, 103.3, 43.0, 17.0; MS (ES+) m/z 369.2 (M+1).

Example 15

Synthesis of N-Benzyl-4-methyl-2-(2-oxo-1-phenyl-1,2-dihydropyridine-4-carboxamido)thiazole-5-carboxamide

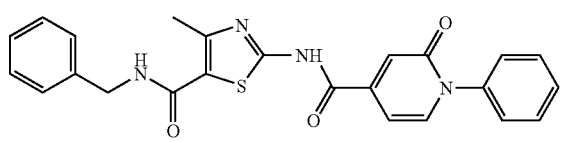 [SMILES: Cc1nc(NC(=O)c2ccn(-c3ccccc3)c(=O)c2)sc1C(=O)NCc1ccccc1]

To a degassed solution of N-benzyl-4-methyl-2-(2-oxo-1,2-dihydropyridine-4-carboxamido)thiazole-5-carboxamide (0.060 g, 0.16 mmol), potassium carbonate (0.033 g, 0.24 mmol) and 8-hydroxyquinoline (0.0034 g, 0.024 mmol) in dimethyl sulfoxide (5 mL) were added iodobenzene (0.039 g, 0.19 mmol) and finally copper(I) iodide (0.0046 g, 0.025 mmol). The reaction mixture was heated at 130° C. for 16 hours, then cooled to ambient temperature and filtered. The solvent was removed in vacuo. The residue was dissolved in dichloromethane (40 mL) and washed with saturated aqueous sodium bicarbonate solution (2×20 mL), and brine (20 mL). The organic layer was dried over anhydrous sodium sulfate, filtered, and the filtrate was concentrate in vacuo. The residue was recrystallized from ethyl acetate and methanol to yield a colorless solid in 20% yield (0.012 g); m.p. 260-262° C.; $^1$H NMR (DMSO-d$_6$, 300 MHz) δ 13.11 (s, br., 1H), 8.63 (t, J=5.8 Hz, 1H), 7.78 (d, J=7.1 Hz, 1H), 7.58-7.37 (m, 5H), 7.35-7.26 (m, 4H), 7.23-7.18 (m, 1H), 7.14 (d, J=1.5 Hz, 1H), 6.75 (dd, J=1.5, 7.1 Hz, 1H), 4.38 (d, J=5.8 Hz, 2H), 2.51 (s, 3H); $^{13}$C NMR (DMSO-d$_6$, 75 MHz) δ 165.5, 162.0, 162.0, 161.3, 140.7, 140.2, 140.0, 139.9, 137.9, 129.6, 128.9, 128.7, 127.7, 127.2, 127.0, 120.9, 103.7, 43.1, 16.9; MS (ES+) m/z 445.0 (M+1).

Example 16

Synthesis of N,4-Dibenzyl-2-(3-phenylpropanamido)thiazole-5-carboxamide

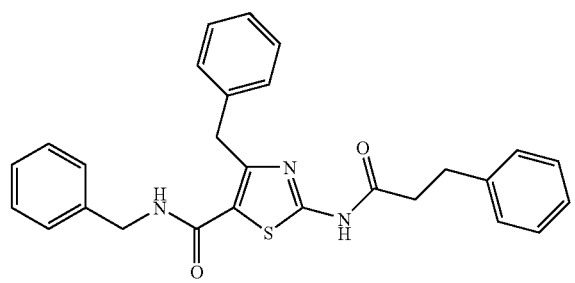 [SMILES: O=C(CCc1ccccc1)Nc1nc(Cc2ccccc2)c(C(=O)NCc2ccccc2)s1]

To a solution of 2-amino-N,4-dibenzylthiazole-5-carboxamide (0.053 g, 0.16 mmol) in tetrahydrofuran (5 mL) at 0° C. was added hydrocinnamoyl chloride (0.03 mL, 0.20 mmol), DMAP (cat.) and triethylamine (0.3 mL, 2.10 mmol). The reaction mixture was allowed to warm to ambient temperature over 18 h then concentrated in vacuo. The crude product was purified by flash column chromatography eluting with ethyl acetate/hexanes (5/95 to 100/0) to afford the title compound in 49% yield (0.036 g); $^1$H NMR (CDCl$_3$, 400 MHz) δ 7.35-7.15 (m, 15H), 4.56 (d, J=5.6 Hz, 2H), 4.37 (s, 2H), 3.03 (t, J=7.6 Hz, 2H), 2.74 (t, J=7.6 Hz, 2H); MS (ES+) m/z 456 (M+1).

Example 16.1

Synthesis of 2-Benzamido-N,4-dibenzylthiazole-5-carboxamide

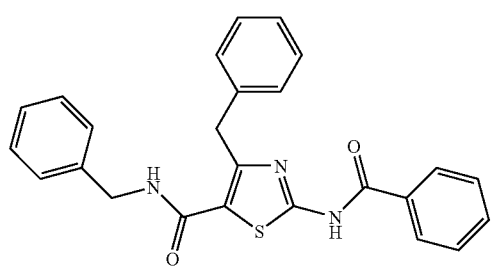 [SMILES: O=C(Nc1nc(Cc2ccccc2)c(C(=O)NCc2ccccc2)s1)c1ccccc1]

Following the procedure as described in Example 16, making variations only as required to use benzoyl chloride in place of hydrocinnamoyl chloride to react with 2-amino-N,4-dibenzylthiazole-5-carboxamide, the title compound was obtained in 54% yield; $^1$H NMR (CDCl$_3$, 400 MHz) δ 7.92 (d, J=7.1 Hz, 2H), 7.63 (t, J=7.6 Hz, 1H), 7.52 (t, J=8.1 Hz, 2H), 7.40-7.15 (m, 10H), 4.58 (d, J=5.6 Hz, 2H), 4.41 (s, 2H); MS (ES+) m/z 428 (M+1).

Example 17

Synthesis of N-Benzyl-4-methyl-2-(N-methylbenzamido)thiazole-5-carboxamide

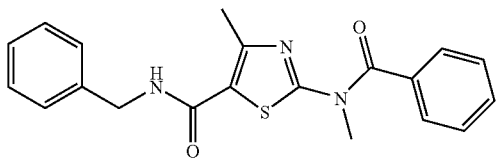 [SMILES: Cc1nc(N(C)C(=O)c2ccccc2)sc1C(=O)NCc1ccccc1]

A. To a stirred solution of 2-(tert-butoxycarbonylamino)-4-methylthiazole-5-carboxylic acid (0.13 g, 0.50 mmol) in N,N-dimethylformamide (2.5 mL) at 0° C. was added sodium hydride (0.044 g, 1.10 mmol, 60% dispersed in mineral oil). The resultant mixture was stirred at 0° C. for 40 min, followed by the dropwise addition of iodomethane (31.2 mL, 0.50 mmol). The resultant solution was allowed to warm to ambient temperature over 18 h, followed by the addition of saturated sodium bicarbonate solution. The mixture was extracted with ethyl acetate. The combined organic layer was dried over anhydrous sodium sulfate, filtered, and concentrated in vacuo. The crude product was purified by flash column chromatography eluting with ethyl acetate/hexanes (50/50 to 100/0) to afford 2-(tert-butoxycarbonyl(methyl)amino)-4-methylthiazole-5-carboxylic acid (0.070 g, 0.26 mmol).

B. To a solution of 2-(tert-butoxycarbonyl(methyl)amino)-4-methylthiazole-5-carboxylic acid (0.070 g, 0.26 mmol) in dichloromethane (2 mL) at 0° C. was added N,N,N',N'-tetramethyl-O-(7-azabenzotriazol-1-yl)uronium hexafluorophosphate (0.15 g, 0.39 mmol), followed by the addition of benzylamine (29.5 µL, 0.27 mmol), 4-dimethylaminopyridine (catalytical amount), and triethylamine (72 µL, 0.52 mmol). The reaction mixture was allowed to warm to ambient temperature over 3 h, followed by the addition of saturated sodium bicarbonate solution. The mixture was extracted with ethyl acetate. The combined organic layer was dried over anhydrous sodium sulfate, filtered, and concentrated in vacuo. The crude product was purified by flash column chromatography eluting with ethyl acetate/hexanes (5/95 to 100/0) to afford tert-butyl 5-(benzylcarbamoyl)-4-methylthiazol-2-yl(methyl)carbamate (0.030 g, 0.083 mmol).

C. To a solution of tert-butyl 5-(benzylcarbamoyl)-4-methylthiazol-2-yl(methyl)carbamate (0.030 g, 0.083 mmol) in dichloromethane (1 mL) was added trifluoroacetic acid (1 mL) and the resultant mixture was stirred at ambient temperature for 4 h. Toluene (0.5 mL) was added and the reaction mixture was concentrated in vacuo. The residue was triturated with diethyl ether and concentrated in vacuo and dried in vacuum. The crude N-benzyl-4-methyl-2-(methylamino)thiazole-5-carboxamide was obtained and used directly in the next step.

D. To a solution of crude N-benzyl-4-methyl-2-(methylamino)thiazole-5-carboxamide (0.040 g, 0.15 mmol), 4-dimethylaminopyridine (catalytical amount) and triethylamine (64 µL, 0.45 mmol) in dichloromethane (5 mL) was added benzoyl chloride (19 µL, 0.17 mmol) at 0° C. and the reaction mixture was allowed to warm to ambient temperature over 18 h. The reaction was quenched by the addition of saturated soldium bicarbonate solution. The mixture was extracted with ethyl acetate. The organic layer was combined, washed with brine, dried over anhydrous magnesium sulphate, filtered and concentrated in vacuo. The crude product was purified by flash column chromatography eluting with ethyl acetate/hexanes (30/70 to 50/50) to afford the title compound (0.040 g, 0.11 mmol); ¹H NMR (CDCl₃, 400 MHz) δ 7.47-7.35 (m, 5H), 7.30-7.17 (m, 5H), 6.05 (s, 1H), 4.51 (s, J=5.6 Hz, 2H), 3.55 (s, 3H), 2.60 (s, 3H); MS (ES+) m/z 366 (M+1).

Example 18

Synthesis of N-benzyl-N,4-dimethyl-2-(N-methylbenzamido)thiazole-5-carboxamide

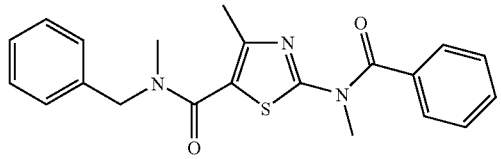 [SMILES: Cc1nc(N(C)C(=O)c2ccccc2)sc1C(=O)N(C)Cc1ccccc1]

To a stirred solution of 2-benzoylamino-4-methylthiazole-5-carboxylic acid benzylamide (0.020 g, 1.0 equiv) in N,N-dimethylformamide (0.5 mL) at 0° C. was added sodium hydride (0.007 g, 3.0 equiv, 60% dispersed in mineral oil). The resultant mixture was stirred at 0° C. for 10 minutes, followed by the dropwise addition of iodomethane (8.5 µL, 2.4 equiv). The resultant solution was allowed to warm to ambient temperature over 2 h, followed by the addition of saturated sodium bicarbonate solution. The mixture was extracted with ethyl acetate. The combined organic layer was washed with brine, dried over anhydrous sodium sulfate, filtered, and concentrated in vacuo. The crude product was purified by flash column chromatography eluting with ethyl acetate/hexanes (50/50 to 70/30) to afford the title compound (0.012 g); ¹H NMR (CDCl₃, 400 MHz) δ 2.41 (s, 3H), 2.99 (s, 3H), 3.80 (s, 3H), 4.67 (s, 2H), 7.20-7.51 (m, 8H), 8.25 (d, J=7.1 Hz, 2H); MS (ES+) m/z 380 (M+1).

Example 19

Synthesis of 2-(4-((1H-pyrazol-1-yl)methyl)benzamido)-N-benzyl-4-methylthiazole-5-carboxamide

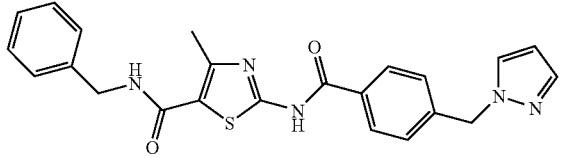 [SMILES: Cc1nc(NC(=O)c2ccc(Cn3cccn3)cc2)sc1C(=O)NCc1ccccc1]

To a solution of 2-amino-4-methylthiazole-5-carboxylic acid benzylamide (0.47 g, 1.88 mmol), and N-methylmorpholine (0.23 mL, 2.08 mmol) in N,N-dimethylformamide (20 mL) at 0° C. was added (benzotriazol-1-yloxy)tris(dimethylamino)phosphonium hexafluorophosphate (0.42 g, 2.09 mmol) and 4-pyrazol-1-ylmethyl-benzoic acid (0.42 g, 2.09 mmol). The resultant solution was allowed to warm to ambient temperature over 18 h, and concentrated in vacuo. The crude product was purified by flash column chromatography eluting with methanol/dichloromethane (0/100 to 30/70) to afford the title compound (1.11 g); MS (ES+) m/z 432 (M+1).

Example 20

Synthesis of N-benzyl-2-(4-benzylbenzamido)-4-methylthiazole-5-carboxamide

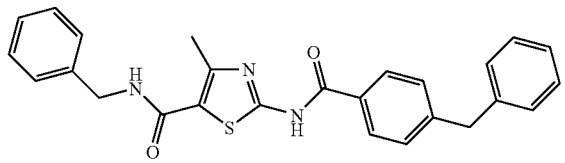 [SMILES: Cc1nc(NC(=O)c2ccc(Cc3ccccc3)cc2)sc1C(=O)NCc1ccccc1]

To a solution of 2-amino-4-methyl-thiazole-5-carboxylic acid benzylamide (0.054 g, 0.22 mmol) and diisopropylethylamine (0.40 mL, 2.3 mmol) in dichloromethane (5 mL) was added 4-benzylbenzoic acid (0.057 g, 0.27 mmol), followed by the addition of N,N,N',N'-tetramethyl-O-(7-azabenzotriazol-1-yl)uronium hexafluorophosphate (0.11 g, 0.28 mmol). The reaction was stirred at ambient temperature over 18 h then concentrated in vacuo. The crude product was purified by preparative HPLC (acetone/water gradient) to afford the title compound (0.003 g); MS (ES+) m/z 442 (M+1).

Example 21

Synthesis of 2-(4-Benzylbenzamido)-N-ethyl-4-methylthiazole-5-carboxamide

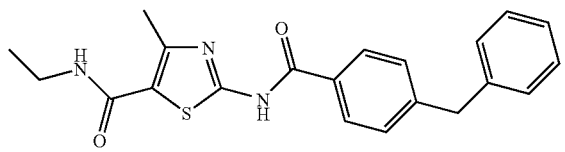 [SMILES: CCNC(=O)c1sc(NC(=O)c2ccc(Cc3ccccc3)cc2)nc1C]

To a solution of 2-amino-N-ethyl-4-methylthiazole-5-carboxamide (0.17 g, 0.93 mmol) in dichloromethane (2 mL) at −78° C. was added sodium hydride (excess) followed by the addition of 4-benzylbenzoyl chloride (1 equiv of 0.5 M in N,N-dimethylformamide). The reaction was allowed to warm to ambient temperature over 18 h then concentrated in vacuo. The crude product was purified by preparative HPLC (acetone/water gradient) to afford the title compound (0.005 g); $^1$H NMR (CD$_3$OD, 400 MHz) δ 7.90 (d, J=8.6 Hz, 2H), 7.35 (d, J=8.1 Hz, 2H), 7.27-7.13 (m, 5H), 4.03 (s, 2H), 3.32 (q, J=7.6 Hz, 2H), 2.50 (s, 3H), 1.17 (t, J=7.6 Hz, 3H); MS (ES+) m/z 380 (M+1).

Example 21.1

Synthesis of 2-(4-Benzylbenzamido)-N-(2-cyanoethyl)-4-methylthiazole-5-carboxamide

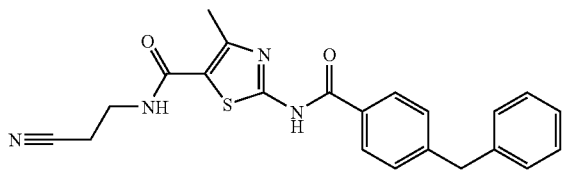 [SMILES: Cc1nc(NC(=O)c2ccc(Cc3ccccc3)cc2)sc1C(=O)NCCC#N]

Following the procedure as described in Example 20, making variation only as required to use 2-amino-N-(2-cyanoethyl)-4-methylthiazole-5-carboxamide to replace 2-amino-N-ethyl-4-methylthiazole-5-carboxamide to react with 4-benzylbenzoyl chloride, the title compound was obtained; $^1$H NMR (CD$_3$OD, 400 MHz) δ 7.90 (d, J=8.1 Hz, 2H), 7.35 (d, J=8.6 Hz, 2H), 7.27-7.10 (m, 5H), 4.03 (s, 2H), 3.54 (t, J=6.6 Hz, 2H), 2.73 (t, J=6.6 Hz, 2H), 2.54 (s, 3H), 2.32 (s, 1H); MS (ES+) m/z 405 (M+1).

Example 22

Synthesis of N-Benzyl-4-(morpholinomethyl)-2-(3-phenylpropanamido)thiazole-5-carboxamide

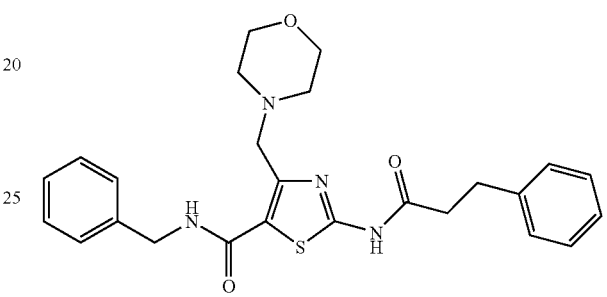

A. To a stirred solution of 2-(tert-butoxycarbonylamino)-4-methylthiazole-5-carboxylic acid (2.97 g, 11.50 mmol) and diisopropylamine (8.5 mL, 48.70 mmol) in dichloromethane (40 mL) was added N-ethyl-N'-(3-dimethylaminopropyl)carbodiimide hydrochloride (2.25 g, 11.50 mmol) and 1-hydroxybenzotriazole (2.02 g, 14.80 mmol). After 30 min benzylamine (1.7 mL, 15.60 mmol) was added. The resultant mixture was stirred at ambient temperature over 8 h, diluted with ethyl acetate, washed with water and brine, dried over anhydrous sodium sulfate, filtered and concentrated in vacuo. The crude product was purified by flash column chromatography eluting with ethyl acetate/hexanes (5/95 to 100/0) to afford 2-(tert-butoxycarbonylamino)-4-methylthiazole-5-carboxylic acid benzylamide (2.00 g, 50% yield).

B. To a solution of 2-(tert-butoxycarbonylamino)-4-methylthiazole-5-carboxylic acid benzylamide (0.108 g, 0.31 mmol) in acetonitrile (10 mL) was added N-bromosuccinimide (0.071 g, 0.40 mmol). The resultant mixture was stirred at ambient temperature until the reaction was completed. The reaction mixture was concentrated in vacuo and the crude product was purified by flash column chromatography eluting with ethyl acetate/hexanes (5/95 to 100/0) to afford 2-(tert-butoxycarbonylamino)-4-bromomethylthiazole-5-carboxylic acid benzylamide (0.077 g, 58% yield).

C. To a solution of 2-(tert-butoxycarbonylamino)-4-bromomethylthiazole-5-carboxylic acid benzylamide (0.077 g, 0.18 mmol) and triethylamine (0.03 mL, 0.23 mmol) in acetonitrile (5 mL) was added morpholine (0.13 mL, 1.5 mmol) and the reaction mixture was stirred at ambient temperature for 12 h. The solution was then concentrated in vacuo and the crude 2-(tert-butoxycarbonylamino)-4-morpholin-4-ylmethylthiazole-5-carboxylic acid benzylamide was used directly in the next step.

D. A solution of crude 2-(tert-butoxycarbonylamino)-4-morpholin-4-ylmethylthiazole-5-carboxylic acid benzylamide (0.18 mmol) from the previous step in methanol (5 mL) was treated with hydrochloric acid solution (3 mL, 4 M solution in dioxanes) and the reaxtion mixture was stirred at ambient temperature until the reaction was completed. The mixture was then concentrated and purified by preparative HPLC (acetone/water gradient) to afford 2-amino-4-morpholin-4-ylmethylthiazole-5-carboxylic acid benzylamide (0.030 g).

E. To a solution of 2-amino-4-morpholin-4-ylmethylthiazole-5-carboxylic acid benzylamide (0.030 g, 0.09 mmol) in tetrahydrofuran (5 mL) at 0° C. was added hydrocinnamoyl chloride (0.1 mL, 0.67 mmol), 4-dimethylaminopyridine (catalytical amount) and triethylamine (0.2 mL, 1.4 mmol). The reaction mixture was allowed to warm to ambient temperature over 18 h then concentrated in vacuo. The crude product was purified by flash column chromatography eluting with ethyl acetate/hexanes (5/95 to 100/0) to afford the title compound (0.031 g); $^1$H NMR (DMSO-$d_6$, 400 MHz) δ 7.40-7.15 (m, 10H), 4.46 (d, J=5.1 Hz, 2H), 3.62 (s, 2H), 3.19 (bs, 4H), 2.91 (t, J=7.6 Hz, 2H), 2.74 (t, J=8.1 Hz, 2H), 2.24 (br, s, 4H); MS (ES+) m/z 465 (M+1).

Example 23

Synthesis of N-Benzyl-2-(4-benzylbenzamido)-4-((diethylamino)methyl)thiazole-5-carboxamide

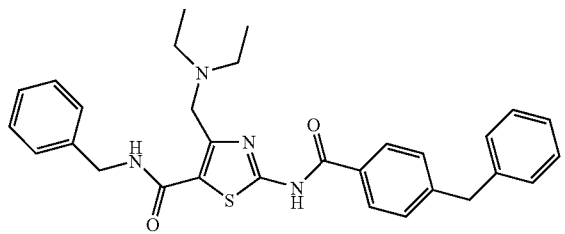 [SMILES: CCN(CC)Cc1nc(NC(=O)c2ccc(Cc3ccccc3)cc2)sc1C(=O)NCc1ccccc1]

To a solution of 2-amino-N-benzyl-4-((diethylamino)methyl)thiazole-5-carboxamide (0.052 g, 0.16 mmol) and diisopropylethylamine (0.30 mL, 1.70 mmol) in dichloromethane (5 mL) was added 4-benzylbenzoic acid (0.046 g, 0.21 mmol) followed by the addition of N,N,N',N'-tetramethyl-O-(7-azabenzotriazol-1-yl)uronium hexafluorophosphate (0.076 g, 0.20 mmol). The reaction mixture was stirred at ambient temperature for 18 h, diluted with ethyl acetate and washed with saturated sodium bicarbonate solution, brine, dried over anhydrous magnesium sulfate, filtered and concentrated in vacuo. The crude product was purified by preparative HPLC (acetone/water gradient) to afford the title compound (0.003 g); MS (ES+) m/z 513.

Example 23.1

Synthesis of N-Benzyl-2-(4-benzylbenzamido)-4-((methylamino)methyl)thiazole-5-carboxamide

Following the procedure as described in Example 22, making variation only as required to use 2-amino-N-benzyl-4-((methylamino)methyl)thiazole-5-carboxamide in place of 2-amino-N-benzyl-4-((diethylamino)methyl)thiazole-5-carboxamide to react with 4-benzylbenzoic acid, the title compound was obtained; $^1$H NMR (CD$_3$OD, 400 MHz) δ 7.93 (d, J=8.6 Hz, 2H), 7.35-7.15 (m, 12H), 4.49 (s, 2H), 4.06 (s, 2H), 4.02 (s, 2H), 3.09 (s, 2H), 2.37 (s, 3H); MS (ES+) m/z 471 (M+1).

Example 24

Synthesis of 2-Benzamido-N-benzyl-4-((diethylamino)methyl)thiazole-5-carboxamide

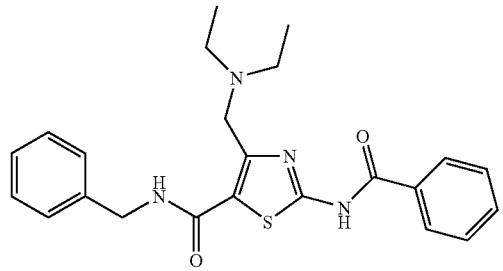 [SMILES: CCN(CC)Cc1nc(NC(=O)c2ccccc2)sc1C(=O)NCc1ccccc1]

To a solution of 2-amino-4-diethylaminomethylthiazole-5-carboxylic acid benzylamide (0.052 g, 0.16 mmol) in tetrahydrofuran (5 mL) at 0° C. were added benzoyl chloride (0.04 mL, 0.34 mmol), 4-dimethylaminopyridine (catalytical amount) and triethylamine (0.3 mL, 2.10 mmol). The reaction mixture was allowed to warm to ambient temperature over 18 h then concentrated in vacuo. The crude product was purified by flash column chromatography eluting with methanol/dichloromethane (1/40 to 20/80) to afford the title compound (0.021 g); MS (ES+) m/z 423 (M+1).

Example 25

Synthesis of Ethyl 2-(Isonicotinamido)-4-methylthiazole-5-carboxylate

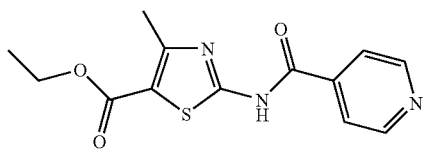 [SMILES: CCOC(=O)c1sc(NC(=O)c2ccncc2)nc1C]

To a mixture of ethyl 2-amino-4-methylthiazole-5-carboxylate (5.70 g, 30.60 mmol) and triethylamine (10.0 mL, 71.80 mmol) in tetrahydrofuran (100 mL) was added isonicotinoyl chloride hydrochloride (6.00 g, 32.00 mmol). The reaction mixture was stirred at ambient temperature for 2 days. The solvent was removed by evaporation and the resulting white solid was washed sequentially with water, 10% sodium bicarbonate solution, and water, then dried to afford the title compound in 90% yield (8.10 g); $^1$H NMR (DMSO-d$_6$, 300 MHz) δ 8.77 (d, J=6.0 Hz, 2H), 8.77 (d, J=6.0 Hz, 2H), 4.23 (q, J=7.2 Hz, 2H), 2.34 (s, 3H). 1.27 (t, J=7.2 Hz, 3H); MS (ES+) m/z 292.0 (M+1).

Example 26

Synthesis of Ethyl 2-Benzamido-4-phenylthiazole-5-carboxylate

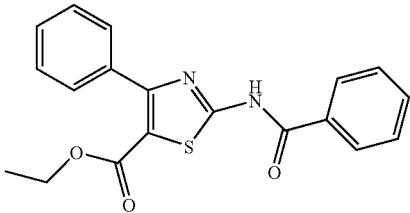 [SMILES: CCOC(=O)c1sc(NC(=O)c2ccccc2)nc1-c1ccccc1]

To a stirred cold mixture of ethyl 2-amino-4-phenylthiazole-5-carboxylate (1.24 g, 5.00 mmol), 4-dimethylaminopyridine (0.10 g, 16 mol %) and pyridine (4.0 mL, 10 equiv) in dichloromethane (20.0 mL) was added benzoyl chloride (0.70 g, 5.00 mmol) in dichloromethane (3 mL). The mixture was stirred at ambient temperature for 2 h, then washed with 5% hydrochloric acid solution, water, and dried over anhydrous sodium sulfate. Removal of the solvent afforded the title compound in 92% yield (1.62 g); $^1$H NMR (CDCl$_3$, 300 MHz) δ 10.10 (s, 1H), 8.15 (d, J=7.2 Hz, 2H), 7.85-7.45 (m, 8H), 4.24 (q, J=5.9 Hz, 2H), 1.19 (t, J=5.9 Hz, 3H); MS (ES$^+$) m/z 353.1 (M+1).

Example 27

Preparation of Ethyl 2-Benzamido-4-methylthiazole-5-carboxylate

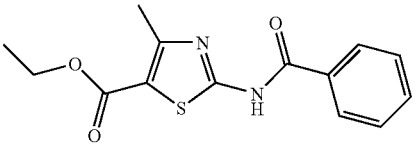 [SMILES: CCOC(=O)c1sc(NC(=O)c2ccccc2)nc1C]

To a solution of ethyl 2-amino-4-methylthiazole-5-carboxylate (2.00 g, 10.00 mmol) in anhydrous dichloromethane (40 mL) was added pyridine (2.50 g, 32.00 mmol), followed by the addition of benzoyl chloride (1.90 g, 13.00 mmol) dropwise. The reaction mixture was stirred at ambient temperature for 18 h, then washed sequentially with 1 N hydrochloric acid (15 mL), saturated aqueous sodium bicarbonate (2×15 mL), and water (15 mL), dried over anhydrous sodium sulfate and filtered. The filtrate was concentrated in vacuo. The residue was purified by column chromatography to afford the title compound as a white solid in 97% yield (3.0 g); $^1$H NMR (CDCl$_3$, 300 MHz) δ 11.35 (s, br, 1H), 7.89 (d, J=7.4 Hz, 2H), 7.59 (t, J=7.4 Hz, 1H), 7.47 (t, J=7.6 Hz, 2H), 4.29 (q, J=7.1 Hz, 2H), 2.28 (s, 3H), 1.35 (t, J=7.1 Hz, 3H); MS (ES+) m/z 291.1 (M+1).

Example 28

The following additional compounds of formula (I) were synthesized by the synthetic processes described herein or by methods known to one skilled in the art:

2-(4-Bromobenzoylamino)-4-methylthiazole-5-carboxylic acid o-tolylamide;
2-(4-Bromobenzoylamino)-4-methylthiazole-5-carboxylic acid (2-chlorophenyl)amide;
2-(4-Bromobenzoylamino)-4-methylthiazole-5-carboxylic acid (3-methoxyphenyl)amide;
4-Methyl-2-(3,4,5-trimethoxybenzoylamino)thiazole-5-carboxylic acid phenylamide;
4-Methyl-2-(4-methylbenzoylamino)thiazole-5-carboxylic acid (4-methoxyphenyl)amide;
4-Methyl-2-[(thiophene-2-carbonyl)amino]thiazole-5-carboxylic acid (4-chlorophenyl)amide;
2-(Cyclohexanecarbonylamino)-4-methylthiazole-5-carboxylic acid (2,3-dihydro-benzo[1,4]dioxin-6-yl)amide;
2-(4-Methoxybenzoylamino)-4-methylthiazole-5-carboxylic acid pyridin-3-ylamide;
2-Benzoylamino-4-methylthiazole-5-carboxylic acid (5-methyl[1,3,4]thiadiazol-2-yl)amide;
2-[(Furan-2-carbonyl)amino]-4-methylthiazole-5-carboxylic acid o-tolylamide;
2-[(Furan-2-carbonyl)amino]-4-methylthiazole-5-carboxylic acid (4-bromophenyl)amide;
2-(3-Methoxybenzoylamino)-4-methylthiazole-5-carboxylic acid (4-bromophenyl)amide;
2-[(Furan-2-carbonyl)amino]-4-methylthiazole-5-carboxylic acid (4-chlorophenyl)amide;
2-[(Furan-2-carbonyl)amino]-4-methylthiazole-5-carboxylic acid (3-methoxyphenyl)amide;
2-[(Furan-2-carbonyl)amino]-4-methylthiazole-5-carboxylic acid (4-methoxyphenyl)amide;
4-Methyl-2-(2-phenoxyacetylamino)thiazole-5-carboxylic acid phenylamide;
4-Methyl-2-(2-phenoxyacetylamino)thiazole-5-carboxylic acid benzylamide;
2-Chloro-N-[4-methyl-5-(morpholine-4-carbonyl)thiazol-2-yl]benzamide;
2-(3-Fluorobenzoylamino)-4-methylthiazole-5-carboxylic acid (4-bromophenyl)amide;
2-(2-Fluorobenzoylamino)-4-methylthiazole-5-carboxylic acid (4-bromophenyl)amide;
2-Acetylamino-4-methylthiazole-5-carboxylic acid indan-5-ylamide;
2-Acetylamino-4-methylthiazole-5-carboxylic acid cyclohexylamide;
2-(4-Fluorobenzoylamino)-4-methylthiazole-5-carboxylic acid (4-bromophenyl)amide;
2-Benzoylamino-4-methylthiazole-5-carboxylic acid phenylamide;
2-Benzoylamino-4-methylthiazole-5-carboxylic acid (3-methoxyphenyl)amide;
2-(4-Fluorobenzoylamino)-4-methylthiazole-5-carboxylic acid (4-methoxyphenyl)amide;
4-Methyl-2-propionylamino-thiazole-5-carboxylic acid indan-5-ylamide;
2-(Cyclopropanecarbonylamino)-4-methylthiazole-5-carboxylic acid phenylamide;
2-(Cyclopropanecarbonylamino)-4-methylthiazole-5-carboxylic acid (4-chlorophenyl)amide;
2-(4-Fluorobenzoylamino)-4-methylthiazole-5-carboxylic acid phenylamide;
2-(4-Fluorobenzoylamino)-4-methylthiazole-5-carboxylic acid o-tolylamide;
2-(4-Fluorobenzoylamino)-4-methylthiazole-5-carboxylic acid (4-chlorophenyl)amide;
2-(4-Fluorobenzoylamino)-4-methylthiazole-5-carboxylic acid (2-chlorophenyl)amide;

2-(4-Fluorobenzoylamino)-4-methylthiazole-5-carboxylic acid (3-methoxyphenyl)amide;
N-[4-Methyl-5-(piperidine-1-carbonyl)thiazol-2-yl]benzamide;
2-(Cyclopropanecarbonylamino)-4-methylthiazole-5-carboxylic acid indan-5-ylamide;
4-Methyl-2-(4-methylbenzoylamino)thiazole-5-carboxylic acid pyridin-3-ylamide;
[(2-Benzoylamino-4-methylthiazole-5-carbonyl)amino]acetic acid ethyl ester;
N-[4-Methyl-5-(morpholine-4-carbonyl)thiazol-2-yl]propionamide;
N-[5-(3-Chlorophenylcarbamoyl)-4-methylthiazol-2-yl]isonicotinamide;
N-[5-(2-Chlorophenylcarbamoyl)-4-methylthiazol-2-yl]isonicotinamide;
N-(4-Oxo-5,6,7,8-tetrahydro-4H-thiazolo[5,4-c]azepin-2-yl)acetamide;
N-(7,7-Dimethyl-4-oxo-5,6,7,8-tetrahydro-4H-thiazolo[5,4-c]azepin-2-yl)acetamide;
2-(3-Fluorobenzoylamino)-4-methylthiazole-5-carboxylic acid phenylamide;
4-Methyl-2-(4-methylbenzoylamino)thiazole-5-carboxylic acid o-tolylamide;
2-(2-Fluorobenzoylamino)-4-methylthiazole-5-carboxylic acid o-tolylamide;
2-(4-Bromobenzoylamino)-4-methylthiazole-5-carboxylic acid (4-chlorophenyl)amide;
4-Methyl-2-(3,4,5-trimethoxybenzoylamino)thiazole-5-carboxylic acid (4-chlorophenyl)amide;
2-(4-Bromobenzoylamino)-4-methylthiazole-5-carboxylic acid (3-chlorophenyl)amide;
4-Methyl-2-(3-methylbenzoylamino)thiazole-5-carboxylic acid (3-chlorophenyl)amide;
2-(3-Fluorobenzoylamino)-4-methylthiazole-5-carboxylic acid (3-chlorophenyl)amide;
4-Methyl-2-(2-methylbenzoylamino)thiazole-5-carboxylic acid (2-chlorophenyl)amide;
4-Methyl-2-(3,4,5-trimethoxybenzoylamino)thiazole-5-carboxylic acid (2-chlorophenyl)amide;
4-Methyl-2-(3-methylbenzoylamino)thiazole-5-carboxylic acid (2-chlorophenyl)amide;
2-(3-Fluorobenzoylamino)-4-methylthiazole-5-carboxylic acid (2-chlorophenyl)amide;
2-(4-Bromobenzoylamino)-4-methylthiazole-5-carboxylic acid (2,3-dihydro-benzo[1,4]dioxin-6-yl)amide;
2-(4-Methoxybenzoylamino)-4-methylthiazole-5-carboxylic acid (2,3-dihydro-benzo[1,4]dioxin-6-yl)amide;
4-Methyl-2-(3-methylbenzoylamino)thiazole-5-carboxylic acid (2,3-dihydro-benzo[1,4]dioxin-6-yl)amide;
2-(4-Bromobenzoylamino)-4-methylthiazole-5-carboxylic acid benzylamide;
2-(4-Bromobenzoylamino)-4-methylthiazole-5-carboxylic acid indan-5-ylamide;
4-Methyl-2-(3-methylbenzoylamino)thiazole-5-carboxylic acid indan-5-ylamide;
4-Methyl-2-(3,4,5-trimethoxybenzoylamino)thiazole-5-carboxylic acid cyclohexylamide;
2-Fluoro-N-[4-methyl-5-(piperidine-1-carbonyl)thiazol-2-yl]benzamide;
4-Bromo-N-[4-methyl-5-(morpholine-4-carbonyl)thiazol-2-yl]benzamide;
4-Methoxy-N-[4-methyl-5-(morpholine-4-carbonyl)thiazol-2-yl]benzamide;
2-(Cyclohexanecarbonylamino)-4-methylthiazole-5-carboxylic acid (4-methoxyphenyl)amide;
4-Methyl-2-(3,4,5-trimethoxybenzoylamino)thiazole-5-carboxylic acid o-tolylamide;
4-Methyl-2-(3,4,5-trimethoxybenzoylamino)thiazole-5-carboxylic acid (3-chlorophenyl)amide;
2-(4-Methoxy-benzoylamino)-4-methylthiazole-5-carboxylic acid (3-methoxyphenyl)amide;
4-Methyl-2-(4-methylbenzoylamino)thiazole-5-carboxylic acid (2,3-dihydro-benzo[1,4]dioxin-6-yl)amide;
4-Methyl-2-(3,4,5-trimethoxybenzoylamino)thiazole-5-carboxylic acid (2,3-dihydro-benzo[1,4]dioxin-6-yl)amide;
4-Methyl-2-(4-methylbenzoylamino)thiazole-5-carboxylic acid benzylamide;
4-Methyl-2-(4-methylbenzoylamino)thiazole-5-carboxylic acid indan-5-ylamide;
4-Methyl-2-(4-methylbenzoylamino)thiazole-5-carboxylic acid (4-chlorophenyl)amide;
4-Methyl-2-(4-methylbenzoylamino)thiazole-5-carboxylic acid (3-chlorophenyl)amide;
4-Methyl-2-(4-methylbenzoylamino)thiazole-5-carboxylic acid (2-chlorophenyl)amide;
4-Methyl-2-(4-methylbenzoylamino)thiazole-5-carboxylic acid (3-methoxyphenyl)amide;
4-Methyl-2-(4-methylbenzoylamino)thiazole-5-carboxylic acid phenylamide;
2-(Cyclohexanecarbonylamino)-4-methylthiazole-5-carboxylic acid (4-chlorophenyl)amide;
2-(Cyclohexanecarbonylamino)-4-methylthiazole-5-carboxylic acid (2-chlorophenyl)amide;
3-Methyl-1-phenyl-1H-thieno[2,3-c]pyrazole-5-carboxylic acid [5-(2-chloro-phenylcarbamoyl)-4-methylthiazol-2-yl]amide;
2-(Cyclohexanecarbonylamino)-4-methylthiazole-5-carboxylic acid indan-5-ylamide;
{[2-(4-Methoxybenzoylamino)-4-methylthiazole-5-carbonyl]amino}acetic acid ethyl ester;
3-Fluoro-N-[4-methyl-5-(morpholine-4-carbonyl)thiazol-2-yl]benzamide;
2-[(5-Chloro-3-methyl-1-phenyl-1H-pyrazole-4-carbonyl)amino]-4-methylthiazole-5-carboxylic acid cyclohexylamide;
4-Methyl-2-(3-phenylacryloylamino)thiazole-5-carboxylic acid (2-dimethylaminoethyl)amide;
2-[(Furan-2-carbonyl)amino]-4-methylthiazole-5-carboxylic acid phenylamide;
2-[(Adamantane-1-carbonyl)amino]-4-methylthiazole-5-carboxylic acid phenylamide;
2-[(Adamantane-1-carbonyl)amino]-4-methylthiazole-5-carboxylic acid (4-bromophenyl)amide;
2-(3-Methoxy-benzoylamino)-4-methylthiazole-5-carboxylic acid (4-chlorophenyl)amide;
2-[(Furan-2-carbonyl)amino]-4-methylthiazole-5-carboxylic acid (3-chlorophenyl)amide;
2-(3-Methoxybenzoylamino)-4-methylthiazole-5-carboxylic acid (3-chlorophenyl)amide;
2-(3-Methoxybenzoylamino)-4-methylthiazole-5-carboxylic acid (2-chlorophenyl)amide;
2-(3-Methoxybenzoylamino)-4-methylthiazole-5-carboxylic acid (2,3-dihydro-benzo[1,4]dioxin-6-yl)amide;
2-(3-Methoxybenzoylamino)-4-methylthiazole-5-carboxylic acid indan-5-ylamide;
{[2-(3-Methoxybenzoylamino)-4-methylthiazole-5-carbonyl]amino}acetic acid ethyl ester;
2-(4-Bromobenzoylamino)-4-methylthiazole-5-carboxylic acid (5-methyl[1,3,4]thiadiazol-2-yl)amide;
2-(3-Methoxybenzoylamino)-4-methylthiazole-5-carboxylic acid (4-methoxyphenyl)amide;

2-[(Adamantane-1-carbonyl)amino]-4-methylthiazole-5-carboxylic acid (4-methoxyphenyl)amide;
3-Methyl-1-phenyl-1H-thieno[2,3-c]pyrazole-5-carboxylic acid (4-methyl-5-phenylcarbamoyl-thiazol-2-yl)amide;
3-Methyl-1-phenyl-1H-thieno[2,3-c]pyrazole-5-carboxylic acid (4-methyl-5-o-tolylcarbamoyl-thiazol-2-yl)amide;
2-[(5-Chloro-3-methyl-1-phenyl-1H-pyrazole-4-carbonyl)amino]-4-methylthiazole-5-carboxylic acid (4-bromophenyl)amide;
2-[(5-Chloro-3-methyl-1-phenyl-1H-pyrazole-4-carbonyl)amino]-4-methylthiazole-5-carboxylic acid (2-chlorophenyl)amide;
3-Methyl-1-phenyl-1H-thieno[2,3-c]pyrazole-5-carboxylic acid [5-(2,3-dihydro-benzo[1,4]dioxin-6-ylcarbamoyl)-4-methylthiazol-2-yl]amide;
3-Methyl-1-phenyl-1H-thieno[2,3-c]pyrazole-5-carboxylic acid [5-(indan-5-ylcarbamoyl)-4-methylthiazol-2-yl]amide;
3-Methyl-1-phenyl-1H-thieno[2,3-c]pyrazole-5-carboxylic acid [4-methyl-5-(5-methyl-[1,3,4]thiadiazol-2-ylcarbamoyl)thiazol-2-yl]amide;
3-Methyl-1-phenyl-1H-thieno[2,3-c]pyrazole-5-carboxylic acid [4-methyl-5-(piperidine-1-carbonyl)thiazol-2-yl]amide;
3-Methyl-N-[4-methyl-5-(piperidine-1-carbonyl)thiazol-2-yl]benzamide;
3-Methyl-1-phenyl-1H-thieno[2,3-c]pyrazole-5-carboxylic acid [5-(4-methoxy-phenylcarbamoyl)-4-methylthiazol-2-yl]amide;
4-Methyl-2-(4-methylbenzoylamino)thiazole-5-carboxylic acid cyclohexylamide;
2-(Cyclohexanecarbonylamino)-4-methylthiazole-5-carboxylic acid (3-chlorophenyl)amide;
4-Methyl-2-[(thiophene-2-carbonyl)amino]thiazole-5-carboxylic acid (2,3-dihydro-benzo[1,4]dioxin-6-yl)amide;
2-[(Adamantane-1-carbonyl)amino]-4-methylthiazole-5-carboxylic acid benzylamide;
4-Methyl-2-(4-methylbenzoylamino)thiazole-5-carboxylic acid (4-bromophenyl)amide;
2-(Cyclohexanecarbonylamino)-4-methylthiazole-5-carboxylic acid (4-bromophenyl)amide;
4-Methyl-2-(3-methylbenzoylamino)thiazole-5-carboxylic acid (4-bromophenyl)amide;
2-(2-Fluorobenzoylamino)-4-methylthiazole-5-carboxylic acid (4-chlorophenyl)amide;
2-(2-Fluorobenzoylamino)-4-methylthiazole-5-carboxylic acid (2-chlorophenyl)amide;
2-(3-Fluorobenzoylamino)-4-methylthiazole-5-carboxylic acid indan-5-ylamide;
3-Methyl-1-phenyl-1H-thieno[2,3-c]pyrazole-5-carboxylic acid [5-(4-chloro-phenylcarbamoyl)-4-methylthiazol-2-yl]amide;
4-Methyl-2-(3-phenylacryloylamino)thiazole-5-carboxylic acid (3-chlorophenyl)amide;
2-Acetylamino-4-methylthiazole-5-carboxylic acid (3-methoxyphenyl)amide;
4-Methyl-2-(4-nitrobenzoylamino)thiazole-5-carboxylic acid (4-methoxyphenyl)amide;
2-Acetylamino-4-methylthiazole-5-carboxylic acid (4-chlorophenyl)amide;
2-Acetylamino-4-methylthiazole-5-carboxylic acid (4-methoxyphenyl)amide;
4-Methyl-2-(4-methylbenzoylamino)thiazole-5-carboxylic acid (5-methyl[1,3,4]thiadiazol-2-yl)amide;
2-(4-Bromobenzoylamino)-4-methylthiazole-5-carboxylic acid phenylamide;
4-Methyl-2-(3-phenylacryloylamino)thiazole-5-carboxylic acid (4-methoxyphenyl)amide;
4-Methyl-2-propionylaminothiazole-5-carboxylic acid (4-methoxyphenyl)amide;
2-(Cyclopropanecarbonylamino)-4-methylthiazole-5-carboxylic acid (4-methoxyphenyl)amide;
4-Methyl-2-propionylamino-thiazole-5-carboxylic acid (4-bromophenyl)amide;
4-Methyl-2-(4-nitrobenzoylamino)thiazole-5-carboxylic acid (2-chlorophenyl)amide;
{[2-(4-Fluorobenzoylamino)-4-methylthiazole-5-carbonyl]-amino}acetic acid ethyl ester;
{[2-(3-Fluorobenzoylamino)-4-methylthiazole-5-carbonyl]-amino}acetic acid ethyl ester;
2-(2-Fluorobenzoylamino)-4-methylthiazole-5-carboxylic acid (4-methoxyphenyl)amide;
N-[4-Methyl-5-(piperidine-1-carbonyl)thiazol-2-yl]-2-phenoxyacetamide;
2-(4-tert-Butylbenzoylamino)-4-methylthiazole-5-carboxylic acid (4-bromophenyl)amide;
4-Methyl-2-(3-phenylacryloylamino)thiazole-5-carboxylic acid (4-bromophenyl)amide;
4-Methyl-2-(3-phenylacryloylamino)thiazole-5-carboxylic acid (4-chlorophenyl)amide;
2-(4-tert-Butylbenzoylamino)-4-methylthiazole-5-carboxylic acid (3-chlorophenyl)amide;
2-(4-tert-Butylbenzoylamino)-4-methylthiazole-5-carboxylic acid (2-chlorophenyl)amide;
4-Methyl-2-(3-phenylacryloylamino)thiazole-5-carboxylic acid benzylamide;
2-(4-tert-Butylbenzoylamino)-4-methylthiazole-5-carboxylic acid cyclohexylamide;
2-(4-Methoxybenzoylamino)-4-methylthiazole-5-carboxylic acid (5-methyl[1,3,4]thiadiazol-2-yl)amide;
4-Methyl-2-(4-nitrobenzoylamino)thiazole-5-carboxylic acid o-tolylamide;
2-Benzoylamino-4-methylthiazole-5-carboxylic acid (4-bromophenyl)amide;
4-Methyl-2-(2-methylbenzoylamino)thiazole-5-carboxylic acid (4-bromophenyl)amide;
4-Methyl-2-(2-phenoxyacetylamino)thiazole-5-carboxylic acid (4-bromophenyl)amide;
3-Methyl-1-phenyl-1H-thieno[2,3-c]pyrazole-5-carboxylic acid [5-(4-bromo-phenylcarbamoyl)-4-methylthiazol-2-yl]amide;
4-Methyl-2-(4-nitrobenzoylamino)thiazole-5-carboxylic acid (4-chlorophenyl)amide;
2-Benzoylamino-4-methylthiazole-5-carboxylic acid (3-chlorophenyl)amide;
4-Methyl-2-(2-phenoxyacetylamino)thiazole-5-carboxylic acid (3-chlorophenyl)amide;
3-Methyl-1-phenyl-1H-thieno[2,3-c]pyrazole-5-carboxylic acid [5-(3-chloro-phenylcarbamoyl)-4-methylthiazol-2-yl]amide;
2-Benzoylamino-4-methylthiazole-5-carboxylic acid o-tolylamide;
4-Methyl-2-(2-phenoxy-acetylamino)thiazole-5-carboxylic acid (3-methoxyphenyl)amide;
2-Benzoylamino-4-methylthiazole-5-carboxylic acid (2,3-dihydrobenzo[1,4]dioxin-6-yl)amide;
3-Methyl-1-phenyl-1H-thieno[2,3-c]pyrazole-5-carboxylic acid (5-benzylcarbamoyl-4-methylthiazol-2-yl)amide;
4-Methyl-2-propionylaminothiazole-5-carboxylic acid (3-methoxyphenyl)amide;
3-Methyl-1-phenyl-1H-thieno[2,3-c]pyrazole-5-carboxylic acid [5-(3-methoxy-phenylcarbamoyl)-4-methylthiazol-2-yl]amide;

4-Methyl-2-(2-methylbenzoylamino)thiazole-5-carboxylic acid indan-5-ylamide;
2-Benzoylamino-4-methylthiazole-5-carboxylic acid (4-methoxyphenyl)amide;
4-Methyl-2-(2-phenoxy-acetylamino)thiazole-5-carboxylic acid (4-methoxyphenyl)amide;
4-Methyl-2-(3,4,5-trimethoxybenzoylamino)thiazole-5-carboxylic acid (4-methoxyphenyl)amide;
2-(Cyclopropanecarbonylamino)-4-methylthiazole-5-carboxylic acid o-tolylamide;
4-Methyl-2-propionylaminothiazole-5-carboxylic acid (4-chlorophenyl)amide;
4-Methyl-2-propionylaminothiazole-5-carboxylic acid (3-chlorophenyl)amide;
4-Methyl-2-propionylaminothiazole-5-carboxylic acid (2-chlorophenyl)amide;
4-Methyl-2-(4-nitro-benzoylamino)thiazole-5-carboxylic acid (3-chlorophenyl)amide;
2-(4-Fluorobenzoylamino)-4-methylthiazole-5-carboxylic acid (2,3-dihydrobenzo[1,4]dioxin-6-yl)amide;
2-(4-Fluorobenzoylamino)-4-methylthiazole-5-carboxylic acid indan-5-ylamide;
4-Fluoro-N-[4-methyl-5-(piperidine-1-carbonyl)thiazol-2-yl]benzamide;
2-(4-tert-Butylbenzoylamino)-4-methylthiazole-5-carboxylic acid indan-5-ylamide;
4-Methyl-2-propionylaminothiazole-5-carboxylic acid cyclohexylamide;
N-[4-Methyl-5-(piperidine-1-carbonyl)thiazol-2-yl]propionamide;
2-(Cyclopropanecarbonylamino)-4-methylthiazole-5-carboxylic acid (3-chlorophenyl)amide;
2-(3-Fluorobenzoylamino)-4-methylthiazole-5-carboxylic acid (3-methoxyphenyl)amide;
2-(Cyclopropanecarbonylamino)-4-methylthiazole-5-carboxylic acid (2-chlorophenyl)amide;
4-Methyl-2-(4-nitrobenzoylamino)thiazole-5-carboxylic acid phenylamide;
2-(Cyclopropanecarbonylamino)-4-methylthiazole-5-carboxylic acid cyclohexylamide;
4-Methyl-2-(4-nitrobenzoylamino)thiazole-5-carboxylic acid (2,3-dihydrobenzo[1,4]dioxin-6-yl)amide;
2-(4-tert-Butylbenzoylamino)-4-methylthiazole-5-carboxylic acid phenylamide;
4-Methyl-2-(3-phenylacryloylamino)thiazole-5-carboxylic acid phenylamide;
4-Methyl-2-(3-phenylacryloylamino)thiazole-5-carboxylic acid o-tolylamide;
4-Methyl-2-[(thiophene-2-carbonyl)amino]thiazole-5-carboxylic acid (5-methyl-[1,3,4]thiadiazol-2-yl)amide;
4-Methyl-2-(3-phenylacryloylamino)thiazole-5-carboxylic acid (2-chlorophenyl)amide;
4-Methyl-2-(4-nitrobenzoylamino)thiazole-5-carboxylic acid (4-bromophenyl)amide;
4-Methyl-2-(3-phenylacryloylamino)thiazole-5-carboxylic acid indan-5-ylamide;
4-Methyl-2-(3-phenylacryloylamino)thiazole-5-carboxylic acid (2-hydroxyethyl)amide;
3-Methyl-1-phenyl-1H-thieno[2,3-c]pyrazole-5-carboxylic acid (5-cyclohexylcarbamoyl-4-methylthiazol-2-yl)amide;
{[2-(2-Fluorobenzoylamino)-4-methylthiazole-5-carbonyl]amino}acetic acid ethyl ester;
4-Methyl-2-(3,4,5-trimethoxybenzoylamino)thiazole-5-carboxylic acid (4-bromophenyl)amide;
2-(Cyclohexanecarbonylamino)-4-methylthiazole-5-carboxylic acid benzylamide;
N-[4-Methyl-5-(morpholine-4-carbonyl)thiazol-2-yl]-3-phenylacrylamide;
N-[4-Methyl-5-(morpholine-4-carbonyl)thiazol-2-yl]-4-nitrobenzamide;
{[4-Methyl-2-(3-phenylacryloylamino)thiazole-5-carbonyl]amino}acetic acid ethyl ester;
4-Methyl-2-(3-phenylacryloylamino)thiazole-5-carboxylic acid (2,3-dihydrobenzo[1,4]dioxin-6-yl)amide;
4-Methyl-2-(3-phenylacryloylamino)thiazole-5-carboxylic acid pyridin-3-ylamide;
N-[4-Methyl-5-(piperidine-1-carbonyl)-thiazol-2-yl]-3-phenyl-acrylamide;
4-Methyl-2-(3-phenylacryloylamino)thiazole-5-carboxylic acid cyclohexylamide;
4-Methyl-2-(3,4,5-trimethoxybenzoylamino)thiazole-5-carboxylic acid (5-methyl-[1,3,4]thiadiazol-2-yl)amide;
4-Methyl-2-propionylaminothiazole-5-carboxylic acid o-tolylamide;
Cyclopropanecarboxylic acid [4-methyl-5-(piperidine-1-carbonyl)thiazol-2-yl]amide;
4-Methyl-2-(2-phenoxyacetylamino)thiazole-5-carboxylic acid o-tolylamide;
4-Methyl-2-(2-phenoxyacetylamino)thiazole-5-carboxylic acid (2,3-dihydrobenzo[1,4]dioxin-6-yl)amide;
2-(Cyclopropanecarbonylamino)-4-methylthiazole-5-carboxylic acid (4-bromophenyl)amide;
4-Methyl-2-(3,4,5-trimethoxybenzoylamino)thiazole-5-carboxylic acid indan-5-ylamide;
2-[(Adamantane-1-carbonyl)amino]-4-methylthiazole-5-carboxylic acid cyclohexylamide;
2-(3-Chlorobenzoylamino)-4-methylthiazole-5-carboxylic acid pyridin-3-ylamide;
2-(3-Chlorobenzoylamino)-4-methylthiazole-5-carboxylic acid cyclohexylamide;
{[4-Methyl-2-(3,4,5-trimethoxybenzoylamino)thiazole-5-carbonyl]amino}acetic acid ethyl ester;
4-Methyl-2-(2-methylbenzoylamino)thiazole-5-carboxylic acid (3-chlorophenyl)amide;
2-(4-Chloro-benzoylamino)-4-methylthiazole-5-carboxylic acid cyclohexylamide;
4-Methyl-2-(4-methylbenzoylamino)thiazole-5-carboxylic acid (2-dimethylaminoethyl)amide;
5-tert-Butyl-2-methyl-2H-pyrazole-3-carboxylic acid (7,7-dimethyl-4-oxo-5,6,7,8-tetrahydro-4H-thiazolo[5,4-c]azepin-2-yl)amide;
2-[(5-Chloro-3-methyl-1-phenyl-1H-pyrazole-4-carbonyl)amino]-4-methylthiazole-5-carboxylic acid indan-5-ylamide;
4-Methyl-2-(4-nitrobenzoylamino)thiazole-5-carboxylic acid indan-5-ylamide;
2-Acetylamino-4-methylthiazole-5-carboxylic acid (5-methyl-[1,3,4]thiadiazol-2-yl)amide;
2-Chloro-N-(7,7-dimethyl-4-oxo-5,6,7,8-tetrahydro-4H-thiazolo[5,4-c]azepin-2-yl)-benzamide;
N-(7,7-Dimethyl-4-oxo-5,6,7,8-tetrahydro-4H-thiazolo[5,4-c]azepin-2-yl)benzamide;
N-(4-Oxo-5,6,7,8-tetrahydro-4H-thiazolo[5,4-c]azepin-2-yl)benzamide;
2-Chloro-N-(4-oxo-5,6,7,8-tetrahydro-4H-thiazolo[5,4-c]azepin-2-yl)benzamide;
2-(3,4-Dimethoxybenzoylamino)-4-methylthiazole-5-carboxylic acid dimethylamide;
4-Methyl-2-(2-phenylpropionylamino)thiazole-5-carboxylic acid dimethylamide;
2-(2,6-Difluorobenzoylamino)-4-methylthiazole-5-carboxylic acid dimethylamide;

3-Chloro-N-[4-methyl-5-(piperidine-1-carbonyl)-thiazol-2-yl]benzamide;
2-[2-(4-Chloro-2-methylphenoxy)propionylamino]-4-methylthiazole-5-carboxylic acid dimethylamide;
6,8-Dimethyl-2-pyridin-4-yl-quinoline-4-carboxylic acid (5-dimethylcarbamoyl-4-methylthiazol-2-yl)amide;
4-Methyl-2-[(3-methylbenzofuran-2-carbonyl)amino]thiazole-5-carboxylic acid dimethylamide;
2-Acetylamino-4-methylthiazole-5-carboxylic acid (3-chlorophenyl)amide;
4-Methyl-2-(2-phenoxyacetylamino)thiazole-5-carboxylic acid indan-5-ylamide;
5-(7,7-Dimethyl-4-oxo-5,6,7,8-tetrahydro-4H-thiazolo[5,4-c]azepin-2-ylcarbamoyl)-thiophene-2-carboxylic acid methyl ester;
4-Methyl-2-(3-methylbenzoylamino)thiazole-5-carboxylic acid cyclohexylamide;
4-Methyl-2-(3-phenylacryloylamino)thiazole-5-carboxylic acid (3-methoxyphenyl)amide;
4-Methyl-2-(4-nitrobenzoylamino)thiazole-5-carboxylic acid (3-methoxyphenyl)amide;
2-[(Adamantane-1-carbonyl)amino]-4-methylthiazole-5-carboxylic acid (3-methoxyphenyl)amide; and
2-Benzoylamino-4-methylthiazole-5-carboxylic acid benzylmethylamide.

Example 28

Measuring Stearoyl-CoA Desaturase Inhibition Activity of a Test Compound Using Mouse Liver Microsomes The identification of compounds of the invention as SCD inhibitors was readily accomplished using the SCD microsomal assay procedure described in Shanklin J. and Summerville C., *Proc. Natl. Acad. Sci. USA* (1991), Vol. 88, pp. 2510-2514.

Preparation of Mouse Liver Microsomes:

Male ICR outbread mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1:3 w/v) containing 0.25 M sucrose, 62 mM potassium phosphate buffer (pH 7.0), 0.15 M KCl, 15 mM N-acetyleysteine, 5 mM $MgCl_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a S-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Desaturase activity is measured as the release of $^3H_2O$ from [9,10-$^3$H]stearoyl-CoA. Reactions per assay point conditions are as follows: 2 μL 1.5 mM stearoyl-CoA, 0.25 μL 1 mCi/mL $^3$H stearoyl-CoA, 10 μL 20 mM NADH, 36.75 uL 0.1 M PK buffer ($K_2HPO_4$/$NaH_2PO_4$, pH 7.2). The test compound or control solution is added in a 1 μL volume. Reactions are started by the addition of 50 μL of microsomes (1.25 mg/mL). The plates are mixed and after 15 min incubation on a heating block (25° C.), the reactions are stopped by the addition of 10 μL 60% PCA. An aliquot of 100 μL is then transferred to a filter plate pretreated with charcoal and the plate centrifuged at 4000 rpm for 1 minute. The flow through containing the $^3H_2O$ released by the SCD1 desaturation reaction is added to scintillation fluid and the radioactivity is measured in a Packard TopCount. The data is analyzed to identify the $IC_{50}$ for test compounds and reference compounds.

Those skilled in the art are aware of a variety of modifications to this assay that can be useful for measuring inhibition of stearoyl-CoA desaturase activity in microsomes or in cells by test compounds.

Representative compounds of the invention showed activity as inhibitors of SCD when tested in this assay. The activity was defined in terms of % SCD enzyme activity remaining at the desired concentration of the test compound or as the $IC_{50}$ concentration.

All of the U.S. patents, U.S. patent application publications, U.S. patent applications, foreign patents, foreign patent applications and non-patent publications referred to in this specification are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating a disease or condition mediated by stearoyl-CoA desaturase in a mammal, wherein the method comprises administering to the mammal in need thereof a therapeutically effective amount of a compound selected from:
    2-(4-Bromobenzoylamino)-4-methylthiazole-5-carboxylic acid o-tolylamide;
    2-(4-Bromobenzoylamino)-4-methylthiazole-5-carboxylic acid (2-chlorophenyl)amide;
    2-(4-Bromobenzoylamino)-4-methylthiazole-5-carboxylic acid (3-methoxyphenyl)amide;
    4-Methyl-2-(3,4,5-trimethoxybenzoylamino)thiazole-5-carboxylic acid phenylamide;
    4-Methyl-2-(4-methylbenzoylamino)thiazole-5-carboxylic acid (4-methoxyphenyl)amide;
    4-Methyl-2-[(thiophene-2-carbonyl)amino]thiazole-5-carboxylic acid (4-chlorophenyl)amide;
    2-(Cyclohexanecarbonylamino)-4-methylthiazole-5-carboxylic acid (2,3-dihydro-benzo[1,4]dioxin-6-yl)amide;
    2-(4-Methoxybenzoylamino)-4-methylthiazole-5-carboxylic acid pyridin-3-ylamide;
    2-Benzoylamino-4-methylthiazole-5-carboxylic acid (5-methyl[1,3,4]thiadiazol-2-yl)amide;
    2-[(Furan-2-carbonyl)amino]-4-methylthiazole-5-carboxylic acid o-tolylamide;
    2-[(Furan-2-carbonyl)amino]-4-methylthiazole-5-carboxylic acid (4-bromophenyl)amide;
    2-(3-Methoxybenzoylamino)-4-methylthiazole-5-carboxylic acid (4-bromophenyl)amide;
    2-[Furan-2-carbonyl)amino]-4-methylthiazole-5-carboxylic acid (4-chlorophenyl)amide;
    2-[(Furan-2-carbonyl)amino]-4-methylthiazole-5-carboxylic acid (3-methoxyphenyl)amide;
    2-[(Furan-2-carbonyl)amino]-4-methylthiazole-5-carboxylic acid (4-methoxyphenyl)amide;

4-Methyl-2-(2-phenoxyacetylamino)thiazole-5-carboxylic acid phenylamide;
4-Methyl-2-(2-phenoxyacetylamino)thiazole-5-carboxylic acid benzylamide;
2-Chloro-N-[4-methyl-5-(morpholine-4-carbonyl)thiazol-2-yl]benzamide;
2-(3-Fluorobenzoylamino)-4-methylthiazole-5-carboxylic acid (4-bromophenyl)amide;
2-(2-Fluorobenzoylamino)-4-methylthiazole-5-carboxylic acid (4-bromophenyl)amide;
2-Acetylamino-4-methylthiazole-5-carboxylic acid indan-5-ylamide;
2-Acetylamino-4-methylthiazole-5-carboxylic acid cyclohexylamide;
2-(4-Fluorobenzoylamino)-4-methylthiazole-5-carboxylic acid (4-bromophenyl)amide;
2-Benzoylamino-4-methylthiazole-5-carboxylic acid phenylamide;
2-Benzoylamino-4-methylthiazole-5-carboxylic acid (3-methoxyphenyl)amide;
2-(4-Fluorobenzoylamino)-4-methylthiazole-5-carboxylic acid (4-methoxyphenyl)amide;
4-Methyl-2-propionylaminothiazole-5-carboxylic acid indan-5-ylamide;
2-(Cyclopropanecarbonylamino)-4-methylthiazole-5-carboxylic acid phenylamide;
2-(Cyclopropanecarbonylamino)-4-methylthiazole-5-carboxylic acid (4-chlorophenyl)amide;
2-(4-Fluorobenzoylamino)-4-methylthiazole-5-carboxylic acid phenylamide;
2-(4-Fluorobenzoylamino)-4-methylthiazole-5-carboxylic acid o-tolylamide;
2-(4-Fluorobenzoylamino)-4-methylthiazole-5-carboxylic acid (4-chlorophenyl)amide,
2-(4-Fluorobenzoylamino)-4-methylthiazole-5-carboxylic acid (2-chlorophenyl)amide;
2-(4-Fluorobenzoylamino)-4-methylthiazole-5-carboxylic acid (3-methoxyphenyl)amide;
N-[4-Methyl-5-(piperidine-1-carbonyl)-thiazol-2-yl]benzamide;
2-(Cyclopropanecarbonylamino)-4-methylthiazole-5-carboxylic acid benzylamide;
2-(Cyclopropanecarbonylamino)-4-methylthiazole-5-carboxylic acid indan-5-ylamide;
4-Methyl-2-(4-methylbenzoylamino)thiazole-5-carboxylic acid pyridin-3-ylamide,
4-Methyl-2-propionylaminothiazole-5-carboxylic acid benzylamide;
[(2-Benzoylamino-4-methylthiazole-5-carbonyl)amino]acetic acid ethyl ester;
N-[4-Methyl-5-(morpholine-4-carbonyl)thiazol-2-yl]propionamide;
N-(5-Benzylcarbamoyl)-4-methylthiazol-2-yl)isonicotinamide,
N-[5-(3-Chlorophenylcarbamoyl)-4-methylthiazol-2-yl]isonicotinamide;
N-[5-(2-Chlorophenylcarbamoyl)-4-methylthiazol-2-yl]isonicotinamide;
N-(4-Oxo-5,6,7,8-tetrahydro-4H-thiazolol[5,4-c]azepin-2-yl)acetamide;
N-(7,7-Dimethyl-4-oxo-5,6,7,8-tetrahydro-4H-thiazolo[5,4-c]azepin-2-yl)acetamide;
2-(3-Fluorobenzoylamino)-4-methylthiazole-5-carboxylic acid phenylamide;
4-Methyl-2-(4-methylbenzoylamino)thiazole-5-carboxylic acid o-tolylamide;
2-(2-Fluorobenzoylamino)-4-methylthiazole-5-carboxylic acid o-tolylamide;
2-(4-Bromobenzoylamino)-4-methylthiazole-5-carboxylic acid (4-chlorophenyl)amide;
4-Methyl-2-(3,4,5-trimethoxybenzoylamino)thiazole-5-carboxylic acid (4-chlorophenyl)amide;
2-(4-Bromobenzoylamino)-4-methylthiazole-5-carboxylic acid (3-chlorophenyl)amide;
4-Methyl-2-(3-methylbenzoylamino)thiazole-5-carboxylic acid (3-chlorophenyl)amide;
2-(3-Fluorobenzoylamino)-4-methylthiazole-5-carboxylic acid (3-chlorophenyl)amide;
4-Methyl-2-(2-methylbenzoylamino)thiazole-5-carboxylic acid (2-chlorophenyl)amide;
4-Methyl-2-(3,4,5-trimethoxybenzoylamino)thiazole-5-carboxylic acid (2-chlorophenyl)amide;
4-Methyl-2-(3-methylbenzoylamino)thiazole-5-carboxylic acid (2-chlorophenyl)amide;
2-(3-Fluorobenzoylamino)-4-methylthiazole-5-carboxylic acid (2-chlorophenyl)amide;
2-(4-Bromobenzoylamino)-4-methylthiazole-5-carboxylic acid (2,3-dihydro-benzo[1,4]dioxin-6-yl)amide;
2-(4-Methoxybenzoylamino)-4-methylthiazole-5-carboxylic acid (2,3-dihydro-benzo[1,4]dioxin-6-yl)amide;
4-Methyl-2-(3-methylbenzoylamino)thiazole-5-carboxylic acid (2,3-dihydrobenzo[1,4]dioxin-6-yl)amide;
2-(4-Bromobenzoylamino)-4-methylthiazole-5-carboxylic acid benzylamide;
2-(4-Bromobenzoylamino)-4-methylthiazole-5-carboxylic acid indan-5-ylamide;
4-Methyl-2-(3-methylbenzoylamino)thiazole-5-carboxylic acid indan-5-ylamide;
4-Methyl-2-(3,4,5-trimethoxybenzoylamino)thiazole-5-carboxylic acid cyclohexylamide;
2-Fluoro-N-[4-methyl-5-(piperidine-1-carbonyl)thiazol-2-yl]benzamide;
4-Bromo-N-[4-methyl-5-(morpholine-4-carbonyl)thiazol-2-yl]benzamide;
4-Methoxy-N-[4-methyl-5-(morpholine-4-carbonyl)thiazol-2-yl]benzamide;
2-(Cyclohexanecarbonylamino)-4-methylthiazole-5-carboxylic acid (4-methoxyphenyl)amide;
4-Methyl-2-(3,4,5-trimethoxybenzoylamino)thiazole-5-carboxylic acid o-tolylamide;
4-Methyl-2-(3,4,5-trimethoxybenzoylamino)thiazole-5-carboxylic acid (3-chlorophenyl)amide;
2-(4-Methoxybenzoylamino)-4-methylthiazole-5-carboxylic acid (3-methoxyphenyl)amide;
4-Methyl-2-(4-methylbenzoylamino)thiazole-5-carboxylic acid (2,3-dihydrobenzo[1,4]dioxin-6-yl)amide;
4-Methyl-2-(3,4,5-trimethoxybenzoylamino)thiazole-5-carboxylic acid (2,3-dihydro-benzo[1,4]dioxin-6-yl)amide;
4-Methyl-2-(4-methylbenzoylamino)thiazole-5-carboxylic acid benzylamide;
4-Methyl-2-(4-methylbenzoylamino)thiazole-5-carboxylic acid indan-5-ylamide;
4-Methyl-2-(4-methylbenzoylamino)thiazole-5-carboxylic acid (4-chlorophenyl)amide;
4-Methyl-2-(4-methylbenzoylamino)thiazole-5-carboxylic acid (3-chlorophenyl)amide;
4-Methyl-2-(4-methylbenzoylamino)thiazole-5-carboxylic acid (2-chlorophenyl)amide;
4-Methyl-2-(4-methylbenzoylamino)thiazole-5-carboxylic acid (3-methoxyphenyl)amide;

4-Methyl-2-(4-methylbenzoylamino)thiazole-5-carboxylic acid phenylamide;
2-(Cyclohexanecarbonylamino)-4-methylthiazole-5-carboxylic acid (4-chlorophenyl)amide;
2-(Cyclohexanecarbonylamino)-4-methylthiazole-5-carboxylic acid (2-chlorophenyl)amide;
3-Methyl-1-phenyl-1H-thieno[2,3-c]pyrazole-5-carboxylic acid [5-(2-chloro-phenylcarbamoyl)-4-methylthiazol-2-yl]amide;
2-(Cyclohexanecarbonylamino)-4-methylthiazole-5-carboxylic acid indan-5-ylamide;
{[2-(4-Methoxy-benzoylamino)-4-methylthiazole-5-carbonyl]amino}acetic acid ethyl ester;
3-Fluoro-N-[4-methyl-5-(morpholine-4-carbonyl)thiazol-2-yl]benzamide;
2-[(5-Chloro-3-methyl-1-phenyl-1H-pyrazole-4-carbonyl)amino]-4-methylthiazole-5-carboxylic acid cyclohexylamide;
4-Methyl-2-(3-phenylacryloylamino)thiazole-5-carboxylic acid (2-dimethylaminoethyl)amide;
2-[(Furan-2-carbonyl)amino]-4-methylthiazole-5-carboxylic acid phenylamide;
2-[(Adamantane-1-carbonyl)amino]-4-methylthiazole-5-carboxylic acid phenylamide;
2-[(Adamantane-1-carbonyl)amino]-4-methylthiazole-5-carboxylic acid (4-bromophenyl)amide;
2-(3-Methoxybenzoylamino)-4-methylthiazole-5-carboxylic acid (4-chlorophenyl)amide;
2-[(Furan-2-carbonyl)amino]-4-methylthiazole-5-carboxylic acid (3-chlorophenyl)amide;
2-(3-Methoxybenzoylamino)-4-methylthiazole-5-carboxylic acid (3-chlorophenyl)amide;
2-(3-Methoxybenzoylamino)-4-methylthiazole-5-carboxylic acid (2-chlorophenyl)amide;
2-(3-Methoxybenzoylamino)-4-methylthiazole-5-carboxylic acid (2,3-dihydro-benzo[1,4]dioxin-6-yl)amide;
2-(3-Methoxybenzoylamino)-4-methylthiazole-5-carboxylic acid indan-5-ylamide;
{[2-(3-Methoxybenzoylamino)-4-methylthiazole-5-carbonyl]amino}acetic acid ethyl ester;
2-(4-Bromobenzoylamino)-4-methylthiazole-5-carboxylic acid (5-methyl[1,3,4]thiadiazol-2-yl)amide;
2-(3-Methoxy-benzoylamino)-4-methylthiazole-5-carboxylic acid (4-methoxyphenyl)amide;
2-[(Adamantane-1-carbonyl)amino]-4-methylthiazole-5-carboxylic acid (4-methoxyphenyl)amide;
3-Methyl-1-phenyl-1H-thieno[2,3-c]pyrazole-5-carboxylic acid (4-methyl-5-phenylcarbamoyl-thiazol-2-yl)amide;
3-Methyl-1-phenyl-1H-thieno[2,3-c]pyrazole-5-carboxylic acid (4-methyl-5-o-tolylcarbamoyl-thiazol-2-yl)amide;
2-[(5-Chloro-3-methyl-1-phenyl-1H-pyrazole-4-carbonyl)amino]-4-methylthiazole-5-carboxylic acid (4-bromophenyl)amide;
2-[(5-Chloro-3-methyl-1-phenyl-1H-pyrazole-4-carbonyl)amino]-4-methylthiazole-5-carboxylic acid (2-chlorophenyl)amide;
3-Methyl-1-phenyl-1H-thieno[2,3-c]pyrazole-5-carboxylic acid [5-(2,3-dihydro-benzo[1,4]dioxin-6-ylcarbamoyl)-4-methylthiazol-2-yl]amide;
3-Methyl-1-phenyl-1H-thieno[2,3-c]pyrazole-5-carboxylic acid [5-(indan-5-ylcarbamoyl)-4-methylthiazol-2-yl]amide;
3-Methyl-1-phenyl-1H-thieno[2,3-c]pyrazole-5-carboxylic acid [4-methyl-5-(5-methyl-[1,3,4]thiadiazol-2-ylcarbamoyl)thiazol-2-yl]amide;
3-Methyl-1-phenyl-1H-thieno[2,3-c]pyrazole-5-carboxylic acid [4-methyl-5-(piperidine-1-carbonyl)thiazol-2-yl]amide;
3-Methyl-N-[4-methyl-5-(piperidine-1-carbonyl)thiazol-2-yl]benzamide;
3-Methyl-1-phenyl-1H-thieno[2,3-c]pyrazole-5-carboxylic acid [5-(4-methoxy-phenylcarbamoyl)-4-methylthiazol-2-yl]amide;
4-Methyl-2-(4-methylbenzoylamino)thiazole-5-carboxylic acid cyclohexylamide;
2-(Cyclohexanecarbonylamino)-4-methylthiazole-5-carboxylic acid (3-chlorophenyl)amide;
4-Methyl-2-[(thiophene-2-carbonyl)amino]thiazole-5-carboxylic acid (2,3-dihydro-benzo[1,4]dioxin-6-yl)amide;
2-[(Adamantane-1-carbonyl)amino]-4-methylthiazole-5-carboxylic acid benzylamide;
4-Methyl-2-(4-methylbenzoylamino)thiazole-5-carboxylic acid (4-bromophenyl)amide;
2-(Cyclohexanecarbonylamino)-4-methylthiazole-5-carboxylic acid (4-bromophenyl)amide;
4-Methyl-2-(3-methylbenzoylamino)thiazole-5-carboxylic acid (4-bromophenyl)amide;
2-(2-Fluorobenzoylamino)-4-methylthiazole-5-carboxylic acid (4-chlorophenyl)amide;
2-(2-Fluorobenzoylamino)-4-methylthiazole-5-carboxylic acid (2-chlorophenyl)amide;
2-(3-Fluorobenzoylamino)-4-methylthiazole-5-carboxylic acid indan-5-ylamide;
3-Methyl-1-phenyl-1H-thieno[2,3-c]pyrazole-5-carboxylic acid [5-(4-chloro-phenylcarbamoyl)-4-methylthiazol-2-yl]amide;
4-Methyl-2-(3-phenylacryloylamino)thiazole-5-carboxylic acid (3-chlorophenyl)amide;
2-Acetylamino-4-methylthiazole-5-carboxylic acid (3-methoxyphenyl)amide;
4-Methyl-2-(4-nitrobenzoylamino)thiazole-5-carboxylic acid (4-methoxyphenyl)amide;
2-Acetylamino-4-methylthiazole-5-carboxylic acid (4-chlorophenyl)amide;
2-Acetylamino-4-methylthiazole-5-carboxylic acid (4-methoxyphenyl)amide;
4-Methyl-2-(4-methylbenzoylamino)thiazole-5-carboxylic acid (5-methyl[1,3,4]thiadiazol-2-yl)amide;
2-(4-Bromobenzoylamino)-4-methylthiazole-5-carboxylic acid phenylamide;
4-Methyl-2-(3-phenylacryloylamino)thiazole-5-carboxylic acid (4-methoxyphenyl)amide;
4-Methyl-2-propionylaminothiazole-5-carboxylic acid (4-methoxyphenyl)amide;
2-(Cyclopropanecarbonylamino)-4-methylthiazole-5-carboxylic acid (4-methoxyphenyl)amide;
4-Methyl-2-propionylamino-thiazole-5-carboxylic acid (4-bromophenyl)amide;
4-Methyl-2-(4-nitrobenzoylamino)thiazole-5-carboxylic acid (2-chlorophenyl)amide;
{[2-(4-Fluorobenzoylamino)-4-methylthiazole-5-carbonyl]amino}acetic acid ethyl ester;
{[2-(3-Fluorobenzoylamino)-4-methylthiazole-5-carbonyl]amino}acetic acid ethyl ester;
2-(2-Fluorobenzoylamino)-4-methylthiazole-5-carboxylic acid (4-methoxyphenyl)amide;
N-[4-Methyl-5-(piperidine-1-carbonyl)thiazol-2-yl]-2-phenoxyacetamide;

2-(4-tert-Butylbenzoylamino)-4-methylthiazole-5-carboxylic acid (4-bromophenyl)amide;
4-Methyl-2-(3-phenylacryloylamino)thiazole-5-carboxylic acid (4-bromophenyl)amide;
4-Methyl-2-(3-phenylacryloylamino)thiazole-5-carboxylic acid (4-chlorophenyl)amide;
2-(4-tert-Butylbenzoylamino)-4-methylthiazole-5-carboxylic acid (3-chlorophenyl)amide;
2-(4-tert-Butylbenzoylamino)-4-methylthiazole-5-carboxylic acid (2-chlorophenyl)amide;
4-Methyl-2-(3-phenylacryloylamino)thiazole-5-carboxylic acid benzylamide;
2-(4-tert-Butylbenzoylamino)-4-methylthiazole-5-carboxylic acid cyclohexylamide;
2-(4-Methoxybenzoylamino)-4-methylthiazole-5-carboxylic acid (5-methyl[1,3,4]thiadiazol-2-yl)amide;
4-Methyl-2-(4-nitro-benzoylamino)thiazole-5-carboxylic acid o-tolylamide;
2-Benzoylamino-4-methylthiazole-5-carboxylic acid (4-bromophenyl)amide;
4-Methyl-2-(2-methylbenzoylamino)thiazole-5-carboxylic acid (4-bromophenyl)amide;
4-Methyl-2-(2-phenoxyacetylamino)thiazole-5-carboxylic acid (4-bromophenyl)amide;
3-Methyl-1-phenyl-1H-thieno[2,3-c]pyrazole-5-carboxylic acid [5-(4-bromo-phenylcarbamoyl)-4-methylthiazol-2-yl]amide;
4-Methyl-2-(4-nitrobenzoylamino)thiazole-5-carboxylic acid (4-chlorophenyl)amide;
2-Benzoylamino-4-methylthiazole-5-carboxylic acid (3-chlorophenyl)amide;
4-Methyl-2-(2-phenoxyacetylamino)thiazole-5-carboxylic acid (3-chlorophenyl)amide;
3-Methyl-1-phenyl-1H-thieno[2,3-c]pyrazole-5-carboxylic acid [5-(3-chloro-phenylcarbamoyl)-4-methylthiazol-2-yl]amide;
2-Benzoylamino-4-methylthiazole-5-carboxylic acid o-tolylamide;
4-Methyl-2-(2-phenoxy-acetylamino)thiazole-5-carboxylic acid (3-methoxyphenyl)amide;
2-Benzoylamino-4-methylthiazole-5-carboxylic acid (2,3-dihydrobenzo[1,4]dioxin-6-yl)amide;
3-Methyl-1-phenyl-1H-thieno[2,3-c]pyrazole-5-carboxylic acid (5-benzylcarbamoyl-4-methylthiazol-2-yl)amide;
4-Methyl-2-propionylaminothiazole-5-carboxylic acid (3-methoxyphenyl)amide;
3-Methyl-1-phenyl-1H-thieno[2,3-c]pyrazole-5-carboxylic acid [5-(3-methoxy-phenylcarbamoyl)-4-methylthiazol-2-yl]amide;
4-Methyl-2-(2-methylbenzoylamino)thiazole-5-carboxylic acid indan-5-ylamide;
2-Benzoylamino-4-methylthiazole-5-carboxylic acid (4-methoxyphenyl)amide;
4-Methyl-2-(2-phenoxyacetylamino)thiazole-5-carboxylic acid (4-methoxyphenyl)amide;
4-Methyl-2-(3,4,5-trimethoxybenzoylamino)thiazole-5-carboxylic acid (4-methoxyphenyl)amide;
2-(Cyclopropanecarbonylamino)-4-methylthiazole-5-carboxylic acid o-tolylamide;
4-Methyl-2-propionylaminothiazole-5-carboxylic acid (4-chlorophenyl)amide;
4-Methyl-2-propionylaminothiazole-5-carboxylic acid (3-chlorophenyl)amide;
4-Methyl-2-propionylaminothiazole-5-carboxylic acid (2-chlorophenyl)amide;
4-Methyl-2-(4-nitrobenzoylamino)thiazole-5-carboxylic acid (3-chlorophenyl)amide;
2-(4-Fluorobenzoylamino)-4-methylthiazole-5-carboxylic acid (2,3-dihydrobenzo[1,4]dioxin-6-yl)amide;
2-(4-Fluorobenzoylamino)-4-methylthiazole-5-carboxylic acid indan-5-ylamide;
4-Fluoro-N-[4-methyl-5-(piperidine-1-carbonyl)thiazol-2-yl]benzamide;
2-(4-tert-Butylbenzoylamino)-4-methylthiazole-5-carboxylic acid indan-5-ylamide;
4-Methyl-2-propionylaminothiazole-5-carboxylic acid cyclohexylamide;
N-[4-Methyl-5-(piperidine-1-carbonyl)thiazol-2-yl]propionamide;
2-(Cyclopropanecarbonylamino)-4-methylthiazole-5-carboxylic acid (3-chlorophenyl)amide;
2-(3-Fluorobenzoylamino)-4-methylthiazole-5-carboxylic acid (3-methoxyphenyl)amide;
2-(Cyclopropanecarbonylamino)-4-methylthiazole-5-carboxylic acid (2-chlorophenyl)amide;
4-Methyl-2-(4-nitrobenzoylamino)thiazole-5-carboxylic acid phenylamide;
2-(Cyclopropanecarbonylamino)-4-methylthiazole-5-carboxylic acid cyclohexylamide;
4-Methyl-2-(4-nitrobenzoylamino)thiazole-5-carboxylic acid (2,3-dihydrobenzo[1,4]dioxin-6-yl)amide;
2-(4-tert-Butylbenzoylamino)-4-methylthiazole-5-carboxylic acid phenylamide;
4-Methyl-2-(3-phenylacryloylamino)thiazole-5-carboxylic acid phenylamide;
4-Methyl-2-(3-phenylacryloylamino)thiazole-5-carboxylic acid o-tolylamide;
4-Methyl-2-[(thiophene-2-carbonyl)amino]thiazole-5-carboxylic acid (5-methyl-[1,3,4]thiadiazol-2-yl)amide;
4-Methyl-2-(3-phenylacryloylamino)thiazole-5-carboxylic acid (2-chlorophenyl)amide;
4-Methyl-2-(4-nitrobenzoylamino)thiazole-5-carboxylic acid (4-bromophenyl)amide;
4-Methyl-2-(3-phenylacryloylamino)thiazole-5-carboxylic acid indan-5-ylamide;
4-Methyl-2-(3-phenylacryloylamino)thiazole-5-carboxylic acid (2-hydroxy-ethyl)amide;
3-Methyl-1-phenyl-1H-thieno[2,3-c]pyrazole-5-carboxylic acid (5-cyclohexylcarbamoyl-4-methylthiazol-2-yl)amide;
{[2-(2-Fluorobenzoylamino)-4-methylthiazole-5-carbonyl]amino}acetic acid ethyl ester;
4-Methyl-2-(3,4,5-trimethoxybenzoylamino)thiazole-5-carboxylic acid (4-bromophenyl)amide;
2-(Cyclohexanecarbonylamino)-4-methylthiazole-5-carboxylic acid benzylamide;
N-[4-Methyl-5-(morpholine-4-carbonyl)thiazol-2-yl]-3-phenylacrylamide;
N-[4-Methyl-5-(morpholine-4-carbonyl)thiazol-2-yl]-4-nitrobenzamide;
{[4-Methyl-2-(3-phenylacryloylamino)thiazole-5-carbonyl]amino}acetic acid ethyl ester;
4-Methyl-2-(3-phenylacryloylamino)thiazole-5-carboxylic acid (2,3-dihydrobenzo[1,4]dioxin-6-yl)amide;
4-Methyl-2-(3-phenylacryloylamino)thiazole-5-carboxylic acid pyridin-3-ylamide;
N-[4-Methyl-5-(piperidine-1-carbonyl)thiazol-2-yl]-3-phenylacrylamide;
4-Methyl-2-(3-phenylacryloylamino)thiazole-5-carboxylic acid cyclohexylamide;

4-Methyl-2-(3,4,5-trimethoxybenzoylamino)thiazole-5-carboxylic acid (5-methyl-[1,3,4]thiadiazol-2-yl)amide;
4-Methyl-2-propionylaminothiazole-5-carboxylic acid o-tolylamide;
Cyclopropanecarboxylic acid [4-methyl-5-(piperidine-1-carbonyl)thiazol-2-yl]amide;
4-Methyl-2-(2-phenoxyacetylamino)thiazole-5-carboxylic acid o-tolylamide;
4-Methyl-2-(2-phenoxyacetylamino)thiazole-5-carboxylic acid (2,3-dihydrobenzo[1,4]dioxin-6-yl)amide;
2-(Cyclopropanecarbonylamino)-4-methylthiazole-5-carboxylic acid (4-bromophenyl)amide;
4-Methyl-2-(3,4,5-trimethoxybenzoylamino)thiazole-5-carboxylic acid indan-5-ylamide
2-[(Adamantane-1-carbonyl)amino]-4-methylthiazole-5-carboxylic acid cyclohexylamide;
2-(3-Chlorobenzoylamino)-4-methylthiazole-5-carboxylic acid pyridin-3-ylamide;
2-(3-Chlorobenzoylamino)-4-methylthiazole-5-carboxylic acid cyclohexylamide;
{[4-Methyl-2-(3,4,5-trimethoxybenzoylamino)thiazole-5-carbonyl]amino}acetic acid ethyl ester;
4-Methyl-2-(2-methylbenzoylamino)thiazole-5-carboxylic acid (3-chlorophenyl)amide;
2-(4-Chlorobenzoylamino)-4-methylthiazole-5-carboxylic acid cyclohexylamide;
4-Methyl-2-(4-methylbenzoylamino)thiazole-5-carboxylic acid (2-dimethylaminoethyl)amide;
5-tert-Butyl-2-methyl-2H-pyrazole-3-carboxylic acid (7,7-dimethyl-4-oxo-5,6,7,8-tetrahydro-4H-thiazolo[5,4-c]azepin-2-yl)amide;
2-[(5-Chloro-3-methyl-1-phenyl-1H-pyrazole-4-carbonyl)amino]-4-methylthiazole-5-carboxylic acid indan-5-ylamide;
4-Methyl-2-(4-nitrobenzoylamino)thiazole-5-carboxylic acid indan-5-ylamide;
2-Acetylamino-4-methylthiazole-5-carboxylic acid (5-methyl[1,3,4]thiadiazol-2-yl)amide;
2-Chloro-N-(7,7-dimethyl-4-oxo-5,6,7,8-tetrahydro-4H-thiazolo[5,4-c]azepin-2-yl)-benzamide;
N-(7,7-Dimethyl-4-oxo-5,6,7,8-tetrahydro-4H-thiazolo[5,4-c]azepin-2-yl)benzamide;
N-(4-Oxo-5,6,7,8-tetrahydro-4H-thiazolo[5,4-c]azepin-2-yl)benzamide;
2-Chloro-N-(4-oxo-5,6,7,8-tetrahydro-4H-thiazolo[5,4-c]azepin-2-yl)benzamide;
2-(3,4-Dimethoxybenzoylamino)-4-methylthiazole-5-carboxylic acid dimethylamide;
4-Methyl-2-(2-phenyl-propionylamino)thiazole-5-carboxylic acid dimethylamide;
2-(2,6-Difluorobenzoylamino)-4-methylthiazole-5-carboxylic acid dimethylamide;
3-Chloro-N-[4-methyl-5-(piperidine-1-carbonyl)thiazol-2-yl]benzamide;
2-[2-(4-Chloro-2-methylphenoxy)propionylamino]-4-methylthiazole-5-carboxylic acid dimethylamide;
6,8-Dimethyl-2-pyridin-4-ylquinoline-4-carboxylic acid (5-dimethylcarbamoyl-4-methylthiazol-2-yl)amide;
4-Methyl-2-[(3-methylbenzofuran-2-carbonyl)amino]thiazole-5-carboxylic acid dimethylamide;
2-Acetylamino-4-methylthiazole-5-carboxylic acid (3-chlorophenyl)amide;
4-Methyl-2-(2-phenoxyacetylamino)thiazole-5-carboxylic acid indan-5-ylamide;
5-(7,7-Dimethyl-4-oxo-5,6,7,8-tetrahydro-4H-thiazolo[5,4-c]azepin-2-ylcarbamoyl)-thiophene-2-carboxylic acid methyl ester;
4-Methyl-2-(3-methylbenzoylamino)thiazole-5-carboxylic acid cyclohexylamide;
4-Methyl-2-(3-phenylacryloylamino)thiazole-5-carboxylic acid (3-methoxyphenyl)amide;
4-Methyl-2-(4-nitrobenzoylamino)thiazole-5-carboxylic acid (3-methoxyphenyl)amide;
2-[(Adamantane-1-carbonyl)amino]-4-methylthiazole-5-carboxylic acid (3-methoxyphenyl)amide;
N-[5-(2-Cyclopropylethylcarbamoyl)-4-methylthiazol-2-yl]isonicotinamide;
N-(4-Methyl-5-phenethylcarbamoylthiazol-2-yl)isonicotinamide;
N-[4-Methyl-5-(3-phenylpropylcarbamoyl)thiazol-2-yl]isonicotinamide;
N-[5-(4-Chlorobenzylcarbamoyl)-4-methylthiazol-2-yl]isonicotinamide;
2-(Cyclopropanecarbonylamino)-4-methylthiazole-5-carboxylic acid 4-chloro-benzylamide;
2-(2,5-Difluorobenzoylamino)-4-methylthiazole-5-carboxylic acid benzylamide;
2-(Cyclobutanecarbonylamino)-4-methylthiazole-5-carboxylic acid benzylamide;
4-Methyl-2-[(2-phenylcyclopropanecarbonyl)amino]thiazole-5-carboxylic acid benzylamide;
2-(2-Fluorobenzoylamino)-4-methylthiazole-5-carboxylic acid benzylamide;
2-(2,2-Dimethylpropionylamino)-4-methylthiazole-5-carboxylic acid benzylamide;
2-Benzoylamino-4-methylthiazole-5-carboxylic acid benzylamide;
4-Methyl-2-(2-trifluoromethylbenzoylamino)thiazole-5-carboxylic acid benzylamide;
2-(4-Chlorobenzoylamino)-4-methylthiazole-5-carboxylic acid benzylamide;
2-(4-Fluorobenzoylamino)-4-methylthiazole-5-carboxylic acid benzylamide;
4-Methyl-2-(4-trifluoromethylbenzoylamino)thiazole-5-carboxylic acid benzylamide;
2-(2-Chlorobenzoylamino)-4-methylthiazole-5-carboxylic acid benzylamide;
2-(2,4-Dichlorobenzoylamino)-4-methylthiazole-5-carboxylic acid benzylamide;
2-(Cyclopentanecarbonylamino)-4-methylthiazole-5-carboxylic acid benzylamide;
2-(2-Chloro-4-fluorobenzoylamino)-4-methylthiazole-5-carboxylic acid benzylamide;
2-(3-Chlorobenzoylamino)-4-methylthiazole-5-carboxylic acid benzylamide
4-Methyl-2-(2-trifluoromethoxybenzoylamino)thiazole-5-carboxylic acid benzylamide;
2-(3,5-Dichlorobenzoylamino)-4-methylthiazole-5-carboxylic acid benzylamide;
2-(3-Cyanobenzoylamino)-4-methylthiazole-5-carboxylic acid benzylamide;
2-(5-Chloro-2-fluorobenzoylamino)-4-methylthiazole-5-carboxylic acid benzylamide;
2-(3-Fluorobenzoylamino)-4-methylthiazole-5-carboxylic acid benzylamide;
4-Methyl-2-(4-trifluoromethoxybenzoylamino)thiazole-5-carboxylic acid benzylamide;
4-Methyl-2-(3-trifluoromethylbenzoylamino)thiazole-5-carboxylic acid benzylamide;
2-(3-Methoxybenzoylamino)-4-methylthiazole-5-carboxylic acid benzylamide;

4-Methyl-2-[(naphthalene-1-carbonyl)amino]thiazole-5-carboxylic acid benzylamide;
2-(4-Cyanobenzoylamino)-4-methylthiazole-5-carboxylic acid benzylamide;
2-(3,5-Difluorobenzoylamino)-4-methylthiazole-5-carboxylic acid benzylamide;
4-Methyl-2-(3-trifluoromethoxybenzoylamino)thiazole-5-carboxylic acid benzylamide;
2-(4-Methoxybenzoylamino)-4-methylthiazole-5-carboxylic acid benzylamide;
2-(3-Methanesulfonylbenzoylamino)-4-methylthiazole-5-carboxylic acid benzylamide;
2-(2-Methanesulfonylbenzoylamino)-4-methylthiazole-5-carboxylic acid benzylamide;
2-Benzoylamino-4-trifluoromethylthiazole-5-carboxylic acid benzylamide;
N-(5-Benzylcarbamoyl-4-methylthiazol-2-yl)nicotinamide;
2-(3,4-Dichlorobenzoylamino)-4-methylthiazole-5-carboxylic acid benzylamide;
2-(4-Methanesulfonylbenzoylamino)-4-methylthiazole-5-carboxylic acid benzylamide;
4-Methyl-2-(3-phenylpropionylamino)thiazole-5-carboxylic acid benzylamide;
2-Benzylamino-4-methylthiazole-5-carboxylic acid benzylamide;
4-Methyl-2-phenylacetylaminothiazole-5-carboxylic acid benzylamide;
2-Benzoylamino-4-phenylthiazole-5-carboxylic acid benzylamide;
4-Methyl-2-(3-phenylureido)thiazole-5-carboxylic acid benzylamide;
2-[3-(4-Fluorophenyl)ureido]-4-methylthiazole-5-carboxylic acid benzylamide;
2-[3-(4-Chlorophenyl)ureido]-4-methylthiazole-5-carboxylic acid benzylamide;
2-(2-Cyclopropylacetylamino)-4-methylthiazole-5-carboxylic acid benzylamide;
2-Benzoylamino-4-methylthiazole-5-carboxylic acid 2-trifluoromethylbenzylamide;
2-Benzoylamino-4-methylthiazole-5-carboxylic acid 3-chlorobenzylamide;
2-Benzoylamino-4-methylthiazole-5-carboxylic acid cyclopropylmethyl-amide;
2-Benzoylamino-4-methylthiazole-5-carboxylic acid 3-fluorobenzylamide;
2-Benzoylamino-4-methylthiazole-5-carboxylic acid 2-chlorobenzylamide;
2-Benzoylamino-4-methylthiazole-5-carboxylic acid 2-fluorobenzylamide;
2-Benzoylamino-4-methylthiazole-5-carboxylic acid 4-fluorobenzylamide;
2-Benzoylamino-4-methylthiazole-5-carboxylic acid benzylmethylamide;
2-Benzoylamino-4-chlorothiazole-5-carboxylic acid benzylamide;
2-[(4-Pentylbenzoyl)amino]-N-(phenylmethyl)-4-(trifluoromethyl)-5-thiazolecarboxamide;
2-Benzoylamino-4-methylthiazole-5-carboxylic acid (1-phenylpropyl)amide;
4-Methyl-2-(toluene-4-sulfonylamino)thiazole-5-carboxylic acid benzylamide;
4-Methyl-2-[4-(2H-tetrazol-5-yl)benzoylamino]thiazole-5-carboxylic acid benzylamide;
4-Amino-2-benzoylaminothiazole-5-carboxylic acid benzylamide;
N-[5-(N-Benzoylhydrazinocarbonyl)-4-methylthiazol-2-yl]benzamide;
N-[5-(Imidazole-1-carbonyl)-4-methylthiazol-2-yl]benzamide;
4-Methyl-2-(4-phenylbutyrylamino)thiazole-5-carboxylic acid benzylamide;
4-Methyl-2-(5-phenylpentanoylamino)thiazole-5-carboxylic acid benzylamide;
4-Methyl-2-[4-(2-oxo-2H-pyridin-1-yl)benzoylamino]-thiazole-5-carboxylic acid benzylamide;
2-[(5-Benzylcarbamoyl-4-methyl-thiazol-2-ylcarbamoyl)methyl]benzoic acid;
N-(5-Benzylcarbamoyl-4-methylthiazol-2-yl)-2-methoxyisonicotinamide;
2-Oxo-1,2-dihydropyridine-4-carboxylic acid (5-benzylcarbamoyl-4-methylthiazol-2-yl)amide;
2-Oxo-1-phenyl-1,2-dihydropyridine-4-carboxylic acid (5-benzylcarbamoyl-4-methyl-thiazol-2-yl)amide;
N,4-Dibenzyl-2-(3-phenylpropanamido)thiazole-5-carboxamide;
2-Benzamido-N,4-dibenzylthiazole-5-carboxamide;
2-(4-Bromo-2-hydroxymethylbenzoylamino)-4-methyl-thiazole-5-carboxylic acid benzylamide;
N-benzyl-4-methyl-2-(N-methylbenzamido)thiazole-5-carboxamide;
N-benzyl-N,4-dimethyl-2-(N-methylbenzamido)thiazole-5-carboxamide;
2-(4-((1H-pyrazol-1-yl)methyl)benzamido)-N-benzyl-4-methylthiazole-5-carboxamide;
N-Benzyl-4-(morpholinomethyl)-2-(3-phenylpropanamido)thiazole-5-carboxamide;
N-benzyl-2-(4-benzylbenzamido)-4-methylthiazole-5-carboxamide;
2-(4-Benzylbenzoylamino)-4-diethylaminomethylthiazole-5-carboxylic acid benzylamide;
2-Benzamido-N-benzyl-4-((diethylamino)methyl)thiazole-5-carboxamide;
2-(4-Benzylbenzamido)-N-(2-cyanoethyl)-4-methylthiazole-5-carboxamide;
2-(4-Benzylbenzamido)-N-ethyl-4-methylthiazole-5-carboxamide; or
N-Benzyl-2-(4-benzylbenzamido)-4-amethylamino)methyl)thiazole-5-carboxamide;
or a stereoisomer, enantiomer or tautomer thereof, or a racemic or non-racemic mixture thereof, or a pharmaceutically acceptable salt or solvate thereof;
where the disease or condition which is mediated by stearoyl-CoA desaturase is selected from the group consisting of diabetes, diabetic complications, impaired glucose tolerance, and obesity or any combination of these,
wherein the compound administered is optionally in the form of a pharmaceutical composition with at least one pharmaceutically acceptable excipient.

2. The method of claim 1 wherein the mammal is a human.

3. The method of claim 1 wherein the disease or condition is Type II diabetes, Type I diabetes or non-insulin-dependent diabetes mellitus.

4. The method of claim 1, wherein the composition further comprises a compound selected from the group consisting of insulin, insulin sensitizer, biguanide, alpha-glucosidase inhibitors, meglitinides, HMG-CoA reductase inhibitors, cholestyramine, fibrates, nicotinic acid, thiazolidinediones and aspirin.

* * * * *